US008513380B2

(12) United States Patent
Barker

(10) Patent No.: US 8,513,380 B2
(45) Date of Patent: Aug. 20, 2013

(54) PEPTIDES FOR BINDING FIBRINOGEN AND FIBRIN

(75) Inventor: Thomas Harrison Barker, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 13/382,466

(22) PCT Filed: Jul. 9, 2010

(86) PCT No.: PCT/US2010/041527
§ 371 (c)(1),
(2), (4) Date: Jan. 5, 2012

(87) PCT Pub. No.: WO2011/006069
PCT Pub. Date: Jan. 13, 2011

(65) Prior Publication Data
US 2012/0114682 A1    May 10, 2012

Related U.S. Application Data

(60) Provisional application No. 61/224,188, filed on Jul. 9, 2009.

(51) Int. Cl.
*C07K 2/00*    (2006.01)
(52) U.S. Cl.
USPC ............ 530/300; 530/381; 530/382; 514/1.1; 514/13.6; 514/802
(58) Field of Classification Search
None
See application file for complete search history.

(56) References Cited

U.S. PATENT DOCUMENTS

| | | | |
|---|---|---|---|
| 6,083,481 A | 7/2000 | Dean et al. | |
| 2005/0261472 A1* | 11/2005 | Wescott et al. | 530/328 |
| 2007/0044171 A1* | 2/2007 | Kovalic et al. | 800/278 |
| 2007/0083334 A1* | 4/2007 | Mintz et al. | 702/19 |
| 2009/0183270 A1* | 7/2009 | Adams et al. | 800/260 |
| 2011/0214205 A1* | 9/2011 | Dietrich et al. | 800/281 |

OTHER PUBLICATIONS

Ahmed, et al., "Fibrin: a versatile scaffold for tissue engineering applications", Tissue Eng Part B Rev, 14(2):199-215 (2008).
Ariens, et al., "Role of factor XIII in fibrin clot formation and effects of genetic polymorphisms", Blood, 100(3):743-54 (2002).
Arrighi, et al., "Bone healing induced by local delivery of an engineered parathyroid hormone prodrug", Biomaterials, 30(9):1763-71 (2009).
Barker, et al., "Modification of fibrinogen with poly(ethylene glycol) and its effects on fibrin clot characteristics", J Biomed Mater Res, 56(4):529-535 (2001).
Blomback, et al., "Fibrinopeptides and fibrin gel structure", Biophys Chem, 112 (2-3):147-51 (2004).

Breen, et al., "Fibrin as a delivery system for therapeutic drugs and biomolecules", Tissue Eng Part B Rev, 15(2): 201-14 (2009).
Ehrbar, et al., "Endothelial cell proliferation and progenitor maturation by fibrin-bound VEGF variants with differential susceptibilities to local cellular activity", J Control Release, 101(1-3):93-109 (2005).
Everse, et al., "Crystal structure of fragment double-D from human fibrin with two different bound ligands", Biochemistry, 37(24):8637-42 (1998).
Geer, et al., "Role of 'B-b' knob-hole interactions in fibrin binding to adsorbed fibrinogen", J Thromb Haemost, 5(12):2344-51 (2007).
Hall, et al., "Matrix-bound sixth Ig-like domain of cell adhesion molecule L1 acts as an angiogenic factor by ligating alphavbeta3-integrin and activating VEGF-R2", Microvasc Res, 68(3):169-78 2004).
Kawasaki, et al., "Amino acids and peptides. XVI. Synthesis of N-terminal tetrapeptide analogs of fibrin alpha-chain and their inhibitory effects on fibrinogen/thrombin clotting", Chem Pharm Bull (Tokyo), 40(12),3253-60 (1992).
Kostelansky, et al., "2.8 A crystal structures of recombinant fibrinogen fragment D with and without two peptide ligands: GHRP binding to the "b" site disrupts its nearby calcium-binding site", Biochemistry, 41(40):12124-32 (2002).
Laudano, et al., "Studies on synthetic peptides that bind to fibrinogen and prevent fibrin polymerization. Structural requirements, Number of binding sites, and species differences", Biochemistry, 19(5)1013-19 (1980).
Laudano, et al., "Synthetic peptide derivatives that bind to fibrinogen and prevent the polymerization of fibrin monomers", 75(7):3085-9 (1978).
Laudano, et al., "Influence of calcium ion on the binding of fibrin amino terminal peptides to fibrinogen", Science, 212(4493):457-9 (1981).
Laurens, et al.,"Fibrin structure and wound healing", J Thromb Haemost, 4 (5):932-9 (2006).
Leahy, et al., "2.0 A crystal structure of a four-domain segment of human fibronectin encompassing the RGD loop and synergy region", Cell, 84(1):155-64 (1996).
Litvinov, et al., "Polymerization of fibrin: specificity, strength, and stability of knob-hole interactions studied at the single-molecule level", Blood, 106 (9):2944-51 (2005).
Litvinov, et al., "Polymerization of fibrin: Direct observation and quantification of individual B:b knob-hole interactions", Blood, 109(1):130-8 (2007).
Lord, "Fibrinogen and fibrin: scaffold proteins in hemostasis", Curr Opin Hematol, 14(3):236-41(2007).

(Continued)

*Primary Examiner* — Christina Bradley
*Assistant Examiner* — Kristina M Hellman
(74) *Attorney, Agent, or Firm* — Pabst Patent Group LLP

(57) ABSTRACT

Compositions and methods for targeting substances to fibrinogen, fibrin monomers, or fibrin polymers are provided. These compositions and methods generally involve the use of fibrin knob peptides that bind fibrin(ogen), which can be used to detect fibrin(ogen) and modulate fibrin polymerization and fibrinolysis.

7 Claims, 34 Drawing Sheets

(56) References Cited

OTHER PUBLICATIONS

Martino, et al., "Controlling integrin specificity and stem cell differentiation in 2D and 3D environments through regulation of fibronectin domain stability", Biomaterials, 30 (6):1089-97(2009).
Morton, et al., "Interpreting complex binding kinetics from optical biosensors: a comparison of analysis by linearization, the integrated rate equation, and numerical integration", Anal Biochem, 227(1):176-85 (1995).
Mosesson, "Fibrinogen and fibrin structure and functions", Thromb Haemost, 3 (8):1894-1904(2005).
Petrie, et al., "Integrin specificity and enhanced cellular activities associated with surfaces presenting a recombinant fibronectin fragment compared to RGD supports", Biomatenals, 27(31):5459-70 (2006).
Pittier, et al., "Neurite extension and in vitro myelination within three-dimensional modified fibrin matrices", J Neurobiol, 63(1):1-14 (2005).
Sakiyama-Elbert, et al., "Development of fibrin derivatives for controlled release of heparin-binding growth factors", J Control Release, 65(3):389-402 (2000).
Sakiyama-Elbert, et al., "Controlled release of nerve growth factor from a heparin-containing fibrin-based cell ingrowth matrix", J Control Release, 69 (1):149-58 (2000).
Schense, et al., "Cross-linking exogenous bifunctional peptides into fibrin gels with factor XIIIa", Bioconjug Chem, 10(1):75-81 (1999).
Schmoekel, et al., "Bone repair with a form of BMP-2 engineered for incorporation into fibrin cell ingrowth matrices", Biotechnol Bioeng, 89(3):253-62 (2005).
Spotnitz, et al., "Hemostats, sealants, and adhesives: components of the surgical toolbox", Transfusion, 48(7):1502-16 (2008).
Taylor, et al., "Controlled release of neurotrophin-3 from fibrin gels for spinal cord injury", J Control Release, 98(2):281-94 (2004).
UNIPROT Accession No. A3MTD9, Copeland, et al., "*Pyrobaculum calidifontis*", 1 page, First available Apr. 3, 2007, Updated May 5, 2009, accessed Nov. 26, 2010.
UNIPROT Accession No. A4FV80, Moore, et al., "Bos Taurus", 1 page, First available Feb. 5, 2008, Updated Oct. 14, 2008, accessed Nov. 26, 2010.
UNIPROT Accession No. A9G247, Schneiker, et al., "*Sorangium cellulosum*", 1 page, First available Apr. 17, 2007, Updated Mar. 3, 2009, accessed Nov. 26, 2010.
Weisel, et al.,"Computer modeling of fibrin polymerization kinetics correlated with electron microscope and turbidity observations: clot structure and assembly are kinetically controlled", Biophys J, 63(1):111-28 (1992).
Weisel, "Fibrin assembly. Lateral aggregation and the role of the two pairs of fibrinopeptides", Biophys J, 50(6):1079-93 (1986).
Weisel, "Which knobs fit into which holes in fibrin polymerization?" J Thromb Haemost, 5(12):2340-3(2007).
Willerth, et al.,"Rationally designed peptides for controlled release of nerve growth factor from fibrin matrices", J Biomed Mater Res A, 80(1):13-23 (2007).
Wood, et al., "Release rate controls biological activity of nerve growth factor released from fibrin matrices containing affinity-based delivery systems", J Biomed Mater Res A, 84(2):300-12 (2008).
Yang, et al., "A model of fibrin formation based on crystal structures of fibrinogen and fibrin fragments complexed with synthetic peptides", PNAS, 97(26):14156-61 (2000).

\* cited by examiner

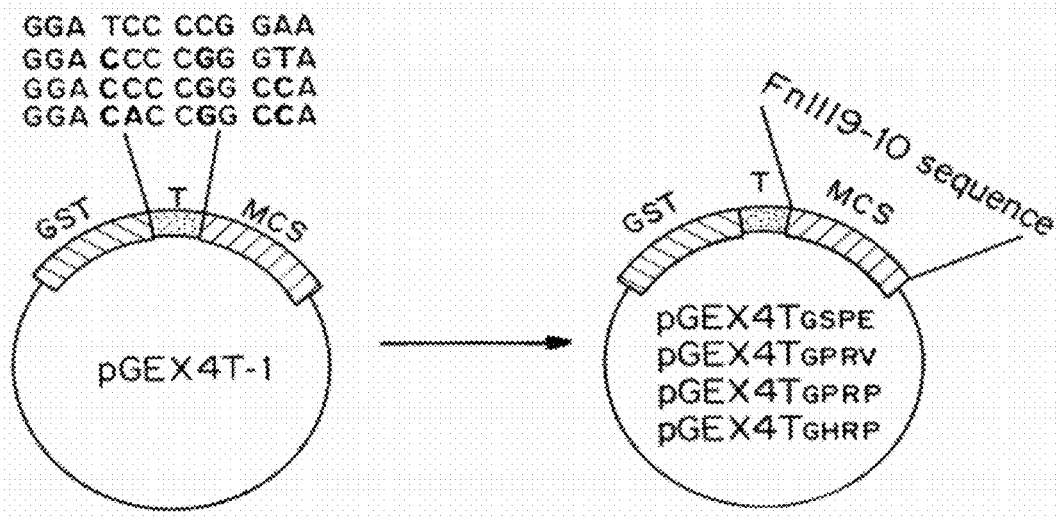
FIG. 2
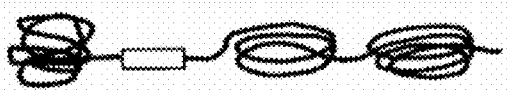

PEPTIDES FOR BINDING FIBRINOGEN AND FIBRIN

CROSS REFERENCE TO RELATED APPLICATIONS

This application claims benefit of U.S. Provisional Application No. 61/224,188, filed Jul. 9, 2009, which is hereby incorporated herein by reference in its entirety.

STATEMENT REGARDING FEDERALLY SPONSORED RESEARCH OR DEVELOPMENT

This invention was made with Government Support under Agreement 1R21EB008463 and K12 GM000680 by the National Institutes of Health. The Government has certain rights in the invention.

REFERENCE TO SEQUENCE LISTING

The Sequence Listing submitted Jul. 9, 2010, as a text file named "GTRC_4021_ST25.txt," created on Jul. 7, 2010, and having a size of 6,764 bytes is hereby incorporated by reference.

FIELD OF THE INVENTION

The invention is generally related to peptides and fusion proteins and their use for incorporating substances into fibrin polymers.

BACKGROUND OF THE INVENTION

Fibrin, formed in response to vascular injury, constitutes the protein polymeric scaffold known as the provisional extracellular matrix. Fibrin serves as the temporary initial scaffolding for the invasion of inflammatory and repair cells into wound environments. Fibrinogen, the inactive precursor to fibrin, is a 340 kDa plasma glycoprotein that circulates in blood plasma at concentrations of 2 to 4 mg/mL. As a part of its normal functions, fibrin(ogen) features a variety of binding sites for self-regulatory enzymes (including thrombin, factor XIII, plasminogen, tissue plasminogen activator), ECM components, growth factors, cytokines and cell receptors; components that are critical in the remodeling of the matrix as part of the wound healing response (Laurens N, et al. J Thromb Haemost 2006, 4(5):932-939; Mosesson M W. J Thromb Haemost 2005, 3(8):1894-1904). Due to the ease of purification of this highly expressed plasma protein and its native role in the guidance of wound repair, the fibrinogen/fibrin system is employed in a number of surgical hemostats and tissue sealants (FDA-approved products include Tisseel®, Evicel™) and is actively used as a biomaterial for developing therapeutic strategies in regenerative medicine (Spotnitz W D, et al. Transfusion 2008; 48(7):1502-1516; Ahmed T A, et al. Tissue Eng Part B Rev 2008, 14(2):199-215; Breen A, et al. Tissue Eng Part B Rev 2009, 15(2): 201-214).

Significant efforts have been made to develop and enhance fibrin as a tissue scaffold and drug delivery vehicle through both modification of the molecule and engagement of the native polymer system biology. For instance, functionalized polyethylene glycol was explored as a means to covalently tether therapeutic proteins to fibrinogen's backbone thus enabling their delivery in fibrin polymers (Barker T H, et al. J Biomed Mater Res 2001, 56(4):529-535). Alternatively, factor XIIIa, also responsible for the covalent attachment of other non-fibrin proteins (e.g. fibronectin, α2-plasmin inhibitor) to the C-terminus of the Aα chains in vivo, has been shown to be a reproducible method of crosslinking RGD-containing peptides into fibrin gels during coagulation (Schense J C, et al. Bioconjug Chem 1999, 10(1):75-81). The factor XIIIa substrate sequence has subsequently been used for the incorporation of recombinantly-produced growth factors, cell adhesion molecules and morphogens into fibrin matrices, usually with an additional protease-sensitive cleavage site to facilitate their release from fibrin (Ehrbar M, et al. J Control Release 2005, 101(1-3):93-109; Schmoekel H G, et al. Biotechnol Bioeng 2005, 89(3):253-262; Pittier R, et al. J Neurobiol 2005, 63(1):1-14; Arrighi I, et al. Biomaterials 2009, 30(9):1763-0.1771; Hall H, et al. Microvasc Res 2004, 68(3):169-178). As an intriguing spin-off, bi-domain peptides comprising the factor XIIIa substrate sequence and the heparin-binding domain have been used to increase the concentration of fibrin-bound heparin, thereby improving the retention characteristics of heparin-binding growth factors (Willerth S M, et al. J Biomed Mater Res A 2007, 80(1):13-23; Wood M D, et al. J Biomed Mater Res A 2008, 84(2):300-312; Sakiyama-Elbert S E, et al. J Control Release 2000, 65(3):389-402; Sakiyama-Elbert S E, et al. J Control Release 2000, 69(1):149-158). In particular, such biomimetic affinity-based systems are advantageous for the local delivery of factors that are internalized by cells as part of the signaling process. These methods, however, require intermediary molecules or enzymes, like factor XIIIa, to conjugate the agents to fibrin, and the desired deliverable, such as a drug or protein, can not be incorporated prior to the initiation of polymer.

It is an object of the invention to provide improved methods of incorporating therapeutic agents into a fibrin polymer.

It is a further object of the invention to target substances to fibrinogen and fibrin within a subject.

It is a further object of the invention to provide methods for detecting fibrin polymers in a subject.

It is a further object of the invention to promote wound healing in a subject.

It is a further object of the invention to provide fibrin polymers with modified physical properties.

SUMMARY OF THE INVENTION

In accordance with the purpose of this invention, as embodied and broadly described herein, this invention relates to compositions and methods for targeting substances to fibrinogen, fibrin monomers, or fibrin polymers. These compositions and methods generally involve the use of fibrin knob peptides that bind fibrin(ogen), which can be used to detect fibrin(ogen) and modulate fibrin polymerization and fibrinolysis.

Isolated polypeptides are provided that include fibrin knobs at the N-terminus of the polypeptide, wherein the isolated polypeptide binds fibrin. Recombinant fusion proteins are also provided that contain a fibrin knob peptide at the N-terminus of the fusion protein and therefore bind fibrin. The recombinant fusion proteins can contain any polypeptide suitable to target to fibrin(ogen). In some embodiments, the fusion proteins include a bioactive polypeptide that promotes wound healing or fibrinolysis. In some embodiments, the fusion protein contains or is conjugated to an inert protein that sterically hinders fibrin polymerization when the fusion protein binds fibrin.

Methods of targeting agents to fibrin(ogen) within a subject are also provided, involving administering to the subject a pharmaceutical composition comprising a fibrin knob peptide conjugated to the agent. The agent can be any molecule, protein, polymer, nucleic acid, or the like that is suitable for administration to a subject and for targeting to fibrin(ogen). For example, the agent can be a detectable label, a bioactive polypeptide that promotes wound healing or fibrinolysis, or an inert protein or polymer that hinders fibrin polymerization when the fusion protein binds fibrin. Therefore, methods are provided for diagnosing or treating diseases in a subject that involve fibrin overproduction, such as pulmonary fibrosis and fibrin clots.

Methods of treating a wound in a subject are also provided that involve simultaneously administering to the wound a first pharmaceutical composition and second pharmaceutical composition, wherein the first pharmaceutical composition comprises a fibrin knob peptide conjugated to an agent, wherein the second pharmaceutical composition comprises thrombin. In these methods, the agent conjugated to the fibrin knob peptide preferably promotes healing, promotes fibrinolysis, or sterically hinders fibrin polymerization Additional advantages of the disclosed composition(s) and method(s) will be set forth in part in the description which follows, and in part will be understood from the description, or may be learned by practice of the disclosed composition(s) and method(s). The advantages of the disclosed composition(s) and method(s) will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

FIG. 2 is an illustration of a cloning method for molecular engineering of the pGEX4T-1 vector to express proteins with variable thrombin cleavage sites, which allow for the presentation of the knob sequence at the N-terminus following thrombin treatment. Site-directed mutagenesis was used to modify the coding sequence for the thrombin cleavage site (T) (SEQ ID NOs:33-36). Next, the open reading frame of the protein-of-interest, $FnIII_{9-10}$, was inserted into the multiple cloning site (MCS). The expressed proteins comprise an N-terminal glutathione S-transferase (GST) tag, followed by the thrombin cleavage site and protein-of-interest.

FIGS. 7B and 6D are line graphs showing percent cumulative release as a function of time ($\sqrt{h^{0.5}}$) using GPRP-$FnIII_{9-10}$ (SEQ ID NO:1, FIG. 7B) or GSPE-$FnIII_{9-10}$ (SEQ ID NO:11, FIG. 7D) fusion proteins upon the addition of 1 U/mL factor XIIIa and 1 U/mL human α-thrombin (circle) or batroxobin moojeni (square).

DETAILED DESCRIPTION OF THE INVENTION

Figure 1:
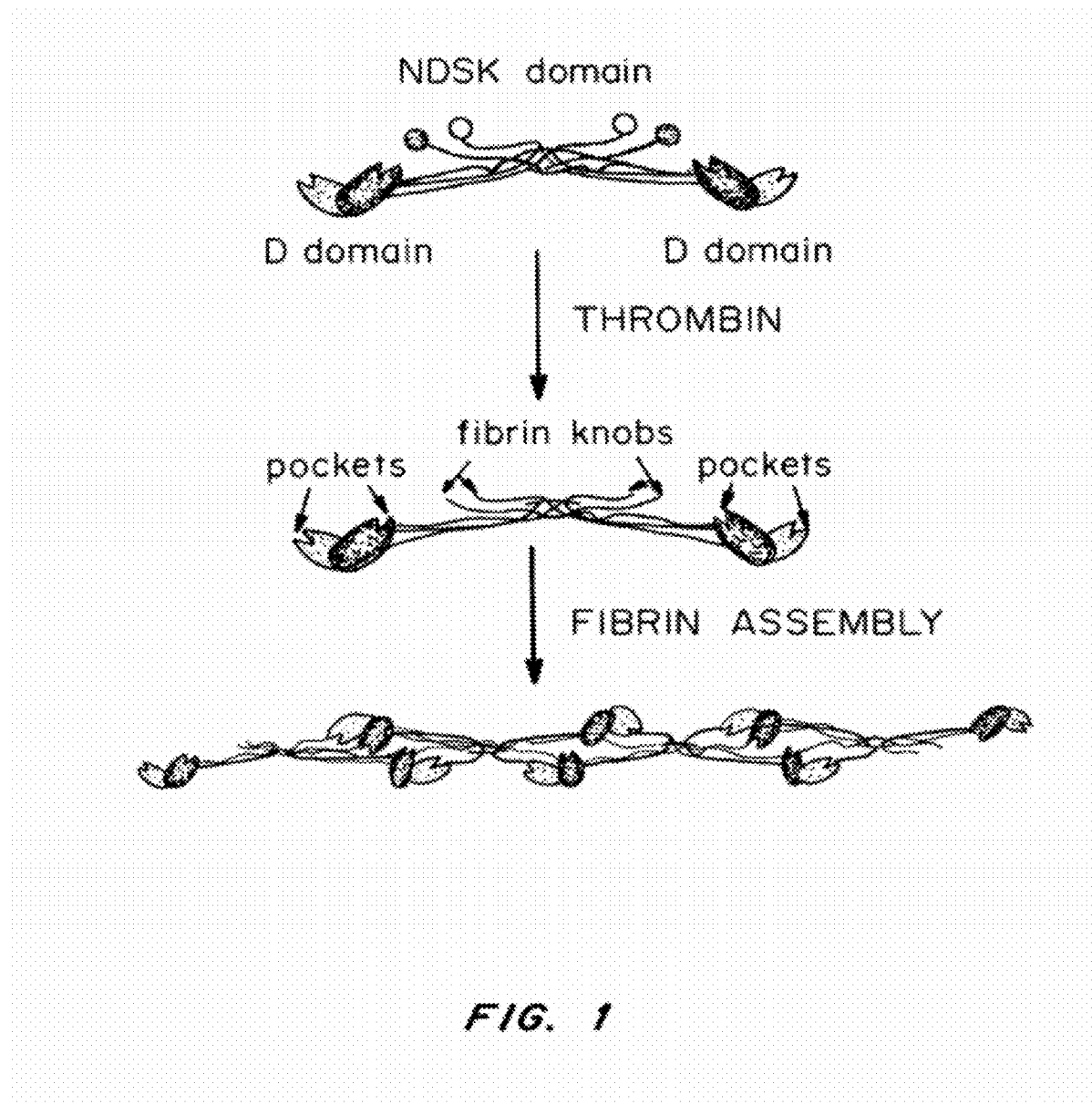
FIG. 1 is a schematic showing fibrinogen and its activation. The activation of fibrinogen (top) by thrombin exposes fibrin knobs in the NDSK domain that bind to complementary pockets in the D domain of the molecule (middle). Such knob:pocket interactions are key in the assembly of fibrin protofibrils (bottom) in fibrin network formation.

Compositions and methods are provided for integrating substances, such as bioactive agents or inert polymers, into fibrin. This process takes advantage of the native knob:pocket interactions involved in fibrinogen assembly into fibrin polymers.

I. DEFINITIONS

Unless otherwise noted, technical terms are used according to conventional usage. Definitions of common terms in molecular biology may be found in Lewin, Genes VII, published by Oxford University Press, 2000; Kendrew et al. (eds.), The Encyclopedia of Molecular Biology, published by Wiley-Interscience, 1999; and Robert A. Meyers (ed.), Molecular Biology and Biotechnology, a Comprehensive Desk Reference, published by VCH Publishers, Inc., 1995; Sambrook and Russell. (2001) Molecular Cloning: A Laboratory Manual 3rd. edition, Cold Spring Harbor Laboratory Press.

To facilitate understanding of the disclosure, the following definitions are provided:

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid. Conservative substitutions and deletions are described below.

The term "residue" or "position," with respect to an amino acid residue in a polypeptide, refers to a number corresponding to the numerical place that residue holds in the polypeptide. By convention, residues are counted from the amino terminus to the carboxyl terminus of the polypeptide. Thus, position 326 of human eNOS would be the 326th residue from the amino terminus of the eNOS protein sequence.

The term "nucleic acid" refers to a natural or synthetic molecule having a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

An "isolated" nucleic acid molecule or polynucleotide is a nucleic acid molecule that is identified and separated from at least one substance with which it is ordinarily associated in the natural source. The isolated nucleic can be, for example, free of association with all components with which it is naturally associated. An isolated nucleic acid molecule is other than in the form or setting in which it is found in nature.

The term "vector" refers to a nucleic acid sequence capable of transporting into a cell another nucleic acid to which the vector sequence has been linked. The vectors can be expression vectors.

The term "expression vector" refers to a vector that includes one or more expression control sequences.

The term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

The term "promoter" refers to a regulatory nucleic acid sequence, typically located upstream (5') of a gene or protein coding sequence that, in conjunction with various elements, is responsible for regulating the expression of the gene or protein coding sequence.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The term "cell" refers to individual cells, cell lines, primary culture, or cultures derived from such cells unless specifically indicated. A "culture" refers to a composition having isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

The term "endogenous" with regard to a nucleic acid refers to nucleic acids normally present in the host.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "nucleic acid" may be used to refer to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 5, 10, 20, 30, 40, 50, 60, 70, 80, 90, 100%, or any amount of reduction in between as compared to native or control levels. With regard to eNOS, the reduction of activity refers to β-actin binding or NO production.

"Promote," "promotion," and "promoting" refer to an increase in an activity, response, condition, disease, or other biological parameter. This can include, but is not limited to, the initiation of the activity, response, condition, or disease. This may also include, for example, a 10% increase in the activity, response, condition, or disease as compared to the native or control level. Thus, the reduction can be a 5, 10, 20, 30, 40, 50, 60, 70, 80, 90, 100%, or any amount of increase in between as compared to native or control levels.

By "treat" or "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "therapeutically effective" means that the amount of the composition used is of sufficient quantity to ameliorate one or more causes or symptoms of a disease or disorder. Such amelioration only requires a reduction or alteration, not necessarily elimination.

By "pharmaceutically acceptable" is meant a material that is not biologically or otherwise undesirable, i.e., the material may be administered to a subject, along with the disclosed polypeptide, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

II. FIBRIN KNOB PEPTIDES

Fibrinogen is a symmetrical, rod-shaped molecule having two sets of three polypeptides (Aα-, Bβ-, and γ-chains) assembled lengthwise and crosslinked at their N-termini via multiple disulfide bonds, forming a single central N-terminal disulfide knot (NDSK) and two distal globular domains (D domains). During the activation of fibrinogen to fibrin monomer, the serine protease thrombin cleaves the N-termini of both the Aα- and Bβ-chains, exposing new cryptic residues (i.e. knob-A and knob-B) in the NDSK domain that bind to complementary sites (i.e. a- and b-pockets) near the two distal C-termini of the γ- and Bβ-chains within the D domains (FIG. 1). These non-covalent knob:pocket interactions lead to the assembly of fibrin protofibrils that make up the fibrin network (Lord S T. Curr Opin Hematol 2007, 14(3):236-241; Weisel J W. J Thromb Haemost 2007, 5(12):2340-2343). These networks are further stabilized by activated transglutaminase factor XIII (factor XIIIa) that covalently crosslinks γ- and α-chains of adjacent fibrin monomers within the protofibril (Ariens R A, et al. Blood 2002, 100(3):743-754).

Short synthetic peptides modeled after the fibrin knob sequences bind to the C-terminal pockets of fibrin(ogen). Specifically, various tetrapeptides have significantly different affinities for fibrin(ogen) pockets, with GPRP (SEQ ID NO:1; A-knob tetrapeptide mimetic) having the greatest affinity followed by GPRV (SEQ ID NO:2; native A-knob tetrapeptide), then GHRP (SEQ ID NO:3; native B-knob tetrapeptide). Therefore, an affinity-based scheme stemming from an inherent non-covalent interaction such as the knob:pocket interaction can retain proteins within fibrin matrices without intermediary molecules or enzymes, like factor XIIIa.

Compositions and methods for conjugating tetrapeptide fibrin knob sequences to substances, such as bioactive agents or inert polymers, are therefore disclosed to endow fibrin-binding capacities to those substances via knob:pocket interactions.

The integrin-binding fibronectin $9^{th}$ and $10^{th}$ type III repeats (FnIII$_{9-10}$) are amenable to recombinant protein production, do not bind fibrin(ogen), and have previously been shown to induce osteogenic differentiation in mesenchymal stem cells (Petrie T A, et al. Biomaterials 2006, 27(31):5459-5470; Martino M M, et al. Biomaterials 2009, 30(6):1089-1097). Using this protein domain as a model protein, knob-protein fusions are shown to bind stably to fibrin(ogen) via specific knob:pocket interactions. Retention of these fusion proteins within fibrin matrices was evaluated through the use of ELISA-based protein release assays as well as real-time confocal imaging of perfused fibrin matrices. These data demonstrate the ability to incorporate substances into fibrin polymers using fibrin knob peptides.

A. Fibrin Knobs

Peptides and fusion proteins containing fibrin knobs are disclosed. These peptides preferably have knobs that bind fibrin(ogen) pockets at the N-terminus of the peptide. Therefore, peptides and fusion proteins are provided that contain an N-terminal peptide sequence, such as a tetrapeptide, that binds fibrin(ogen) pockets.

The term "fibrin knob peptide" is used herein to refer to a peptide sequence of at least 4 amino acids that binds directly to a fibrin(ogen) pocket. Preferably, the fibrin knob peptide binds the fibrin(ogen) pocket with an affinity at least as strong as that of GHRP (SEQ ID NO:3).

The fibrin knob peptide can have the tetrapeptide amino acid sequences GPRP (SEQ ID NO:1; A-knob tetrapeptide mimetic), GPRV (SEQ ID NO:2; native A-knob tetrapeptide), or GHRP (SEQ ID NO:3; native B-knob tetrapeptide).

The fibrin knob peptide can have the amino acid sequence GXRX (SEQ ID NO: 20), where X is any amino acid. The fibrin knob peptide can have the amino acid sequence $GX_1RX_2$ (SEQ ID NO: 21), where "$X_1$" is Pro or His, where $X_2$ is Pro or Val. The fibrin knob peptide can include 4, 5, 6, 7, 8, 9, 10, 11, 12, or more amino an amino acids.

The peptide can also have additional amino acids that help stabilize the backbone of the amino acids that binds the fibrin pocket. The fibrin knob peptide can therefore have the amino acid sequence GPRPX (SEQ ID NO:22), GPRVX (SEQ ID NO:23), GPRPXX (SEQ ID NO:24), GPRVXX (SEQ ID NO:25), GPRPXXX (SEQ ID NO:26), GPRVXXX (SEQ ID NO:27), GPRPXXXX (SEQ ID NO:28), or GPRVXXXX (SEQ ID NO:29), where X is any amino acid. The fibrin knob peptide can have the amino acid sequence GPRXXX (SEQ ID NO:30), where X is any amino acid. The fibrin knob peptide can therefore have the amino acid sequence GPRPAA (SEQ ID NO:10). In preferred embodiments, the fibrin knob peptide has the amino acid sequence GPRPFXX (SEQ ID NO:31) or GPRVFXX (SEQ ID NO:32), where X is any amino acid.

The peptide can also have a C-terminal amino acid, such as for example cysteine or lysine, that enables subsequent chemical reactions with other agents to produce C-terminal conjugates. Therefore, in some embodiments, the C-terminal amino acid of the peptide is a cysteine. Therefore, in some embodiments, the C-terminal amino acid of the peptide is a lysine. For example, the fibrin knob peptide can have the amino acid sequence GPRPAAC (SEQ ID NO:4), GPRPFPAC (SEQ ID NO:5), GPRPPERC (SEQ ID NO:6), GPRVVERC (SEQ ID NO:7), GPRVVAAC (SEQ ID NO:8), or GPSPAAC (SEQ ID NO:9).

The fibrin knob peptide selected can depend on the affinity to fibrin that is desired. For example, where a high affinity to fibrin is desired, the fibrin knob peptide can have the amino acid sequence GPRPFPAC (SEQ ID NO:5).

1. Variants

Also disclosed are functional variants of the disclosed fibrin knob peptides that can bind fibrin pockets. The term "variant" refers to an amino acid or peptide sequence having conservative and non-conservative amino acid substitutions, insertions or deletions. Substitutions, deletions, insertions or any combination thereof may be combined to arrive at a final construct. "Functional variants" of the disclosed fibrin knob peptides include those that bind fibrin pockets.

Insertions include amino and/or carboxyl terminal fusions as well as intra-sequence insertions of single or multiple amino acid residues. Insertions ordinarily will be smaller insertions than those of amino or carboxyl terminal fusions, for example, on the order of one to four residues.

Deletions are characterized by the removal of one or more amino acid residues from the protein sequence. Thus, the polypeptide can have 1, 2, 3, or 4 deletions from the disclosed reference sequence. These variants ordinarily are prepared by site specific mutagenesis of nucleotides in the DNA encoding the protein, thereby producing DNA encoding the variant, and thereafter expressing the DNA in recombinant cell culture.

Substitutional variants are those in which at least one residue has been removed and a different residue inserted in its place. Thus, the polypeptide can also have 1, 2, 3, or 4 substitutions within the disclosed reference sequence. Techniques for making substitution mutations at predetermined sites in DNA having a known sequence are well known, for example M13 primer mutagenesis and PCR mutagenesis.

a. Conservative Substitutions

In certain embodiments, the protein variant has a conservative amino acid substitution in the disclosed reference sequence. The replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr.

In contrast, the substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

b. Percent Identity

It is understood that one way to define the variants and derivatives of the disclosed polypeptides disclosed herein is through defining the variants and derivatives in terms of homology/identity to specific known sequences. Thus, disclosed are variants of these and other disclosed proteins. For example, disclosed are polypeptides having at least, 5, 6, or 7 of the 8 amino acids in a polypeptide sequence disclosed herein. Also disclosed are polypeptides having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to a polypeptide sequence disclosed herein.

It is understood that the description of conservative mutations and sequence identity can be combined together in any combination, such as embodiments that have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to a particular sequence wherein the variants are conservative mutations.

c. Analogs and Mimetics

It is understood that there are numerous amino acid and peptide analogs which can be incorporated into the disclosed compositions. Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

Thus, also disclosed is a peptidomimetic of the disclosed polypeptides that can bind fibrin pockets. The term "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence are described, for example, in U.S. Pat. Nos. 5,631,280; 5,612,895; and 5,579,250. Use of peptidomimetics can involve the incorporation of a non-amino acid residue with non-amide linkages at a given position. One embodiment can be a peptidomimetic wherein the compound has a bond, a peptide backbone or an amino acid component replaced with a suitable mimic.

Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

There are also numerous D amino acids or amino acids which have a different functional substituent than natural amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs). D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides.

d. Modified Amino Acid Linkages

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, $CH(OH)CH_2$—, and —$CHH_2SO$— (these and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications; Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH $H_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—COCH$_2$—); Szelke et al. European Appln, EP 45665 CA (1982): 97:39405 (1982) (—CH(OH)CH$_2$—); Holladay et al. Tetrahedron. Lett 24:4401-4404 (1983) (—C(OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Cysteine residues can also be used to cyclize or attach two or more peptides together. This can be beneficial to constrain peptides into particular conformations. (Rizo and Gierasch Ann. Rev. Biochem. 61:387 (1992), incorporated herein by reference).

B. Conjugates

A conjugate of a substance, such as a peptide, protein, or polymer, to the C-terminus of a knob peptide is also disclosed. Where the substance is a protein, the conjugate is preferably a fusion protein. Therefore, a fusion protein is disclosed that has a knob peptide at the N-terminus.

For example, a fusion protein is disclosed having the formula:

Fkp-P, where "Fkp" is a fibrin knob peptide disclosed herein and "P" is a peptide or protein, such as a bioactive protein or an inert carrier. The Fkp can be GXXX (SEQ ID NO:20), where "X" is any amino acid. The Fkp can be GX$_1$RX$_2$ (SEQ ID NO:21), where "X$_1$" is Pro or His, where X$_2$ is Pro or Val. Therefore, the Fkp can be GPRP (SEQ ID NO:1), GPRV (SEQ ID NO:2), or GHRP (SEQ ID NO:3), wherein "P" is a peptide or protein.

The dashes in the formula can represent either a direct link between the N-terminus of the bioactive peptide and the fibrin knob, additional amino acids in the knob peptide, or a linker joining the protein and peptide. For example, the Fkp can be GPRPAAC (SEQ ID NO:4), GPRPFPAC (SEQ ID NO:5), GPRPPERC (SEQ ID NO:6), GPRVVERC (SEQ ID NO:7), GPRVVAAC (SEQ ID NO:8), GPSPAAC (SEQ ID NO:9), or GPRPAA (SEQ ID NO:10).

As noted above, a fusion protein was generated for proof of principle using the integrin-binding fibronectin 9$^{th}$ and 10$^{th}$ type III repeats (FnIII$_{9-10}$). This fusion protein is designated Gxxx-FnIII$_{9-10}$ (SEQ ID NO:20), which included GPRP-FnIII$_{9-10}$ (SEQ ID NO:1), GPRV-FnIII$_{9-10}$ (SEQ ID NO:2), and GHRP-FnIII$_{9-10}$ (SEQ ID NO:3).

The formula also includes additional moieties at the C-terminus of the fusion protein. For example, a C-terminal cysteine can be added to the fusion protein. For example, a fusion protein containing FnIII$_{9-10}$ and a C-terminal cysteine was produced and is designated Gxxx-FnIII$_{9-10}$-C (SEQ ID NO:20), which includes GPRP-FnIII$_{9-10}$-C (SEQ ID NO:2).

This C-terminal cysteine can be used to conjugate other moieties on the C-terminus. For example, the fusion protein can be conjugated via the sulfhydryl group of the C-terminal cysteine to maleimide-functionalized biotin. For example, a fusion protein containing FnIII$_{9-10}$ and a C-terminal biotin was produced and is designated Gxxx-FnIII$_{9-10}$-biotin (SEQ ID NO:20), which includes GPRP-FnIII$_{9-10}$-biotin (SEQ ID NO:2).

Similarly, the fusion protein can be labeled with carboxylic acid terminated label. For example, a fusion protein containing FnIII$_{9-10}$ and a C-terminal Alexa Fluor-555 or Alexa Fluor-633 was produced. A label can be used, for example, to detect fibrin in a subject. As used herein, a label can include a fluorescent dye, a radioactive isotope, a member of a binding pair, such as biotin/streptavidin, a metal (e.g., gold), or an epitope tag that can specifically interact with a molecule that can be detected, such as by producing a colored substrate or fluorescence.

1. Bioactive Proteins or Domains

Fibrin knob peptides can be conjugated to proteins or bioactive peptide domains. For example, the protein/peptide can be a therapeutic agent. The disclosed design for a fibrin-based therapeutic delivery system simplifies the mode of therapeutic incorporation by coupling, at the genetic level, the elements of fibrin knob that display fibrin-binding capacity and drive polymer formation and a deliverable protein/peptide species. The advantage of this design is that the deliverable protein species can be incorporated prior to the initiation of polymer formation and without additional steps or reagents. The capacity to bind the polymerization pocket(s) of fibrinogen also allows for the potential to develop technologies that modify the characteristics of the polymer if added in appropriate stoichiometries.

a. Growth Factors

Fibrin knob peptides can be conjugated to a growth factor. For example, the growth factor can be a vascular endothelial growth factor, platelet-derived growth factor, fibroblast growth factor, transforming growth factor-beta, insulin-like growth factor, parathyroid hormone, angiopoietin, thrombopoietin, connective tissue growth factor, nerve growth factor, neurotrophin, or epidermal growth factor.

Some of the growth factors, such as the fibroblast growth factors, are monomeric, and these can be incorporated directly and without complexity as domains in a fusion protein with fibrin knob peptides. Other growth factors, such as vascular endothelial growth factor, are dimeric. In such cases, it may be necessary to incorporate one monomer unit as a domain in the fusion protein, and then co-express an additional monomer of the growth factor as a soluble protein o that this monomer will dimerize with the monomer in the fusion protein. This could thus involve expressing both the monomer and the monomer-containing fusion protein, either simultaneously or sequentially.

In some embodiments, the fusion protein contains knob peptides and full length growth factors. In other embodiments, the fusion protein contains knob peptides and a bioactive fragment of the growth factor, such as the receptor-binding domain of the growth factor.

b. Cytokines and Chemokines

Fibrin knob peptides can be conjugated to cytokines or chemokines. Just as growth factors are powerful morphogens, chemokines and cytokines are powerful cellular regulators and morphogens. These include the interleukins, platelet activating factors, the CCR molecules, the CXC molecules, and many other families of proteins. Incorporation of these molecules can be carried out as for growth factors.

c. Adhesion Domains

Fibrin knob peptides can be conjugated to adhesion domains. Many extracellular matrix molecules and matricellular signal through their adhesion domains, including collagens, laminin, fibronectin, vitronectin, thrombospondins, L1, SPARC family members, elastin, ostopontin, the CCN family, ICAMs, CAMs, dystrophin, dystroglyan, proteoglycans, and so forth. The domains of these proteins that bind to the cell adhesion receptors on cells can often be localized to smaller domains of these proteins.

An illustrative example is fibronectin, in which the 9$^{th}$ and 10$^{th}$ type-III repeat domains contain two cell-binding domains that operate alone or in synchrony, namely an RDG site and a PHSRN (SEQ ID NO:37) site. Therefore, in this case, fibrin knobs can be conjugated to a short peptide comprising the sequence RGD, a short peptide comprising the sequence PHSRN (SEQ ID NO:37), the 9$^{th}$ type-III domain itself, the 10$^{th}$ type-III domain itself, or both the 9$^{th}$ and the 10$^{th}$ type-III domains. Most powerfully, whole protein domains can be used, allowing the fullness of their evolutionarily-determined structure to be incorporated into the fibrinogen variant. These adhesion domains can be useful for incorporating migration-inducing, angiogenic, and more generally morphogenetic character into fibrin gels formed including the adhesion domain-containing fibrinogen mutant.

d. Antiadhesion Domains

Fibrin knob peptides can be conjugated to anti-adhesion domains. Some proteins function as negative regulators of cell adhesion, repelling rather than inducing cell adhesions. These molecules include domains of thrombospondin, such as the SPAC domain. Incorporation of these molecules can be carried out as for the adhesion proteins. They can be useful in preventing scar formation, in preventing cellular migration and infiltration.

e. Immunomodulatory Domains

Fibrin knob peptides can be conjugated to immunomodulatory domains. Some proteins function as immunostimulatory and immunomodulatory molecules. One example is flagellin, a domain of which is known to bind to members of the toll-like receptor family and activate maturation of dendritic cells, leading to more effective antigen presentation and maturation of immune responses. In this case, either the whole protein flagellin or domains of flagellin can be conjugated to fibrin knob peptides. Other proteins of interest include bacterial coat proteins, mannose receptor ligands, and viral coat proteins.

f. Protein-Binding Domains

Fibrin knob peptides can be conjugated to protein-binding domains. Many proteins have evolved binding domains for other proteins. For example, members of the transforming growth factor beta family bind to extracellular matrix proteins such as members of the collagen family. In this case, such domains of collagen can be conjugated to fibrin knob peptides. Alternatively, protein-binding domains could be identified by computational methods or by combinatorial methods conjugation to peptide knob peptides. As a specific example of protein-binding domains, proteins that bind to the extracellular matrix molecules are of particular interest in regenerative medicine, including fibronectin, which binds collagen and thrombospondin; and nidogen, which binds elastins and laminins.

g. Nucleic Acid-Binding Domain

Fibrin knob peptides can be conjugated to a nucleic acid-binding domain. Many proteins contain DNA-binding and RNA-binding domains. Such proteins include transcription factors and histone proteins. Moreover, DNA-binding domains can be identified computationally or combinatorially, and oligomers and polymers of lyine, argine, and histidine also bind DNA. Such domains can be conjugated to fibrin knob peptides, for the purpose of binding do DNA in gene delivery, antisense oligonucleotide delivery, si-RNA delivery, and so forth.

h. Polysaccharide-Binding Domains

Fibrin knob peptides n polysaccharide-binding domains, e.g. those having affinity for heparin, heparan sulfate, chondrointin sulfate, dermatan sulfate, and so forth. These domains may be useful to immobilize polysaccharides within fibrin matrices, either because of the active character of the polysaccharide or due to its ability to bind to other proteins.

i. Virus-Binding Domains

Fibrin knob peptides can be conjugated to virus-binding domains. Some proteins bind to viral coat proteins, e.g. the coxsackie-adenoviral receptor. Incorporation of such virus-binding domains can be accomplished for better retention and delivery of viral vectors in gene delivery.

j. Cytotoxic Domains

Fibrin knob peptides can be conjugated to cytotoxic domains. Some proteins bind to cell-surface receptors and induce cell death via apoptosis. These proteins include the FAS ligand. Incorporation of such domains can be accomplished for prevention of scar formation, cell infiltration and cell migration, and can be useful in the local treatment of tumors.

k. Enzymatically Active Domains

Fibrin knob peptides can be conjugated to enzymatically active domains. Some proteins have enzymatic activity, such as proteases and transglutaminases. These proteins can be incorporated to provide a long-term chemically reactive character to the resulting fibrin gel, including the ability to locally convert pro-drugs to active drugs within the fibrin matrix containing such an enzyme as an X domain in a fibrinogen fusion protein. Proteases incorporated as an X domain may influence fibrin degradation rate, and transglutaminases may incorporate other exogenous proteins within the fibrin network or also influence degradation rate.

l. Protease Inhibitors

Fibrin knob peptides can be conjugated to protease inhibitors. Some proteins inhibit proteases, and these can be incorporated to influence degradation rate of the resulting fibrin network or of other matrix proteins co-incorporated within the fibrin matrix. For example, the fibrin knob peptides can be conjugated to aprotinin.

m. Serum Proteins

Fibrin knob peptides can be conjugated to serum proteins. Some proteins have little enzymatic, inflammatory, or immunogenic activity and may be used to enhance the pharmacokinetics such that the fusion protein displays extended circulation/residence times. These are also useful as inert carriers as discussed below.

3. Environmentally-Responsive Elements

Rapid polymerization is ideal in the native system (i.e. in the blood stream) where the rate-limiting step in this process is the generation of active thrombin. However, in the exogenous system used by health care professionals, which utilizes purified fibrinogen and thrombin, rapid polymerization complicates the delivery of the polymer in situ. Specialized syringe delivery systems have been developed to minimize this problem, yet without adequate training and practice this syringe system is rendered less effective. In addition to problems arising from polymerization in the delivery system, the rapid polymerization of fibrin leads to problems in reproducibility in the polymer application and an inadequate working time. This lack of reproducibility significantly affects the safety and efficacy of the system and the short working-time limits the number of possible applications the polymer can be used for as well as the ease of use.

However, conjugating fibrin knob peptides to environmentally-responsive elements can be used to decouple fibrin polymerization from thrombin activation and instead couple it to more application specific stimuli. This can greatly improve the utility and reproducibility of the system.

The environmentally-responsive element conjugated to fibrin knobs can be a phase transition polymer. Phase transition polymers register a distinctive change in properties upon a modest change in environmental conditions, such as temperature or pH. In the context of biomedical applications that deal with aqueous systems, the phase transition commonly refers to a volume-phase transition due to changes in the salvation state, with the polymer quickly transitioning from a soluble/expanded state to an insoluble/collapsed state depending on the environmental condition. This change in solvation state reflects competing inter- and intra-molecular hydrogen bonding properties of the polymer with a solubilization by water and is usually reversible. Additionally, the point of transition can be fine-tuned to the researchers' needs by directly altering the polymer composition, or changing auxiliary factors such as salt concentration, surfactants, or co-solvents.

Preferably, the phase transition polymer is a thermo-responsive polymer. Thermo-responsive polymers that become insoluble upon heating have a lower critical solution temperature (LCST), whereas polymers that become soluble upon heating have an upper critical solution temperature (UCST). Polymers that exhibit UCST behavior in the biomedical context are rare. Typical LCST polymers include poly-N-isopropylacrylamide (PNIPAM, LCST ~32° C.), poly-methylvinylether (PMVE, LCST ~40° C.) and poly-N-vinylcaprolactam (PVCa, LCST ~30° C.). In particular, the biocompatibility and position of the LCST for PNIPAM has made it a well-studied polymer for use in drug delivery and tissue engineering. Several groups have studied the loading and release kinetics of peptides from PNIPAM at different temperatures, indicating the feasibility of the system for use as an on-off switch for the in vivo delivery of peptides.

Certain polypeptides also exhibit LCST behavior, including elastin-like polypeptides (ELPs). However, unlike LCST polymers, ELPs have the additional property of being able to self-assemble into ordered arrays of β-spirals above their transition temperature. This phenomenon is separately referred to as inverse temperature transition. The use of recombinant polypeptides is particularly advantageous for several reasons. First, a monodispersed product is produced, allowing the accurate and reproducible characterization of its phase transition properties. Second, varying the amino acid sequence of the recombinant plasmid, through recursive directional ligation can easily generate polymers of the desired thermal characteristics. Third, ELPs are well tolerated by the body and their degradation products are naturally occurring amino acids.

a. Elastin-Like Polypeptides

Therefore, the fibrin knob peptides can be conjugated to elastin-like polypeptides (ELPs) to produce peptides with temperature sensitive binding to fibrin(ogen). ELPs are thermo-responsive polymers containing repeats of the pentapeptide sequence VPGXG (SEQ ID NO:38), where X is any amino acid with the exception of proline. A Pro substitution at the fourth position destroys the inverse phase transition. This sequence is derived from the characteristic repeat motif found in exon 20 of native mammalian elastic protein, elastin. The soluble precursor to elastin, the 70 kDa tropoelastin, has been shown to undergo a reversible phase separation where the protein self-aggregates under increasing temperature. It has been suggested that this phenomenon (known as coacervation) is necessary, and perhaps sufficient, for the in vivo assembly of tropoelastin into the crosslinked polymeric network that makes up the insoluble extracellular matrix called elastin. Coacervation may assists in the alignment of lysine crosslinking sites within the molecule. Evidence to this effect is that short elastin polypeptides containing hydrophobic domain-generating exons 20 and 24 with interspersed crosslinking domain-generating exons 21 and 23 not only undergo coacervation but are capable of forming insoluble crosslinked elastin-like matrix.

The coacervation of ELPs, which can be determined spectra-photometrically by monitoring solution turbidity at 350 nm, occurs typically over a 2° C. range, with the transition temperature ($T_t$) defined as the temperature at 50% maximal turbidity. The $T_t$ is a function of the sequence, the identity and mole fraction of guest residues at the fourth position of the ELP and the chain length. In general, increasing hydrophobicity of the fourth amino acid in SEQ ID NO:38 and chain length both reduce $T_t$. The model ELP places Val at the fourth position (VPGVG, SEQ ID NO:39). ELPs with guest residues having simple aliphatic side chains produce a consistent and acute thermal response under most experimental conditions. Complex ELPs use functionalized guest residues that can act as cross-linkers and also affect the transitioning properties of the polymer. For example, ELPs with ionizable guest residues can display different $T_t$ depending on whether they are present in the protonated or deprotonated state. In a like manner, the genetic fusion of an ELP to a protein alters the $T_t$ presumably by altering the hydrophobicity of the complex. Despite the altered $T_t$, one of the most promising uses of ELPs is to facilitate the purification schemes of recombinant proteins. In addition to utilization for protein purification, ELPs have been designed and tested as macromolecular carriers for thermal targeting of therapeutics to various tissues, most notably solid tumors, but also intra-articular spaces among others. ELPs have also been successfully used as temperature sensitive switches for the binding and release of molecules in biosensors. This technology is made possible due to the physical force that can be generated by ELPs as a result of the phase transition.

4. Inert Carriers

Fibrin knob peptides can be conjugated to inert carriers to block the self-binding pockets of fibrinogen (and fibrin monomers). Through saturation with this conjugate, one can effectively "cap" the growing polymer, which can decrease the fibrotic response. A conjugate of a fibrin knob peptide and an inert carrier can bind to fibrinogen and fibrin monomers and prevent self-binding to the polymerization pocket of fibrinogen. This interaction can inhibit fibrin formation in a dose dependent fashion. Consequently, this conjugate can be used to diminish the formation of fibrin following injuries, such as wounds, surgical abdominal cavity abrasions (which lead to postsurgical adhesions), or pulmonary damage, and thus limit the extent of scar formation and pulmonary fibrosis.

The conjugate is predicted to function by two mechanisms, first by blocking fibrin formation and second by increasing the sensitivity of the polymer that may form to enzymatic degradation through its incorporation.

a. Human Serum Albumin

The inert carrier can be human serum albumin (HSA). Due to the prolonged circulation half-life and low immunogenicity, HSA can be used for clinical molecular delivery. HSA has been used as the protein component in several protein polymer systems. The low bioreactivity to the protein makes it an ideal protein for in-vivo applications. Although polymorphisms in the DNA do exist, the primary sequence is known. rHSA has been used to produce genetic fusions to protein therapeutics for increasing their circulation times while limiting their immunogenicity.

b. Polymers

The inert carrier can be a polymer, such as polyethylene glycol. PEGylation, or the covalent attachment of PEG to molecules of interest, is an enabling technology that is routinely used to improve the physiochemical characteristics of therapeutic drugs and proteins. PEGylation reduces the immunogenicity of proteins while preserving their enzymatic activity. PEGylation reduces the immunogenicity of molecules by reducing their accessibility to antibodies and proteolytic enzymes through steric hindrance imparted by the mobile polymer chains. The hydrophilic PEG chains also impart solubility and increase the hydrodynamic radius of the parent molecule, thus reducing kidney clearance and increasing the blood circulation time of small proteins or peptides.

High quality PEGs of various conjugation chemistries and structures are now available commercially (Laysan Bio, Arab, Ala.; JenKem Technology USA, Allen, Tex.; NOF Corporation, Tokyo, Japan). Conjugation via the sulfhydryl group of cysteine is one of the most specific methods of in vitro protein modification due to the lower abundance of cysteine residues as compared to amine-containing lysine residues. Use of this strategy in PEGylation has been gaining popularity as genetic engineering and recombinant protein production allows for the introduction of deliberately placed cysteine residues for site-directed conjugation. [58-60] This is particularly useful when amino groups are involved in protein function since amine-mediated conjugation chemistries might inadvertently target the active site of the protein, resulting in an inactive conjugate. In particular, the sulfhydryl-maleimide reaction can be carried out efficiently under mild conditions so as to preserve protein/peptide function.

Therefore, Fibrin knobs peptides containing cysteine residues at the C-terminus can be conjugated to polyethylene glycol by a sulfhydryl-maleimide reaction. PEGylation in this context provides a convenient and reproducible means of generating fibrin-binding PEGs with different peptide configurations (e.g. mono-, bi-, multi-valent) on a single inert polymer backbone enabling the regulation of fibrin formation and polymer structure.

5. Other Conjugates?

Fibrin knob peptides can be conjugated to imaging conjugates that allow one to detect fibrin polymers in a subject. For example, the fibrin knob peptides can be conjugated to a fluorophore. Fluorophores are compounds or molecules that luminesce. Typically fluorophores absorb electromagnetic energy at one wavelength and emit electromagnetic energy at a second wavelength.

Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP(Y66H); Blue Fluorescent Protein; BFP/GFP FRET; Bimane; Bisbenzemide; Bisbenzimide (HO-ECHST®); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 GENEBLAZER®); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DilC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP;

EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyde Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GENEBLAZER®; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; HOECHST® 33258; HOECHST® 33342; HOECHST® 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1;YOYO-3; Sybr Green; Thiazole orange (interchelating dyes); semiconductor nanoparticles such as quantum dots; or caged fluorophore (which can be activated with light or other electromagnetic energy source), or a combination thereof.

In some embodiments, the fibrin knob peptides can be conjugated to a radionuclide (radioisotope). Radionuclides include, but are not limited to, tritium, iodine-125, iodine-131, iodine-123, iodine-124, astatine-210, carbon-11, carbon-14, nitrogen-13, fluorine-18. The radionuclide can be attached to a linking group or bound by a chelating group, which is then attached to the peptide directly or by means of a linker. Radiolabeling techniques such as these are routinely used in the radiopharmaceutical industry can be used.

In some embodiments, the fibrin knob peptides can be conjugated to a contrast agent, such as those used for Magnetic resonance imaging (MRI), CT, PET, or ultrasound.

MRI contrast agents alter the relaxation times of tissues and body cavities where they are present. Depending on the image weighting, this can give a higher or lower signal. The most commonly used compounds for MRI contrast enhancement are gadolinium-based. Gadolinium-containing contrast agents include gadodiamide (OMNISCAN®), gadobenic acid (MULTIHANCE®), gadopentetic acid (MAGNEVIST®), gadoteridol (PROHANCE®), gadofosveset (ABLAVAR®), gadoversetamide (OPTIMARK®), gadoxetic acid (EOVIST®), gadobutrol, gadocoletic acid, gadodenterate, gadomelitol, gadopenamide, and gadoteric acid (DOTAREM®). Two types iron oxide contrast agents exist: Superparamagnetic Iron Oxide (SPIO) and Ultrasmall Superparamagnetic Iron Oxide (USPIO). These contrast agents consist of suspended colloids of iron oxide nanoparticles and when injected during imaging reduce the T2 signals of absorbing tissues. Available iron oxide contrast agents include Cliavist, COMBIDEX® (ferumoxtran-10), Endorem (FERIDEX IV®—ferumoxides injectable solution), Resovist, and Sinerem. Manganese chelates such as Mn-DPDP enhances the T1 signal.

Ultrasound contrast agents rely on the different ways in which sound waves are reflected from interfaces between substances. This may be the surface of a small air bubble or a more complex structure. Commercially available contrast media are gas-filled microbubbles that are administered intravenously to the systemic circulation. Microbubbles have a high degree of echogenicity, which is the ability of an object to reflect the ultrasound waves. The echogenicity difference between the gas in the microbubbles and the soft tissue surroundings of the body is immense. Thus, ultrasonic imaging using microbubble contrast agents enhances the ultrasound backscatter, or reflection of the ultrasound waves, to produce a unique sonogram with increased contrast due to the high echogenicity difference.

Therefore, in some embodiments, the fibrin knob peptides are conjugated to liposomes, micelles, or polymer nanopheres or microspheress. These agents can act as carriers of imaging elements, therapeutics, or a combination thereof.

C. Conjugation

The disclosed fibrin knob peptides can be conjugated to the disclosed substances, such as peptides, proteins, or polymers using standard methods known in the art. Where the substance is a peptide/protein that peptide/protein is preferably in a fusion protein with the fibrin knob peptides.

1. Fusion Proteins

Fusion proteins, also know as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics. Chimeric mutant proteins occur naturally when a large-scale mutation, typically a chromosomal translocation, creates a novel coding sequence containing parts of the coding sequences from two different genes.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins. This technique is often used for identification and purification of proteins, by fusing a GST protein, FLAG peptide, or a hexa-his peptide, which can be isolated using nickel or cobalt resins (affinity chromatography).

Alternatively, internal ribosome entry sites (IRES) elements can be used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (U.S. Pat. Nos. 5,925,565 and 5,935,819; PCT/US99/05781). IRES sequences are known in the art and include those from encephalomyocarditis virus (EMCV) (Ghattas, I. R. et al., Mol. Cell. Biol., 11:5848-5849 (1991); BiP protein (Macejak and Sarnow, Nature, 353:91 (1991)); the Antennapedia gene of drosophilia (exons d and e) [Oh et al., Genes & Development, 6:1643-1653 (1992)); those in polio virus [Pelletier and Sonenberg, Nature, 334:320325 (1988); see also Mountford and Smith, TIG, 11:179-184 (1985)).

2. Crosslinkers

The disclosed fibrin knob peptides can be conjugated to the disclosed substances, such as peptides, proteins, or polymers using crosslinkers. Protein crosslinkers that can be used to crosslink substances to the disclosed fibrin knob peptides are known in the art and are defined based on utility and structure and include DSS (Disuccinimidylsuberate), DSP (Dithiobis (succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulthsuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl)suberate), SMPB (Succinimdyl-4-(p-maleimidophenyl)butyrate), SULFO SMPB (Sulfo-succinimdyl-4-(p-maleimidophenyl)butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio)propionamido) hexanoate), SULFO NHS LC SPDP (Sulfosuccinimidyl-6-[3-(2-pyridyldithio)propionamido) hexanoate), SPDP (N-Succinimdyl-3-(2-pyridyldithio)propionate), NHS BROMOACETATE (N-Hydroxysuccinimidylbromoacetate), NHS IODOACETATE (N-Hydroxysuccinimidyliodoacetate), MPBH (4-(N-Maleimidophenyl)butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS(N-(epsilon-Maleimidocaproyloxy) sulfosuccinimide), EMCS(N-(epsilon-Maleimidocaproyloxy)succinimide), PMPI (N-(p-Maleimidophenyl) isocyanate), KMUH (N-(kappa-Maleimidoundecanoic acid)hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy)succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

3. Multivalent Conjugation

Two or more of the disclosed fibrin knob peptides can be conjugated together to form divalent or multivalent knob peptides where each of the fibrin knob peptides is at the N-terminus of its peptide chain. Thus, disclosed is a composition having the formula:

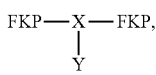

wherein FKP is a fibrin knob peptide, X is a linker, and Y is a substance disclosed herein for conjugation to a fibrin knob peptide, such as a peptide, protein, or polymer. Thus also disclosed is a composition having the formula:

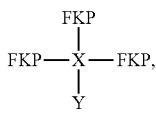

wherein FKP is a fibrin knob peptide, X is a linker, such as an amino acid linker, and Y is a substance disclosed herein for conjugation to a fibrin knob peptide, such as a peptide, protein, or polymer. Other such conjugations of fibrin knob peptides can be envisioned and are disclosed.

Thus, in some embodiments, the polypeptides are linked to form a dendrimer. Peptide dendrimers are branched, often highly branched, artificial proteins in which several peptide chains branch out from a dendritic core matrix that is built up through the propagation of, for example, a trifunctional amino acid, such as Lys. Originally conceived as Multiple Antigen Presentation System (MAPs) for vaccine development, these molecules are also useful for protein design.

The term "amino acid linker" refers to an amino acid sequences or insertion that can be used to connect or separate two distinct polypeptides or polypeptide fragments, wherein the linker does not otherwise contribute to the essential function of the composition.

D. Nucleic Acids Encoding Fibrin Knobs

Also disclosed are nucleic acids encoding the disclosed fibrin knob peptides and fusion proteins. Thus, disclosed are all nucleic acids, including degenerate nucleic acids, encoding the disclosed variants and derivatives of the protein sequences. While each particular nucleic acid sequence may not be written out, it is understood that each and every sequence is in fact disclosed and described through the disclosed protein sequence.

The nucleic acids that are delivered to cells typically contain expression control systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. Thus, also disclosed are nucleic acids encoding the disclosed polypeptides operably linked to an expression control sequence.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species can also be used.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell. Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and contains of about 400 bases. It is also preferred that the transcribed units contain other standard sequences alone or in combination with the above sequences improve expression from, or stability of, the construct.

A vector containing a nucleic acid encoding the disclosed polypeptides is also disclosed. In some embodiments the vector is derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens.

Cells containing one or more of the disclosed nucleic acids or vectors are also disclosed.

E. Fibrin Gels

The fibrin knob peptides can be used in the formation of fibrin polymer gels. Therefore, fibrin gels that contain fibrin knob peptides conjugated to a substance disclosed herein are provided. In a preferred embodiment, the fibrin polymer is a hydrogel. Hydrogels can exhibit dramatic effects of swelling or shrinking upon a stimulus. One such stimulus is movement or conformational change of biomolecules attached thereto. Another type of stimulus occurs when there is a change in pH in the environment in which the hydrogel is present. Such local pH change causes water and counter-ions to move in or out of the hydrogel and this induces swelling or shrinking of the hydrogel. Certain types of hydrogels undergo abrupt changes in volume in response to changes in pH, temperature, electric fields, saccharides, antigens and solvent composition, among others. Natural and artificial hydrogels can also be forced to shrink or swell by applying a bias on a metal electrode underneath or embedded in a hydrogel gel. Generally, a hydrogel can be prepared using many suitable monomers that, when polymerized, forms a hydrogel, such as acrylates, acrylamides, acetates, acrylic acids, vinyl alcohols, and glycols. Therefore, in some embodiments, the disclosed fibrin gel also contains at least one other monomer suitable for preparation of a hydrogel, such as acrylates, acrylamides, acetates, acrylic acids, vinyl alcohols, and glycols.

Fibrin polymers formed using the disclosed fibrin knob peptides, and conjugates thereof, have many clinical and bioengineering uses.

1. Haemostatic Glue and Wound Repair

Fibrin glue is currently being used clinically as an adjunct therapy to stem bleeding and to replace sutures in certain applications. Since the blood comes from a common pool, there is a risk of disease or prion transmission, even though the solutions are carefully processed and screened. To avoid this risk, researchers have developed systems to concentrate autologous fibrin glue from a patient's serum. To ensure that clotting occurs quickly and effectively, fibrin glues usually contain very high amounts of fibrinogen and thrombin. Current clinical uses include mesh fixation for inguinal hernia repair, severed sciatic nerve reattachment, stabilization of microsurgical anastomoses and skin graft adhesion. Using fibrin glue instead of sutures or staples enhances healing, minimizes scarring, eases application and in the case of hernia repair lowers the risk of nerve injury and postoperative neuralgia. Fibrin glue has also been shown to be effective in helping to anchor a deep brain stimulation electrode for the treatment of Parkinson's disease by acting as a protective layer between the dura and the methyl methacrylate bioglue that anchors the upper portion of the electrode to a stabilized titanium plate.

2. Drug Delivery

To provide injury repair, it is often desirable to locally deliver tissue-specific growth factors in a controlled manner. Fibrin is an appealing drug delivery vehicle because it can be injected where it gels in situ, it is degraded naturally and it stimulates the body's own wound healing response. By modifying the interaction between the growth factor and the fibrin scaffold, it is possible to vary the release profile from hours to weeks. The release rate is dependent upon the growth factor's initial concentration, diffusion rate and interaction with the matrix. Increasing the fibrinogen concentration would reduce the matrix pore size and thus retard the permeation of large solutes; however, increasing the concentration also retards endothelial cell migration and capillary formation.

3. Cell Delivery

Growth factor delivery is sufficient only if there are cells in the injury area capable of responding to the signals. When defects exceed a critical size, the local cell population is not sufficient to repair the injury and additional cells must be introduced. This is another application where fibrin has proven useful. Keratinocytes suspended in fibrin can be effective in reconstituting full thickness wounds, while skin fibroblast-coated fibrin microbeads can decrease the time for granulation tissue formation.

In plastic surgery, fat tissue transplantation is often required to create the desired look but this process can result in donor site deformity and also a gradual resorption of the transplanted tissue. Preadipocyte-seeded fibrin is possible alternative to autologous tissue transplantation. Injecting skeletal myoblasts in a fibrin scaffold into infarct regions of the heart can also improve cell survival and reduced the infarct scar. In this setting, the elastic modulus of the scaffold may be of particular significance since myocyte development does not proceed normally on materials with abnormally high stiffness.

4. Cell Differentiation and Tissue Engineering

Unlike a synthetic hydrogel, fibrin is not just a passive cell delivery matrix, but it binds specifically many growth factors as well as clot components, such as fibronectin, hyaluronic acid and von Willebrand factor. This bioactivity makes fibrin an attractive matrix for stem cell differentiation and tissue engineering. Fibrin has been effective as a scaffold for cartilage, cardiovascular and nervous tissue engineering. In cartilage tissue engineering, fibrin promotes glycosaminoglycan and collagen II while inhibiting collagen I deposition by primary or stem cell-derived chondrocytes. This trend is further enhanced by adding hyaluronic acid to the gel. To enhance the strength of the fibrin gel, a combination strategy can be employed whereby a highly porous synthetic polymer scaffold with appropriate mechanical properties is filled with chondrocytes suspended in a fibrin gel and this whole construct is implanted at the desired junction.

Severed peripheral nerve axons have some capacity to repair themselves but only if the defect is below a certain critical length. Fibrin sealant can be used for promoting nerve repair for a long time. To promote regeneration over longer lengths, channels filled with stimulatory signals can be used to bridge the severed ends. Synthetic polymer channels filled with fibrin can improve nerve repair and this is further enhanced if Schwann cells, which bind fibrin through $\alpha v \beta 8$ integrins and are required for healthy axon development, are suspended in the fibrin.

In addition to its central role in haemostasis, the fibrin clot also serves as a scaffold for angiogenesis. This makes fibrin uniquely suited for cardiovascular tissue engineering. As with cartilage and nerve regeneration, the best results are achieved when a synthetic scaffold with the desired mechanical properties is combined with a biologically tuned fibrin gel. One of the most advanced applications of a fibrin gel in cardiovascular engineering is the development of a moulding system to produce tricuspid heart valve replacements from fibrin, fibroblasts and smooth muscle myocytes.

5. Patterning

An increasingly common method to pattern tissue equivalents is by culturing them in a bioreactor. The bioreactors are individually designed to apply physiologically relevant forces to precondition the implants for their in vivo application. Grafts can be patterned by orienting the fibrin fibrils as they are polymerizing, which results in an anisotropic structure independent of applied force. This can be done by controlling the initiation sites, polymerizing fibrin under flow or in a high magnetic field or by electrospinning the protein on to a rotating target. Aligned fibrin has been shown to enhance neurite alignment and could be a useful filler for nerve guidance channels. Electrospinning has the added advantage of being able to design more advanced patterns, such as crosshatching, by manipulating the electric field. Control of solution conditions can also control fiber thickness and therefore permeability through the matrix.

F. Combination Therapies

A composition that contains the disclosed fibrin knob peptides, and conjugates thereof, and any known or newly discovered substance that can be administered to sites of fibrin formation are also disclosed.

For example, the provided composition(s) can further include one or more of classes of antibiotics (e.g., Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, Vancomycin).

The provided composition(s) can further include one or more of classes of steroids (e.g., Andranes (e.g., Testosterone).

The provided composition(s) can further include one or more of classes of narcotic and non-narcotic analgesics (e.g., Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine).

The provided composition(s) can further include one or more of classes of anti-inflammatory agents (e.g., Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Momiflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, Zomepirac Sodium).

The provided composition(s) can further include one or more of classes of anti-histaminic agents (e.g., Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

G. Pharmaceutical Compositions

The compositions disclosed can be used therapeutically in combination with a pharmaceutically acceptable excipient/carrier. Thus, also disclosed is a pharmaceutical composition having an effective amount of one or more polypeptides disclosed herein and a pharmaceutically acceptable excipient.

Pharmaceutical excipients are known to those skilled in the art. These most typically would be standard carriers for administration of drugs to humans, including solutions such as sterile water, saline, and buffered solutions at physiological pH. Pharmaceutical compositions may include carriers, thickeners, diluents, buffers, preservatives, surface active agents and the like in addition to the active agent. Pharmaceutical compositions may also include one or more active ingredients such as antimicrobial agents, anti-inflammatory agents, anesthetics, and the like.

Suitable pharmaceutical preparations include sterile aqueous or non-aqueous solutions, suspensions, and emulsions.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Suitable formulations include sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

III. METHODS

A. Method of Targeting an Agent to Fibrin

Methods are disclosed for targeting an agent, such as a peptide, molecule, or polymer, to fibrinogen or fibrin within a subject. For example, the method can involve administering to a subject a pharmaceutical composition that includes a fibrin knob peptide conjugated to a substance in a pharmaceutically acceptable carrier. As a result of this method, the substance conjugated to the fibrin knob peptide will bind via the fibrin knob peptide to fibrinogen or fibrin within the subject. This has many therapeutic and diagnostic uses.

1. Method of Diagnosing and Treating Clots

The ability of a fibrin knob peptide to bind and integrate into fibrin polymers indicates a use for these peptides to detect clots in a subject. Coagulation is an important part of hemostasis (the cessation of blood loss from a damaged vessel), wherein a damaged blood vessel wall is covered by a platelet and fibrin-containing clot to stop bleeding and begin repair of the damaged vessel.

Therefore, a method is provided for detecting fibrin-containing clots in a subject that involves administering to the subject a fibrin knob peptide conjugated to a label. In this method, the fibrin knob peptide conjugate will bind in a dose-dependent manner to the fibrin-containing clot and the label will subsequently concentrate at that location.

In some embodiments, the fibrin knob peptide is conjugated to an anti-coagulant to break up the clot upon binding.

2. Method of Diagnosing and Treating Fibrotic Disorders

Fibrosis and/or fibrotic disorders are characterized by excessive deposition of extracellular matrix (ECM) proteins, most notably members of the collagen family. The resultant dense ECM can restrict physiological functions, such as inhalation of the lung, or act to bind tissues which can restrict their motion and function, such as in the case of postoperative adhesions. There exist a multitude of pathologies that exhibit features of fibrosis and taken together these pathologies challenge all cancers as the leading cause of death in the U.S. Unfortunately there are no known cures of fibrosis and very few commercially available products that address the early stages of progression. The general lack of effective products may be due to fact that the exact mechanisms of each fibrotic response are unknown and likely differ. However, there do exist common pathways and regulators that have been determined and research is underway to target these common pathways. One such pathway is the persistence of fibrin. If normal fibrinolytic mechanisms are perturbed, resulting in the persistence of fibrin polymer, fibrosis displays a higher occurrence. Thus, technologies that target fibrin formation and/or fibrinolysis have demonstrated a level of success in combating fibrotic responses.

Therefore, a method is provided for detecting fibrotic disorders in a subject that involves administering to the subject a fibrin knob peptide. Methods are also provided for treating fibrotic disorders in a subject by administering to the subject a fibrin knob peptide conjugated to a substance that, for example, disrupts fibrin polymerization, inhibits fibrin polymer stability, or promotes fibrinolysis.

Pulmonary fibrosis is exceptionally insidious. The architecture and mechanics of the mature organ make it exceptionally prone to rapid progression of fibrosis. Following a positive diagnosis, usually the presence of a nodule of dense, highly proliferative fibroblasts in biopsies, patients normally display a life expectancy of only 4 years. Recent studies indicate a rapid increase (over 150%) in the incidence of the disease over the past three years, further underscoring the importance of developing effective treatments for this deadly disease. There is no one universally accepted treatment for pulmonary fibrosis and no commercially available product has demonstrated a proven benefit and therefore the FDA has declared pulmonary fibrosis an orphan indication in hopes of promoting translational efforts.

Therefore, a method is provided for detecting pulmonary fibrosis in a subject that involves administering to the subject a fibrin knob peptide conjugated to a label. In this method, the fibrin knob peptide conjugate will bind in a dose-dependent manner to the fibrin in the ECM of the lung and the label will subsequently concentrate at that location.

In some embodiments, the fibrin knob peptides are conjugated to an inert carrier that can sterically hinder fibrin polymerization. For example, the fibrin knob peptides can be conjugated to polyethylene glycol (single- or multi-arm). In other embodiments, the fibrin knob peptides are conjugated to an enzyme that can improve local fibrinolytic activity. For example, the fibrin knob peptides can be conjugated (e.g., in a fusion protein) to tissue plasminogen activator (tPA). tPA is used in diseases that feature blood clots, such as pulmonary embolism, myocardial infarction and stroke, in a medical treatment called thrombolysis. To be effective in ischemic stroke, tPA must be administered within the first three hours of the event to be given intravenously, or within six hours to be administered through an arterial catheter directly to the site of occlusion.

B. Method of Treating a Wound

Methods are disclosed for controlling bleeding and improving wound healing in a subject. Approaches for controlling bleeding, binding tissues, and inducing tissue regeneration are significantly needed in surgery, trauma, and emergency response medicine. Substantial efforts to develop polymer systems addressing these needs have produced numerous products, yet in most cases such engineered polymers have not performed better than the body's own hemostatic/tissue sealant system, fibrinogen/fibrin. The fibrinogen/fibrin system is useful as a surgical sealant because it rapidly forms an insoluble network that prevents blood loss following vascular injury and it effectively binds or 'glues' tissues when used at high concentrations. However, its main advantages as a rapidly forming sealant also represent its principal shortcomings. Clinically useful formulations of fibrin-based systems are orders of magnitude more concentrated than native circulating fibrinogen, and they polymerize into fiber networks whose extreme density prevent adjacent tissues from remodeling them in normal, regenerative processes. Many previous strategies in regenerative medicine that have relied on commercially available fibrin scaffolds (e.g. TISSEEL VH, Baxter) have generated inconsistent results because although these polymer systems support the mechanical loads necessary for a tissue sealant, they are biochemically 'nonspecific' and induce hyperproliferation and scar formation. Moreover they are physically 'nonpermissive' and prevent the angiogenic vascular invasion necessary for tissue regeneration. Addressing these significant shortcomings in an otherwise promising clinical biomaterial requires new strategies for separating out and independently tuning both the biochemical properties of fibrin and the physical characteristics of fibrin's polymerized matrices.

A method is therefore disclosed for inducing, promoting, or enhancing fibrin clot formation in a subject. The method can involve administering to the subject a composition that includes a fibrin knob peptide conjugated to a substance that promotes wound healing. For example, the fibrin knob peptide can be conjugated (e.g., as a fusion protein) to a growth factor that promotes wound healing.

The method can involve administering to the subject a composition that includes a fibrin knob peptide conjugated to an inert carrier that sterically hinders fibrin polymerization and/or destabilizes the polymer once formed. In In some embodiments, the method inhibits hemorrhage. In some embodiments, the method inhibits post-surgical adhesion. In some embodiments, the method inhibits scar formation. In some embodiments, the method increase would closure.

C. Method of Modulating Fibrin Glue Properties

Methods are disclosed for modulating the properties of a fibrin glue for therapeutic use. For example, methods are provided for introducing fibrin knob-containing peptides into fibrin glue that alters the physical prosperities of the fibrin glue. Generally, the physical properties of the glue are modified based on the substance conjugated to the fibrin knob peptides.

For example, fibrin knob peptides conjugated to PEG can be used to alter the physical properties of the resulting fibrin glue/hydrogel. In some embodiments, the PEG concentration and degree of branching can alter the ability of cells, including blood vessels, to invade the gel.

Other substances can be conjugated to the fibrin knob peptides to alter other properties, such as the regenerative potential of the fibrin glue/hydrogel. For example, growth factors conjugated to the fibrin knob peptides can in some embodiments promote tissue growth D. Method of Making Fibrin Knob Peptides Peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant Ga. (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

EXAMPLES

Example 1

Recombinant Fusion Protein Production

Materials and Methods

Modification of Bacterial Expression Vector

The original thrombin cleavage site in the pGEX4T-1 vector (GE Healthcare, Piscataway, N.J.) was modified from LVPR↓GSPE (SEQ ID NO:14) to LVPR↓GPRV (SEQ ID NO:15), LVPR↓GPRP (SEQ ID NO:16) and LVPR↓GHRP (SEQ ID NO:17) using the QuikChange® II-E Site-Directed Mutagenesis Kit (Stratagene, La Jolla, Calif.). All plasmids were introduced to and maintained in the electro-competent XL-1 Blue E. coli strain provided and cultured in LB+ ampicillin plates at 37° C. Plasmids were extracted from cultures using the QIAquick Spin Miniprep Kit (QIAGEN, Valencia, Calif.) and verified via sequencing (Johns Hopkins Synthesis & Sequencing Facility, Baltimore, Md.).

Amplification and Insertion of FnIII$_{9-10}$ into Expression Vectors

Fibronectin's cell-binding $9^{th}$ and $10^{th}$ type III repeats (FnIII$_{9-10}$) was used as our model protein. The SalI site in the multiple cloning site (MCS) was used to insert the FnIII$_{9-10}$ open reading frame into the pGEX4T$_{GSPE}$, pGEX4T$_{GPRV}$, pGEX4T$_{GPRP}$ and pGEX4T$_{GHRP}$ vectors obtained above using standard molecular cloning techniques (enzymes purchased from NEB, Ipswich, Mass.). Briefly, the FnIII$_{9-10}$ open reading frame was amplified in a high fidelity polymerase chain reaction with Phusion High Fidelity DNA polymerase from the previously established pGEX4T-1-FnIII$_{9-10}$ plasmid (Martino M M, et al. Biomaterials 2009, 30(6):1089-1097) using primers with flanking SalI sequences (underlined) and introducing Gly-Gly-Cys (bold) on the C-terminal if necessary: ACTGGTCGACTG GGTCTTGATTC-CCCAACT (SEQ ID NO:12) and ACTG GTCGACTCAGCAACCACCTGTTCGGTAATTAATGGA (SEQ ID NO:13). Vectors and insert were digested with SalI. The vectors were additionally dephosphorylated using heat-deactivate-able Antartic phosphatase to prevent self-ligation. The respective vectors and insert were ligated using T4 DNA Ligase and transformed into electro-competent XL-1 Blue cells. Selection for successfully ligated plasmids containing the insert was made on LB+ ampicillin plates. The orientation of the FnIII$_{9-10}$ insert was verified by in-colony PCR-screening using forward or reverse primers on the plasmid in combination with an internal primer within the insert. Colonies with the insert in the correct orientation were grown up for plasmid extraction. All plasmids were verified via sequencing.

Protein Production and Purification

Plasmids containing the FnIII$_{9-10}$ insert were transformed into electro-competent BL21 E. coli and protein production of the Glutathione S-transferase (GST)-tagged proteins stimulated as recommended by the manufacturer. Following appropriate culture, cells were pelleted by centrifugation at 4° C. and resuspended in ice-cold PBS supplemented with protease inhibitor (Roche, Indianapolis, Ind.), then lysed by adding 1 mg/mL of lysozyme followed by sonication. 1% Triton X and 10 U/mL of DNase was added and the lysate further incubated for 30 min with gentle agitation. The cell lysate was cleared of cellular debris by centrifugation followed by filtration through a 0.22 µm pore filter. Purification of the recombinant proteins was performed following the manufacturer's recommendation using ÄKTAFPLC™ with a GST Prep FF 16/10 column (GE Healthcare) for affinity purification of GST-tagged proteins. Washing and binding steps were done in filter-sterilized PBS and elution completed with glutathione (GSH) buffer (50 mM Tris-HCl, 10 mM reduced GSH, pH 8.0). The GSH buffer was then exchanged to PBS using an Amicon Ultra-15 centrifugal filter with MWCO 10,000 (Millipore, Billerica, Mass.). The GST-tagged protein was incubated overnight with bovine thrombin (MP Biomedicals, Solon, Ohio) dosed at 10 U per mg recombinant protein and the cleaved protein solution was reintroduced on the GST Prep FF 16/10 column to remove the GST tag, followed by the HiTrap Benzamidine FF column (GE Healthcare) to remove thrombin. Gxxx-FnIII$_{9-10}$-(C) (SEQ ID NO:20) proteins were assessed for purity by SDS-PAGE and quantitated at Abs$_{280\ nm}$ using the Nanodrop 1000 (Thermo Scientific, Wilmington, Del.) using extinction coefficients calculated using an online peptide property calculator (found at http://www.basic.northwestentedu/biotools/proteincalc.html), then aliquoted and stored at −80° C. until use.

Results

An expression vector system allowing the simple and rapid cloning of any gene-of-interest into a series of vectors was developed thereby enabling the creation of any desired protein endowed with an N-terminal fibrin knob sequence. The pGEX4T-1 expression vector allows the expression of proteins with an N-terminal 26 kDa GST tag. This tag can then be removed via thrombin cleavage, analogous to the process of fibrinogen activation wherein protein segments are cleaved from the N-termini of the Aα- and Bβ-chains. Using the original pGEX4T-1 vector, the N-terminal sequence exposed upon thrombin cleavage of the GST-tagged protein is GSPE (Gly-Ser-Pro-Glu, SEQ ID NO:11), which does not bind to fibrin pockets. The corresponding coding sequence on the expression vector to each of three knob tetrapeptide sequences, namely GPRP (SEQ ID NO:1), GPRV (SEQ ID NO:2) and GHRP (SEQ ID NO:3), was modified using site-directed mutagenesis (FIG. 2). The coding sequence for the model protein, the 20 kDa FnIII$_{9-10}$ fragment, was then inserted using standard molecular cloning techniques. The model protein has a known crystal structure, can be produced using standard bacterial expression systems, and may be detected via immunological assays using a number of commercially available antibodies (Petrie T A, et al. Biomaterials 2006, 27(31):5459-5470; Martino M M, et al. Biomaterials 2009, 30(6):1089-1097; Leahy D J, et al. Cell 1996, 84(1):155-164). The GST tag served dual purposes as affinity tag and a measure of thrombin cleavage efficacy. Using this platform cloning and expression system the following knob-protein fusions were successfully expressed and purified: GSPE-FnIII$_{9-10}$ (non-binding control, SEQ ID NO:11), GPRP-FnIII$_{9-10}$ (SEQ ID NO:1), GPRV-FnIII$_{9-10}$ (SEQ ID NO:2) and GHRP-FnIII$_{9-10}$ (SEQ ID NO:3).

Example 2

Evaluating Fusion Protein Fibrinogen-Binding Affinity Using SPR

Materials and Methods

Preparation of Fibrinogen Fragment D

Human fibrinogen (# FIB3, Enzyme Research Laboratories, South Bend, Ind.) at 2 mg/mL was digested with 0.1

U/mL human plasmin (Enzyme Research Laboratories) in HEPES+Ca buffer (150 mM NaCl, 5 mM $CaCl_2$, 25 mM HEPES, pH 7.4) overnight at room temperature. Fragment D (or D-domain) was isolated as previously described, with slight modifications, using a polymeric resin with covalently linked GPRPAA (SEQ ID NO:10) peptide (Kostelansky M S, et al. Biochemistry 2002, 41(40):12124-12132). Briefly, the plasmin-digested fibrinogen and GPRPAA-beads were incubated for 30 min, with occasional agitation. The unbound protein fragments were removed with exhaustive washing with HEPES+Ca buffer. Fragment D was eluted using 1 M sodium bromide, 50 mM sodium acetate, pH 5.3 and exchanged back into HEPES+Ca buffer using a centrifugal filter with MWCO 10,000.

Surface Plasmon Resonance (SPR) Binding Assays

The BIACORE® 2000 was used to perform SPR experiments to determine the equilibrium dissociation constants ($K_D$) of the various Gxxx-$FnIII_{9-10}$ (SEQ ID NO:20) proteins to fibrinogen fragment D covalently immobilized to gold-coated coverslips via self-assembled monolayer (SAM) surface chemistry. Mixed SAMs were generated on gold-coated chips as described previously by incubating with a 1 mM mixture of tri(ethylene glycol)-terminated alkanethiol (HS—$(CH_2)_{11}$—$(OCH_2CH_2)_3$—OH; $EG_3$) and carboxylic acid-terminated alkanethiol (HS—$(CH_2)_{11}$—$(OCH_2CH_2)_6$—$OCH_2COOH$; $EG_6$-COOH) thiols for 4 h (Petrie T A, et al. Biomaterials 2006, 27(31):5459-5470). After mounting the gold chip in the BIACORE® 2000, the $EG_6$-COOH component of the SAM was activated with 200 mM EDC and 50 mM NHS in 0.1 M 2-(N-morpho)-ethanesulfonic acid and 0.5 M NaCl, pH 6.0 (5.4/min for 10 min). Fragment D was then immobilized via NHS-amine linkages (5 µL/min for 10 min). Unreacted NHS groups were quenched with 20 mM ethanolamine (10 µL/min). Upon stabilization of the baseline signal, varying concentrations of the Gxxx-$FnIII_{9-10}$ (SEQ ID NO:20) were flowed at 25 µL/min for 4 min immediately followed by a 10 min dissociation phase; the fragment D surface was regenerated between analyte runs. All sensorgram response curves were normalized to a reference flow cell in which fragment D was not immobilized. SPR sensorgrams were analyzed and equilibrium constants were determined with Scrubber 2 and ClampXP software (Center for Biomolecular Interactions Analysis, University of Utah) (Morton T A, et al. Anal Biochem 1995, 227(1):176-185).

Results

Figure 3A:
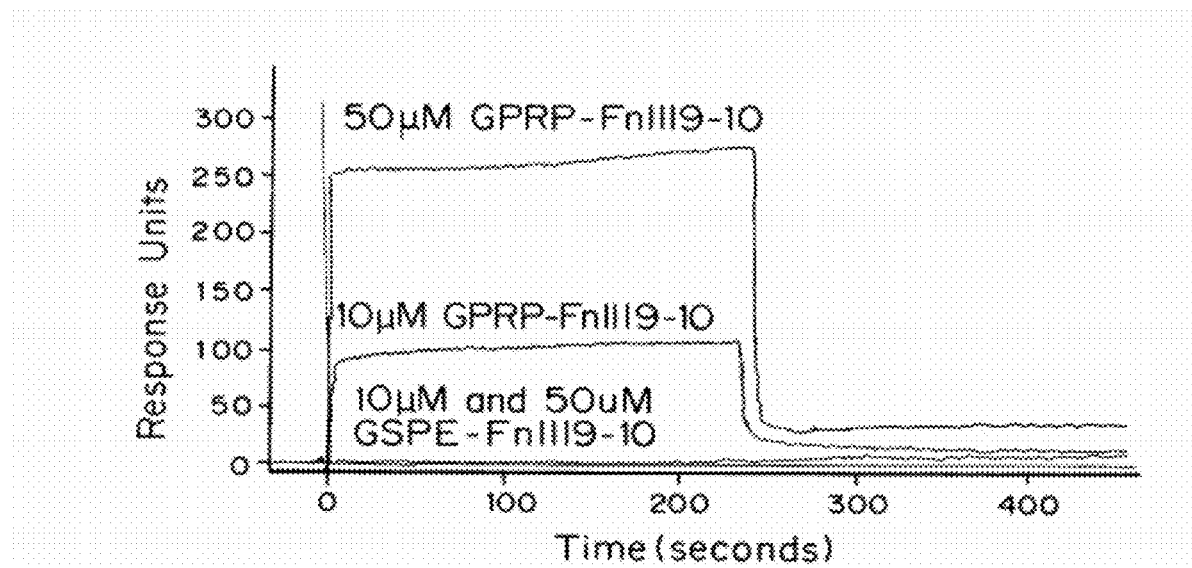
FIG. 3A is a surface plasmon resonance (SPR) line-graph showing protein-protein affinity (1 RU=1 $pg/mm^2$) of fusion proteins for immobilized fibrinogen fragment D as a function of time (s) for 50 µM (top line) and 10 µM (middle line) GPRP-$FnIII_{9-10}$ (SEQ ID NO:1) and 10 µM and 50 µM (bottom lines) GSPE-$FnIII_{9-10}$ (SEQ ID NO:11).
Figure 3B:
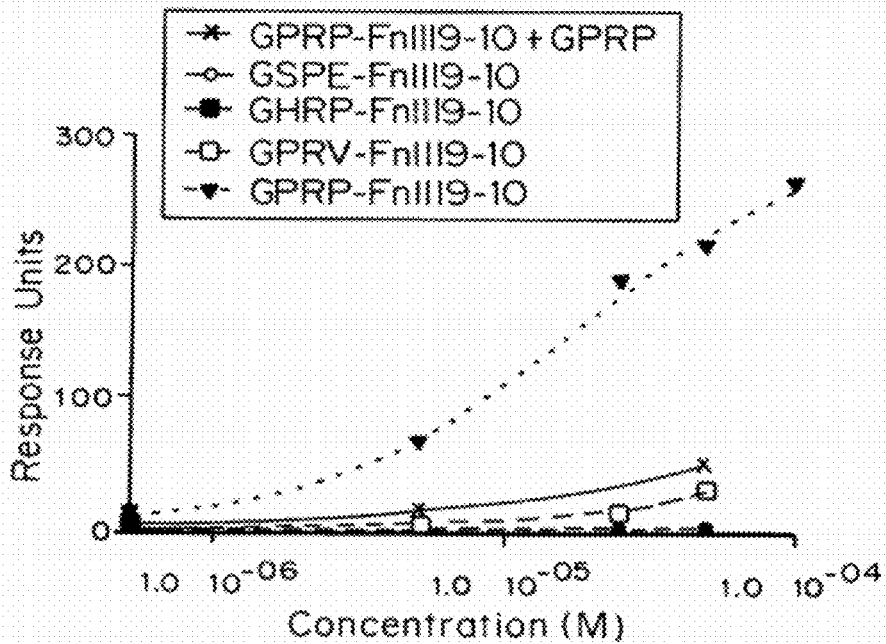
FIG. 3B is a SPR line-graph showing protein-protein affinity (1 RU=1 $pg/mm^2$) of fusion proteins for immobilized fibrinogen fragment D as a function of concentration (M) for GSPE-$FnIII_{9-10}$ (SEQ ID NO:11, open circle), GPRP-$FnIII_{9-10}$ (SEQ ID NO:1, triangle), GPRV-$FnIII_{9-10}$ (SEQ ID NO:2, open square), GHRP-$FnIII_{9-10}$ (SEQ ID NO:3, closed square), and GPRP-$FnIII_{9-10}$ (SEQ ID NO:1)+GPRP (SEQ ID NO:1, "x").

The affinity of Gxxx-$FnIII_{9-10}$ (SEQ ID NO:20) proteins for immobilized fibrinogen fragment D was examined using surface plasmon resonance (SPR). Fibrinogen fragment D, comprising the C-terminal polymerization pockets of fibrinogen (i.e. D-domain) without the N-terminal knobs, was covalently immobilized on gold chips via self-assembled monolayers (SAMs). Following, solutions of Gxxx-$FnIII_{9-10}$ (the analyte, SEQ ID NO:20) were flowed across the fragment D surface, with protein-protein interactions registering as an increase in response units, as measured using the Biacore 2000 system (FIG. 3A). For each protein, the equilibrium response at each concentration was plotted against concentration and fit to a single-site binding model to determine the equilibrium dissociation constant, $K_D$ (FIG. 3B). GPRP-$FnIII_{9-10}$ (SEQ ID NO:1) had the greatest affinity for immobilized fibrinogen fragment D, with a $K_D$ of 3.0±0.1 µM. This is congruent with recently presented SPR data reporting $K_D$s for knob-containing N-terminal disulphide knot (NDSK) fragments in similar µM range (Geer C B, et al. J Thromb Haemost 2007, 5(12):2344-2351). In contrast, GPRV-$FnIII_{9-10}$ (SEQ ID NO:2) generated a $K_D$ of 125±6 µM while both GHRP-$FnIII_{9-10}$ (SEQ ID NO:3) and the control GSPE-$FnIII_{9-10}$ (SEQ ID NO:11) demonstrated no detectable binding to fragment D. Additionally, the specificity of the GPRP-$FnIII_{9-10}$ (SEQ ID NO:1) interaction with the pocket was demonstrated by adding a 10-molar excess of soluble GPRP (SEQ ID NO:1) peptide to the flow analyte solution (FIG. 3B). A significant increase in $K_D$ was observed from 3.0 µM to 43±4 µM under these competing conditions, suggesting that that the fibrin(ogen)-binding capacities of GPRP-$FnIII_{9-10}$ (SEQ ID NO:1) is attributed to its N-terminal knob sequence. Based on the promising SPR data, further investigations were focused on the high affinity GPRP-$FnIII_{9-10}$ (SEQ ID NO:1) protein and the non-binding control GSPE-$FnIII_{9-10}$ (SEQ ID NO:11).

Example 3

Evaluating Fusion Protein Fibrinogen-Binding Affinity Using ELISA

Materials and Methods

ELISA Binding Assays

A modified ELISA technique was used to establish the affinity of fibrinogen for the various Gxxx-$FnIII_{9-10}$-C (SEQ ID NO:20) proteins covalently immobilized on maleimide-activated plates via their C-terminal cysteines. Sulfhydryl-containing proteins/peptides were added to pre-blocked maleimide-activated 96-well plates (Pierce, Thermo Scientific, Rockford, Ill.) at 10 µg/mL in conjugation buffer (CB) comprising 150 mM NaCl, 100 mM phosphate, 10 mM EDTA, pH 7.2, with attachment occurring via maleimide-sulfhydryl (thioether) linkages. TCEP (1 mM) was added to maintain sulfhydryl groups in the reduced form. Following, unreacted maleimide groups were quenched with 20 µg/mL cysteine in CB. Human fibrinogen (25 µg/mL) was incubated with the substrates and unbound protein removed by washing. Bound fibrinogen was detected using HRP-conjugated goat anti-fibrinogen antibody (MP Biomedicals #55239) and 1-Step™ Ultra TMB-ELISA (Pierce). The TMB reaction was quenched with 1 M $H_2SO_4$ before measuring the $Abs_{450\ nm}$ using the SPECTRAMAX® M2 (Molecular Devices, Sunnyvale, Calif.). All intervening wash steps were conducted using washing buffer (WB) comprising 150 mM NaCl, 100 mM phosphate, 0.05% Tween-20, pH 7.2; all binding steps were conducted using binding buffer (BB) comprising PBS+1% BSA. For basic affinity assays, the concentration of the fusion proteins was varied. For specificity assays, varying concentrations of Gxxx (SEQ ID NO:20) tetrapeptides (Genscript, Piscataway, N.J.) were added to the fibrinogen solution during incubation with the covalently immobilized proteins.

Results

Figure 4A:
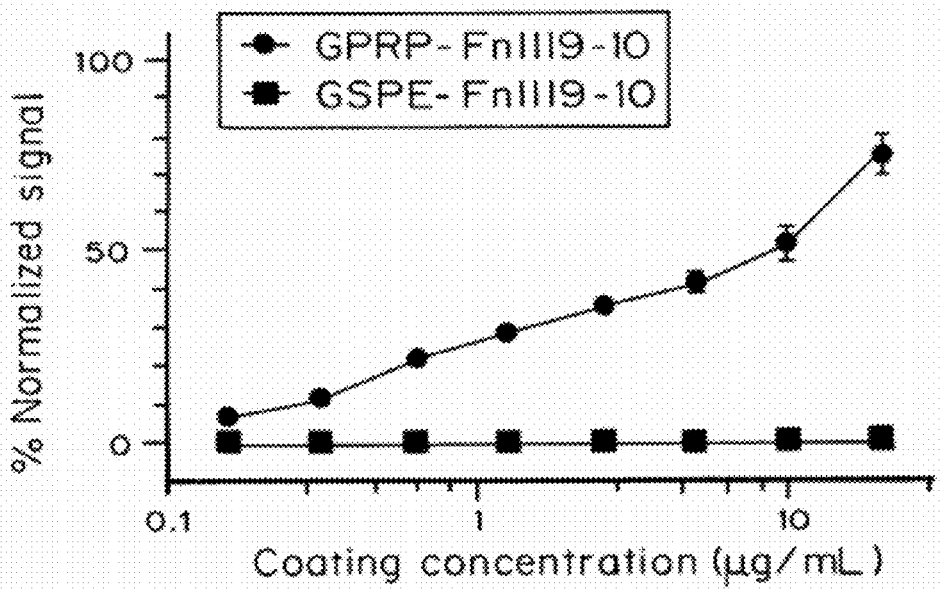
FIG. 4A is a line graph from ELISA studies showing affinity of fusion proteins for fibrinogen (percent signal at Abs450 nm normalized against maximum signal obtained using GPRPFPAC (SEQ ID NO:5) at coating concentration of 20 µg/ml) as a function of fibrinogen coating concentration (µg/ml) for GPRP-$FnIII_{9-10}$ (SEQ ID NO:1, circle) and GSPE-$FnIII_{9-10}$ (SEQ ID NO:11, square).

In addition to the Gxxx-$FnIII_{9-10}$ (SEQ ID NO:20) recombinant proteins described above, equivalent versions with an additional C-terminal cysteine were expressed and purified. The Gxxx-$FnIII_{9-10}$-C (SEQ ID NO:20) proteins were immobilized on maleimide-activated 96-well plates via maleimide-sulfhydryl chemistry, allowing the unidirectional presentation of their N-terminal knobs to fibrinogen-containing solutions in the wells. Using standard ELISA techniques, the bound fibrinogen was detected using an anti-fibrinogen HRP-conjugate, with stronger signals corresponding to increased amounts of bound fibrinogen. Complementing the SPR data, the ELISA results indicate that soluble fibrinogen bound to immobilized GPRP-$FnIII_{9-10}$-C (SEQ ID NO:1) but not the control, GSPE-FnIII$_{9-10}$-C (SEQ ID NO:11) (FIG. 4A). This demonstrates the mechanism of action, that fibrinogen is binding the knob-protein fusion via the knob sequences and not via interaction with the fibronectin domains in our model protein.

Figure 4B:
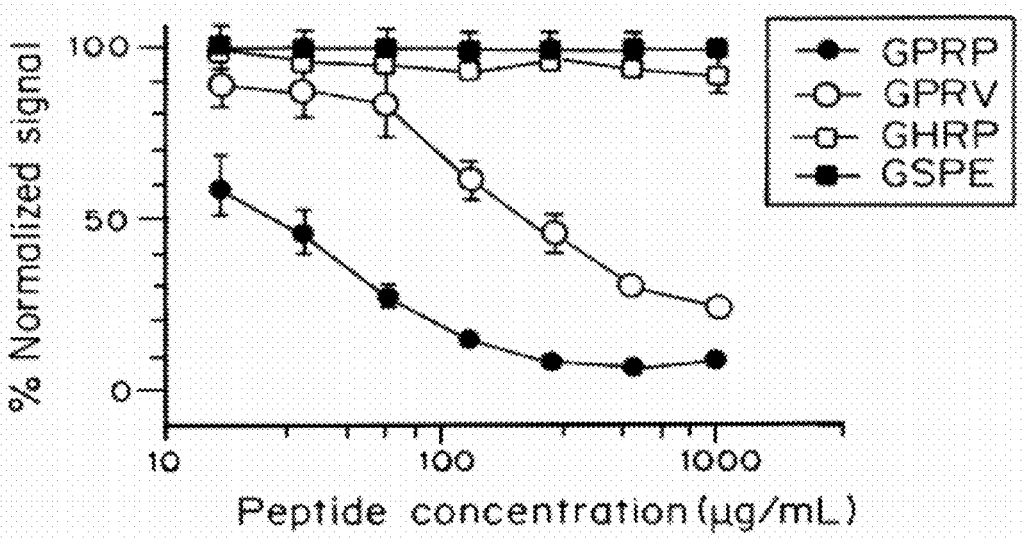
FIG. 4B is a line graph from ELISA studies showing affinity of fusion proteins for fibrinogen (percent signal at Abs450 nm normalized against signal obtained in the presence of the non-binding GSPE (SEQ ID NO:11) peptide) as a function of peptide concentration (µg/ml) for GPRP (SEQ ID NO:1, closed circle), GPRV (SEQ ID NO:2, open circle), GHRP (SEQ ID NO:3, open square), and GSPE (SEQ ID NO:11, closed square).

To further demonstrate specificity, soluble tetrapeptides modeled after fibrin knob sequences were added in large molar excess ($10^2$- to $10^4$-fold) to the fibrinogen solution that was to be incubated with immobilized GPRP-FnIII$_{9-10}$-C (SEQ ID NO:1). As expected, free GPRP (SEQ ID NO:1) tetrapeptides competed with the immobilized GPRP-FnIII$_{9-10}$-C (SEQ ID NO:1) for binding to fibrinogen, resulting in a dose-dependent inhibition of fibrinogen binding following a one-hour pre-incubation (FIG. 4B). This result suggests that the GPRP (SEQ ID NO:1) sequence is the mediator of the interaction between the immobilized protein and fibrinogen. The tetrapeptides GPRV (SEQ ID NO:2) and GHRP (SEQ ID NO:3) are also known to bind fibrinogen via knob:pocket interactions, albeit with reduced affinities (Laudano A P, et al. Biochemistry 1980, 19(5):1013-1019). These results indicate that GPRV (SEQ ID NO:2) competed with GPRP-FnIII$_{9-10}$ (SEQ ID NO:1) for binding to fibrinogen, but to a lesser extent as compared to GPRP (SEQ ID NO:1), while GHRP (SEQ ID NO:3) was not a significant competitor to GPRP-FnIII$_{9-10}$ (SEQ ID NO:19) under the experimental conditions. Notably, these results agree with the SPR data indicating that the affinity constant of GPRV-FnIII$_{9-10}$ (SEQ ID NO:2) was at least an order of magnitude smaller than that of GPRP-FnIII$_{9-10}$ (SEQ ID NO:19), while GHRP-FnIII$_{9-10}$ (SEQ ID NO:3) had little affinity for fibrinogen fragment D. These results support the interpretation that the interaction between the GPRP-FnIII$_{9-10}$ (SEQ ID NO:1) protein and fibrinogen is primarily mediated by the respective N-terminal tetrapeptide sequences through specific interactions with fibrin(ogen) pockets.

Example 4

Fibrin Assembly in the Presence of Fusion Protein

Materials and Methods

Biotinylation of Fusion Proteins

Gxxx-FnIII$_{9-10}$-C (SEQ ID NO:20) proteins were conjugated via the sulfhydryl group of the C-terminal cysteine to maleimide-functionalized biotin (maleimide-PEG$_2$-biotin; Pierce #21902) following the manufacturer's recommended protocol. Unreacted maleimide-PEG$_2$-biotin was removed using Slide-A-Lyzer dialysis cassettes with MWCO 3,500 (Pierce). The extent of biotinylation was determined using the Pierce Biotin Quantitation Kit (Pierce).

Fibrin Clotting Assays

Clotting was initiated in a 96-well plate format and the Abs$_{350\ nm}$ used as a standard measure of turbidity. Briefly, increasing doses of the Gxxx-FnIII$_{9-10}$-biotin (SEQ ID NO:20) proteins were preincubated with 4 mg/mL human fibrinogen (ERL # FIB3) in Tris+Ca buffer (140 mM NaCl, 5 mM CaCl$_2$, 20 mM Tris, pH 7.4). Following the 1 h preincubation, clotting was initiated by adding 1 U/mL of human thrombin (ERL) or batroxobin moojeni (Centerchem, Norwalk, Conn.), and 1 U/mL factor XIIIa (kindly donated by Baxter AG, Vienna Austria). Real time measurements of clot turbidity were taken every minute for 1 h. To determine the amount of unclotted protein, the clots were spun down and the supernatant or clot liquor was analyzed for total protein using the Quant-iT protein assay (Invitrogen, Carlsbad, Calif.).

Rheological Assays

The Bohlin CVO 120 high resolution rheometer (Malvern Instruments, Westborough, Mass.) with plate-plate geometry was used to assess the viscoelastic characteristics of fibrin clots at room temperature. Briefly, fibrinogen (preincubated with or without Gxxx-FnIII$_{9-10}$-biotin (SEQ ID NO:20) as indicated) and enzyme mixtures with identical compositions as those used in the turbidity and clottability assays were mixed by pipetting and immediately added to the bottom plate. The upper plate (14 mm diameter) was immediately lowered to a gap size of 1 mm and the mixture was allowed to polymerize for 30 min in a humid chamber. Following, oscillating measurements were taken over a frequency range of 0.05 to 1.0 Hz at a constant strain of 0.5%.

Results

Figure 5A:
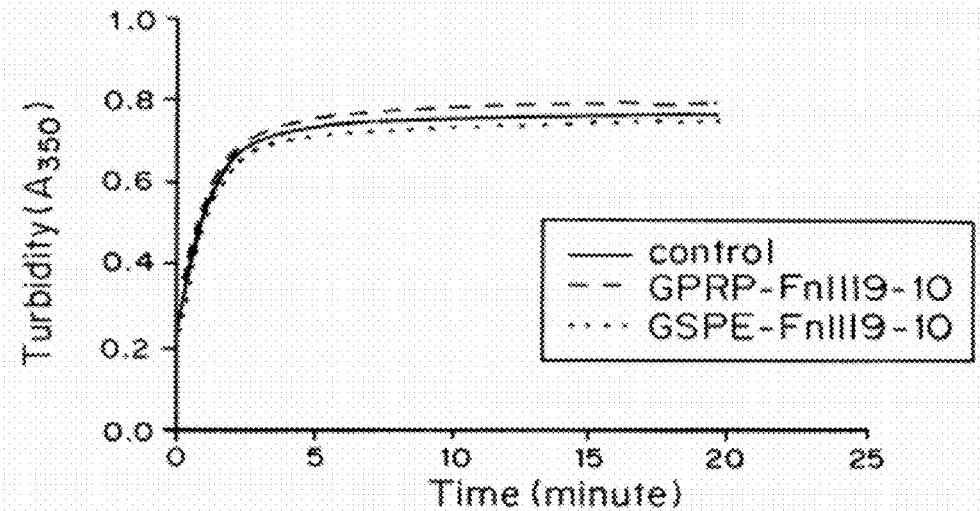
FIGS. 5A and 5B are line graphs showing turbidity as a function of time (min) for clots formed from 6 µM (=2 mg/mL) fibrinogen solutions containing 0.6 µM control (solid line), GPRP-$FnIII_{9-10}$-biotin (SEQ ID NO:1, dashed line) and GSPE-$FnIII_{9-10}$-biotin (SEQ ID NO:11, dash-dot line) fusion proteins upon the addition of 1 U/mL factor XIIIa and 1 U/mL human α-thrombin (FIG. 5A) or batroxobin moojeni (FIG. 5B).
Figure 5B:
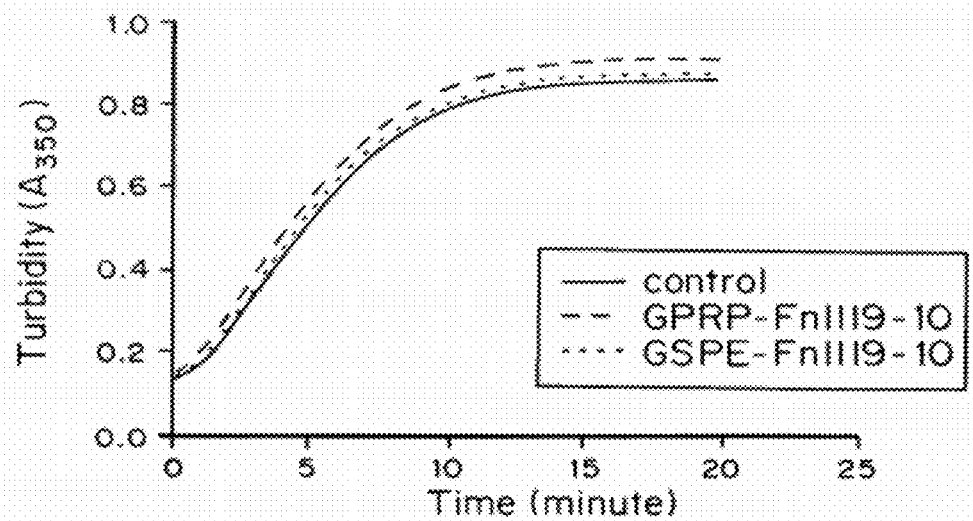
Figure 5C:
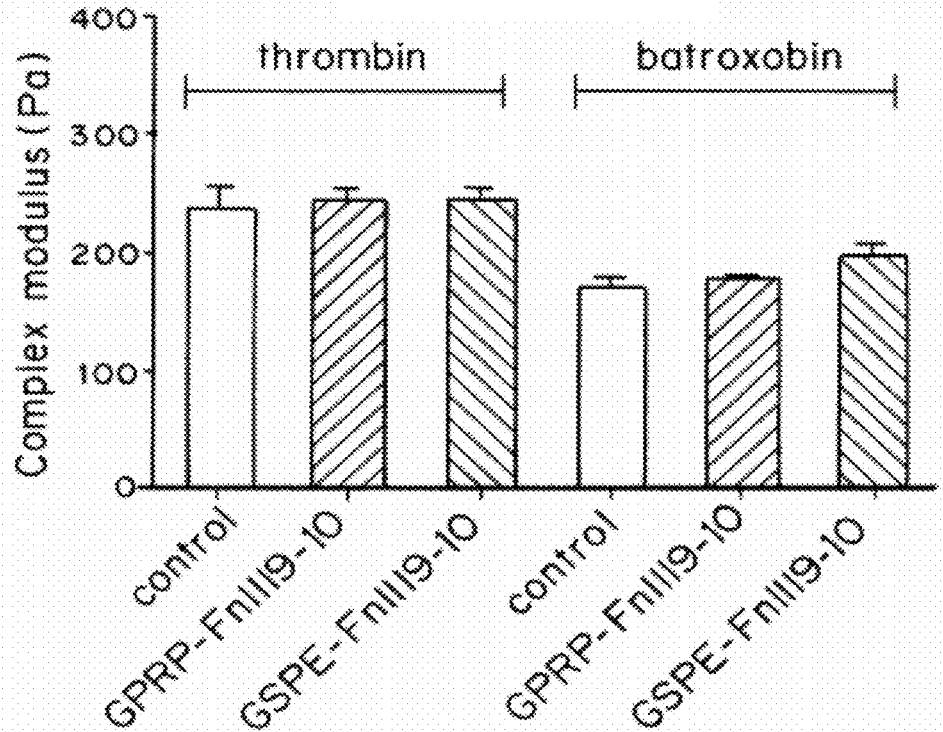
FIG. 5C is a bar graph showing complex modulus (Pa) of the clots after 30 min clotting time using control (first and fourth bars), GPRP-$FnIII_{9-10}$ (SEQ ID NO:1, second and fifth bars), and GSPE-$FnIII_{9-10}$ (SEQ ID NO:11, third and sixth bars).
Figure 5D:
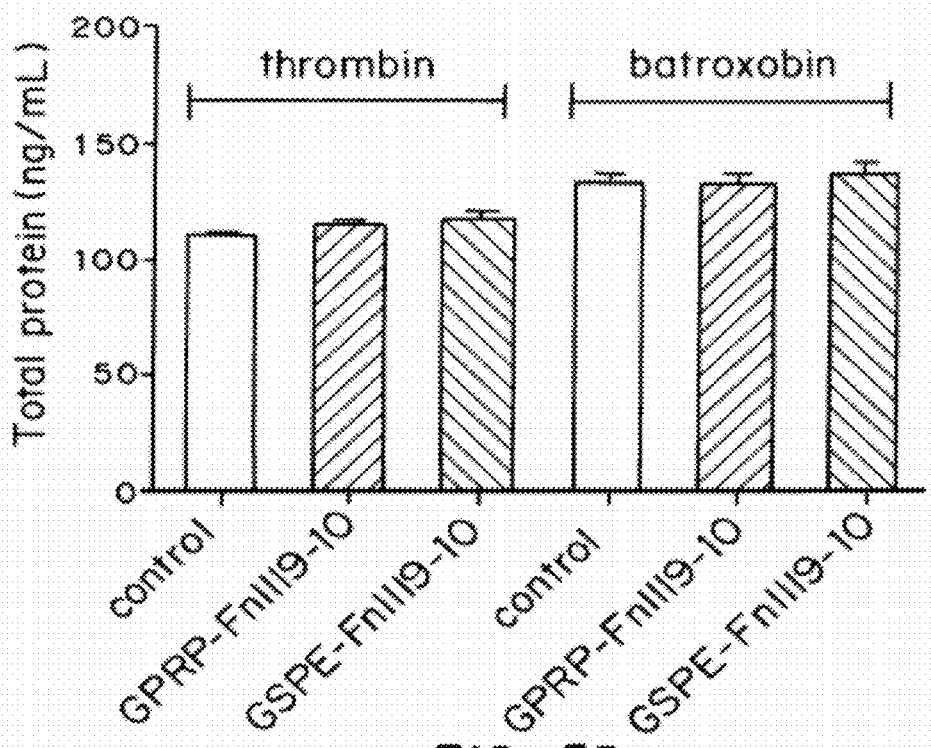
FIG. 5D is a bar graph showing soluble protein (ng/ml) in the clot liquor from clots after 1 hour clotting time using control (first and fourth bars), GPRP-$FnIII_{9-10}$ (SEQ ID NO:1, second and fifth bars), and GSPE-$FnIII_{9-10}$ (SEQ ID NO:11, third and sixth bars).

Since knob:pocket interactions are involved in fibrin assembly, the addition of non-native knob-protein fusions could potentially interfere with this process and impede matrix formation, thereby limiting the utility of this affinity system for the retention of proteins within fibrin matrices. The impact of such knob-protein fusions on fibrin assembly was therefore evaluated. GPRP-FnIII$_{9-10}$-C (SEQ ID NO:1) was selectively conjugated to maleimide-functionalized biotin, generating GPRP-FnIII$_{9-10}$-biotin (SEQ ID NO:1) conjugates that can be quantitated via sandwich ELISA. GPRP-FnIII$_{9-10}$-biotin (SEQ ID NO:1) proteins were preincubated with fibrinogen before clotting was induced by the addition of factor XIIIa and either thrombin (exposes both A- and B-knobs) or batroxobin (exposes the A-knobs). The process of fibrin assembly can be inferred from the gross absorbance of the fibrinogen-containing mixture since the lateral aggregation of protofibrils during clotting results in a rapid rise in turbidity (Weisel J W, et al. Biophys 1992, 63(1):111-128). The turbidity curves obtained suggest that fibrin assembly in the presence of thrombin (FIG. 5A) or batroxobin (FIG. 5B) was not significantly impacted by the presence of GPRP-FnIII$_{9-10}$-biotin (SEQ ID NO:1), or the control GSPE-FnIII$_{9-10}$-biotin (SEQ ID NO:11), at the conjugate:fibrinogen molar ratio of 1:10. Rheological assaying of clots formed following a 30-minute clotting time suggests that the presence of either conjugate did not significantly affect the native viscoelastic properties of the clots (FIG. 5C). Moreover, quantitation of the soluble proteins in the clot liquor (the remaining supernatant after spinning down the insoluble fibrin) also indicates that the presence of GPRP-FnIII$_{9-10}$-biotin (SEQ ID NO:1), or the control GSPE-FnIII$_{9-10}$-biotin (SEQ ID NO:11), did not significantly impact the clottability of the mixture (FIG. 5D). These results agree with past research showing that at least a 100-fold excess of the GPRP (SEQ ID NO:1) tetrapeptide was necessary to completely inhibit fibrin assembly (Laudano A P, et al. Proc Natl Acad Sci USA 1978, 75(7):3085-3089) and suggest that the presence of knob-protein fusions will not significantly interfere with the formation of the fibrin matrix when present at the nanogram concentrations relevant for use in protein delivery systems for growth factors.

Example 5

Evaluating Fusion Protein Retention in Fibrin Matrices Using Release Assays

Materials and Methods

Protein Release Assays

Analogous to the clotting assays, Gxxx-FnIII$_{9-10}$-biotin (SEQ ID NO:20) was preincubated with fibrinogen in Tris+Ca buffer in 2 mL conical bottom tubes. Clotting was initiated by adding thrombin or batroxobin, and factor XIIIa. After a one-hour incubation, the resulting clot was overlaid with 1 mL Tris+Ca buffer. The entire volume of buffer was removed and replaced with fresh buffer at 1, 4, 8, 12, 24, 48, 72, 96-hour timepoints for analysis. Gxxx-FnIII$_{9-10}$-biotin (SEQ ID NO:20) proteins in the removed supernatant samples were quantitated using a sandwich ELISA. Briefly, 96-well ELISA plates were coated with 5 μg/mL streptavidin, then washed and blocked with 1% BSA. The sample, mouse monoclonal anti-FnIII$_{9-10}$ antibody (HFN7.1; Developmental Studies Hybridoma Bank, Iowa City, Iowa) and HRP-conjugated goat anti-mouse antibody (Pierce #1858413) were added sequentially to the plate with intervening wash steps. TMB was added to react with the HRP and the reaction quenched with H$_2$SO$_4$ before measuring the Abs$_{450\,nm}$.

Results

GPRP-FnIII$_{9-10}$-biotin (SEQ ID NO:1) binds fibrin(ogen) pockets and does not interfere with the clotting process at the loading concentrations desired for targeted application. The retention of GPRP-FnIII$_{9-10}$-biotin (SEQ ID NO:1) conjugates within three-dimensional fibrin matrices was therefore examined by monitoring protein release from the clots into the surrounding buffer reservoir. In particular, the release profiles from both normal thrombin-catalyzed clots and batroxobin-catalyzed clots were evaluated; batroxobin selectively exposes the A-knobs but not the B-knobs, theoretically leaving an excess of binding pockets that should improve retention characteristics. As described in the previous section, the GPRP-FnIII$_{9-10}$-biotin (SEQ ID NO:1) conjugates were preincubated with fibrinogen at a 1:10 molar ratio (conjugate: fibrinogen), before clotting was induced by the addition of factor XIIIa and either thrombin or batroxobin. After a one-hour incubation period, the clot was overlaid with pre-warmed buffer and incubated at 37° C. with agitation. Samples taken at regular intervals were evaluated for the presence of fibrin (ogen) and conjugate via sandwich ELISAs. In particular, the HFN7.1 conformation-specific antibody was used against the conjugates to further demonstrate that the conformational integrity of the FnIII$_{9-10}$ was preserved during the release assay. Additionally, GPRP-FnIII$_{9-10}$-biotin (SEQ ID NO:1) is capable of binding to ELISA plates coated with fibrinogen and being detected by the same antibody (data not shown), indicating that the conformational integrity of the FnIII$_{9-10}$ domain is preserved even while bound to fibrin(ogen).

Figure 6A:
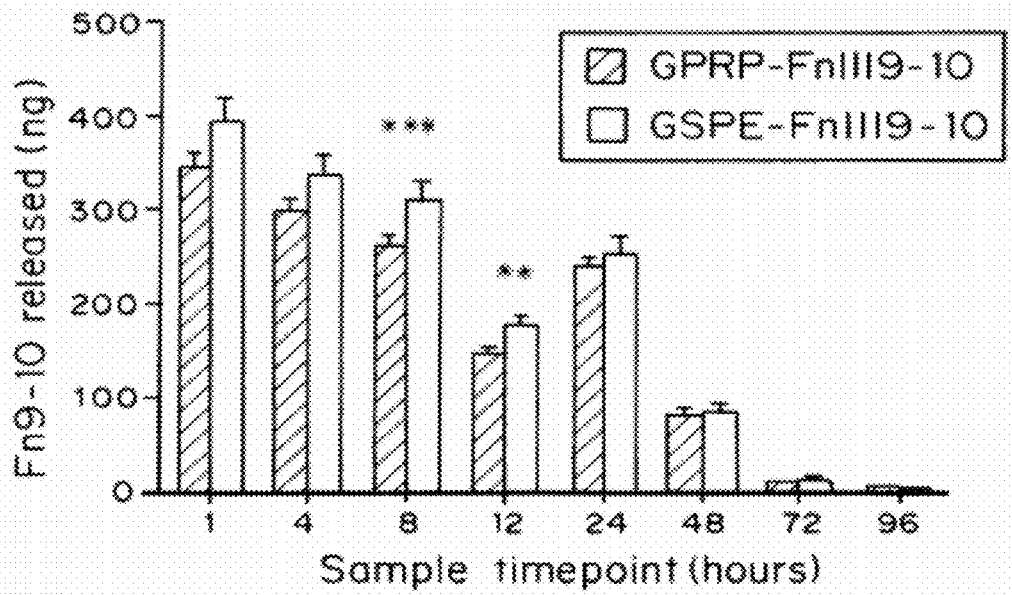
FIGS. 6A and 6C are bar graphs showing $FnIII_{9-10}$ release (ng) at 1 hour ($1^{st}$ set of bars), 4 hours ($2^{nd}$ set of bars), 8 hours ($3^{rd}$ set of bars), 12 hours ($4^{th}$ set of bars), 24 hours ($5^{th}$ set of bars), 48 hours ($6^{th}$ set of bars), 72 hours ($7^{th}$ set of bars), and 96 hours ($8^{th}$ set of bars) using GPRP-$FnIII_{9-10}$ (SEQ ID NO:1, closed bars), and GSPE-$FnIII_{9-10}$ (SEQ ID NO:11, open bars) fusion proteins upon the addition of 1 U/mL factor XIIIa and 1 U/mL human α-thrombin (FIG. 6A) or batroxobin moojeni (FIG. 6C).
Figure 6B:
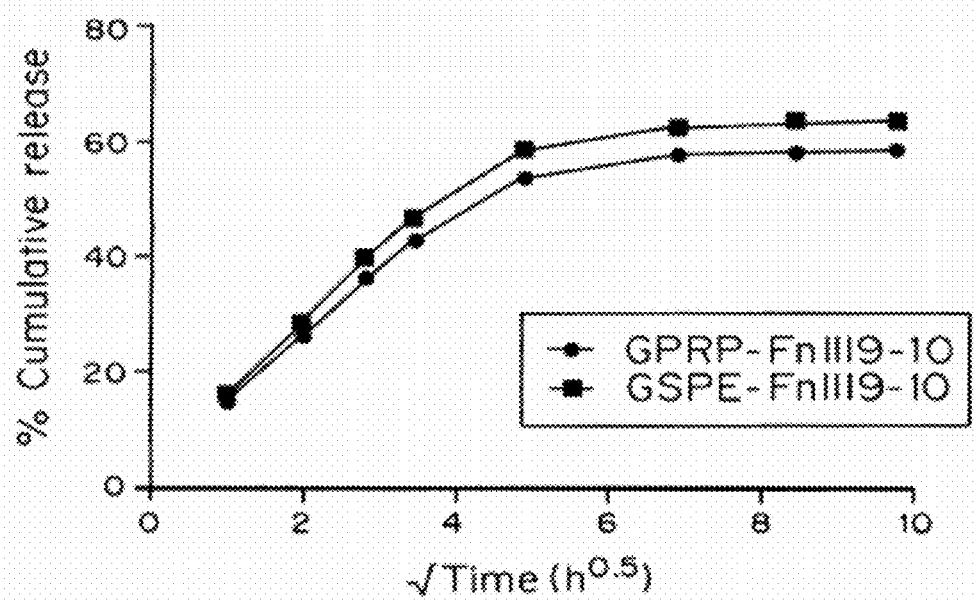
FIGS. 6B and 6D are line graphs showing percent cumulative release as a function of time ($\sqrt{h^{0.5}}$) using GPRP-$FnIII_{9-10}$ (SEQ ID NO:1, circles), and GSPE-$FnIII_{9-10}$ (SEQ ID NO:11, squares) fusion proteins upon the addition of 1 U/mL factor XIIIa and 1 U/mL human α-thrombin (FIG. 6B) or batroxobin moojeni (FIG. 6D).
Figure 6C:
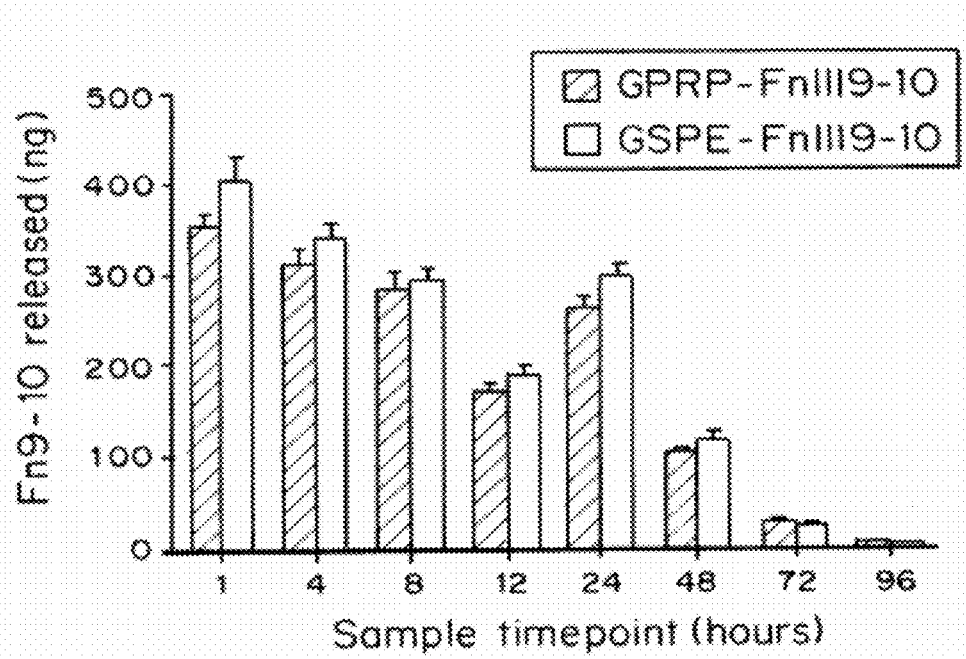
Figure 6D:
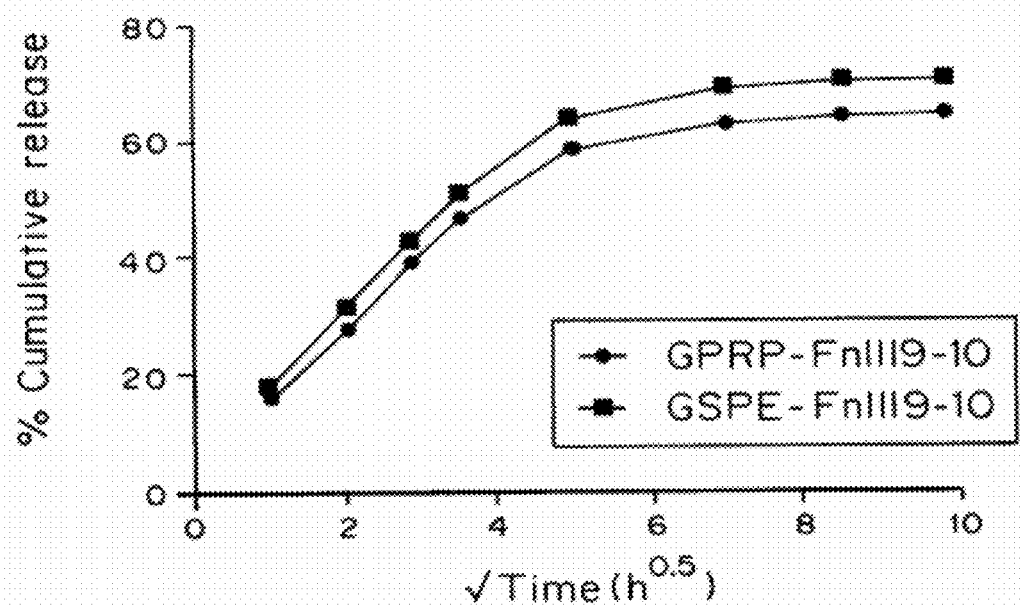
Figure 7A:
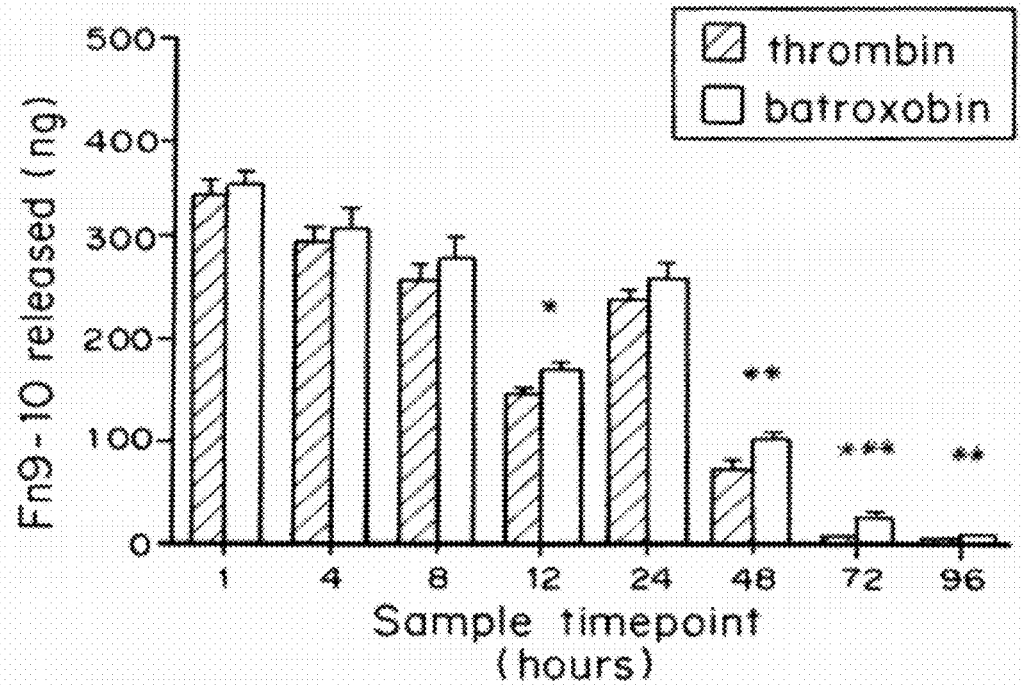
FIGS. 7A and 7C are bar graphs showing $FnIII_{9-10}$ release (ng) at 1 hour ($1^{st}$ set of bars), 4 hours ($2^{nd}$ set of bars), 8 hours ($3^{rd}$ set of bars), 12 hours ($4^{th}$ set of bars), 24 hours ($5^{th}$ set of bars), 48 hours ($6^{th}$ set of bars), 72 hours ($7^{th}$ set of bars), and 96 hours ($8^{th}$ set of bars) using GPRP-$FnIII_{9-10}$ (SEQ ID NO:1, FIG. 7A) or GSPE-$FnIII_{9-10}$ (SEQ ID NO:11, FIG. 7C) fusion proteins upon the addition of 1 U/mL factor XIIIa and 1 U/mL human α-thrombin (closed bars) or batroxobin moojeni (open bars).
Figure 7B:
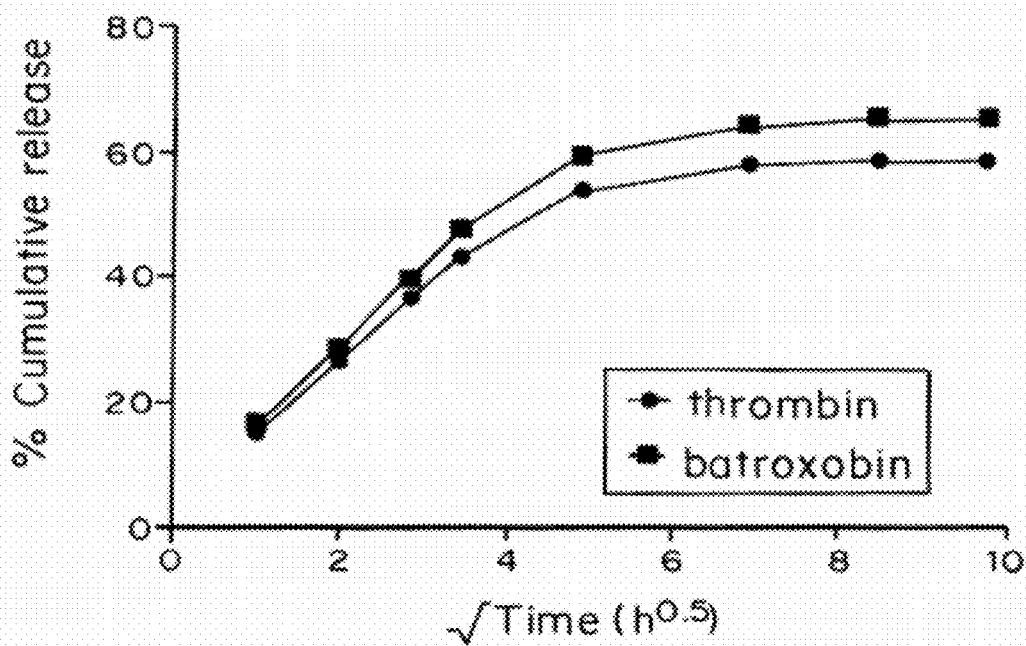
Figure 7C:
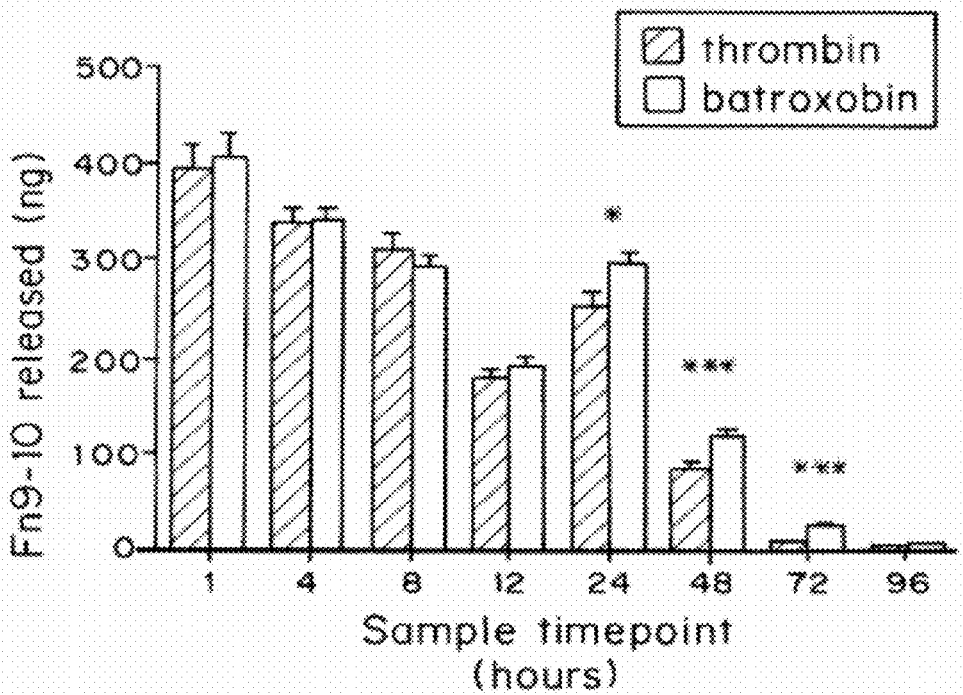
Figure 7D:
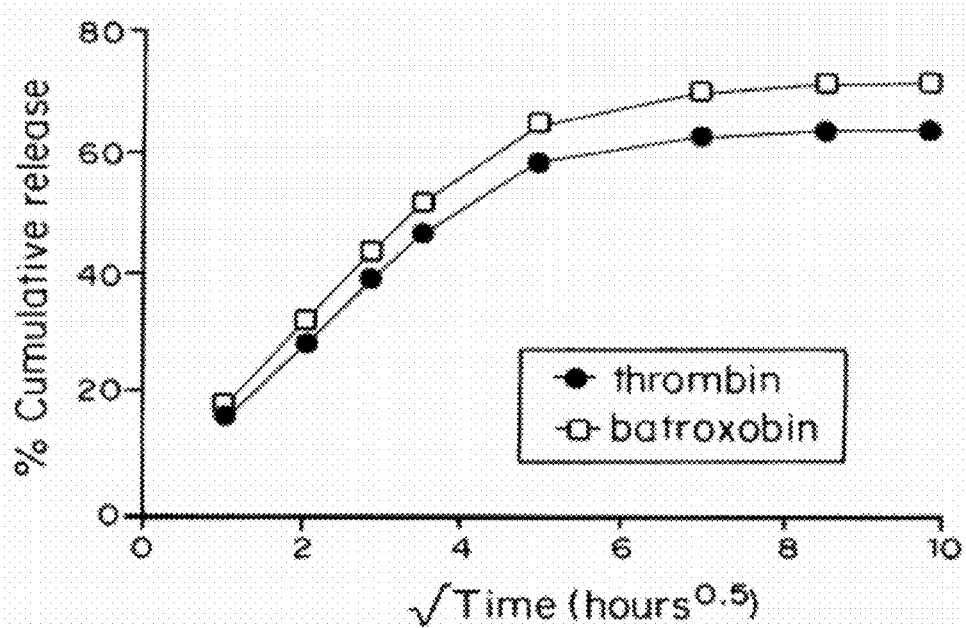

The amount of soluble fibrin(ogen) in all the samples remained below the detection limit (~10 ng/mL) of the fibrin (ogen) ELISA, indicating that the clots remained intact during the four-day incubation period. In the FnIII$_{9-10}$-biotin ELISA, less GPRP-FnIII$_{9-10}$-biotin (SEQ ID NO:1) was released within the first 24 hours as compared to GSPE-FnIII$_{9-10}$-biotin (SEQ ID NO:11) for both the thrombin (FIGS. 6A,B) and batroxobin (FIGS. 6C,D) clots, suggesting that the affinity between GPRP-FnIII$_{9-10}$-biotin (SEQ ID NO:1) and fibrin(ogen) was able to retard the initial 'burst release' of protein from the fibrin matrix, resulting in an overall greater retention of the loaded protein within the clot. Nonetheless, statistical comparisons of the absolute quantity of protein released at each time point did not reveal major differences between GPRP-FnIII$_{9-10}$-biotin (SEQ ID NO:1) and GSPE-FnIII$_{9-10}$-biotin (SEQ ID NO:11) conjugates with respect to the amount of protein released, particularly after the initial 24-hour burst release. Rather, statistically significant differences were found between the amounts of protein released from thrombin-versus batroxobin-catalyzed clots for both GPRP-FnIII$_{9-10}$ (SEQ ID NO:1) (FIG. 7A, B) and GSPE-FnIII$_{9-10}$ (SEQ ID NO:11) (FIG. 7C, D), suggesting that other factors may be involved in mediating protein retention past the 24-hour time point.

Example 6

Evaluating Fusion Protein Retention in Fibrin Matrices Using Perfusion Assays Materials and Methods Perfusion Assays with Confocal Microscopy To examine the retention of knob fusion proteins within fibrin polymer matrices, microfluidic techniques were coupled with confocal microscopy. Microfluidic chamber templates (Y-shaped: 4 cm length, 1 mm width, 60-75 μm height) were fabricated with standard photolithography techniques on silicon wafers. Polydimethylsiloxane (PDMS; Sylgard 184; Dow Corning, Midland, Mich.) was cast onto the silicon wafer template, cured, and removed from the wafer to obtain the microfluidic chambers. Individual PDMS devices were mounted onto clean coverslips immediately after receiving plasma treatment (negative polarization for 1 min at 25 mAmp). Fibrinogen was covalently immobilized to the interior surface of the PDMS channels to promote uniform fibrin matrix formation on all chamber wall surfaces, thereby preventing the separation between the chamber surface and fibrin matrix during perfusion. Briefly, the device channels were treated with 1.5% 3-methacryloxypropyltrimethoxysilane in methanol (20 min), then 0.5% gluteraldehyde (30 min), and then incubated with fibrinogen (100 μg/ml; 30 min). After subsequent rinsing with Tris buffer, a 2 mg/mL fibrinogen solution containing 10% labeled fibrinogen (Alexa Fluor-555; Invitrogen), 1 U/mL thrombin, 1 U/mL factor XIIIa, and labeled Gxxx-FnIII$_{9-10}$ (SEQ ID NO:20) (Alexa Fluor-633; Invitrogen) in a 1:10 molar ratio (Gxxx-FnIII$_{9-10}$:fibrinogen) was injected into the chamber and allowed to polymerize for 1 h. Following polymerization, Tris+Ca buffer was perfused through the chamber at 10 μL/min for 30 min. Confocal z-stack micrographs (2 μm thick stack with 0.5 μm intervals; Zeiss LSM 510) were taken before the Tris+Ca buffer rinse and then every 5 min after commencement of perfusion. Throughout the duration of the experiment and across sample groups, the image acquisition settings remained constant (i.e. pinhole, master gain) for both fluorophores. Colocalization and release of the Gxxx-FnIII$_{9-10}$ (SEQ ID NO:20) was evaluated and quantitated with confocal software ZEN (Carl Zeiss International). Using the colocalization analysis tool in ZEN, baseline thresholds for both fibrin and Gxxx-FnIII$_{9-10}$ (SEQ ID NO:20) signal intensity were held constant for each set of images. Calculated parameters included the relative area of colocalization (colocalized area relative to total area), mean signal intensity for each channel above the threshold, colocalization coefficients for each fluorescent channel (total number of colocalized pixels relative to total number of pixels above the threshold for a given channel; 0=no co-localization and 1=all pixels colocalized), and Pearson's correlation coefficient (R; 1=high correlation; <0=no correlation).

Statistics

All experimental data are reported as mean±SEM of at least 3 independent triplicate experiments. Results were analyzed using GraphPad PRISM 5.0. Statistical comparisons for all experimental sets were based on one-way ANOVA using the Tukey post-hoc test for pair-wise comparisons with significance defined by p<0.05.

Results

A perfusion system was designed to visually examine the real-time dynamics of protein retention within three-dimensional fibrin matrices using confocal microscopy. GPRP-FnIII$_{9-10}$-C (SEQ ID NO:1) (and the control GSPE-FnIII$_{9-10}$-C, SEQ ID NO:11) was fluorescently labeled by conjugation to maleimide-activated Alexa Fluor-633; while fibrinogen was labeled via NHS-amine chemistry with carboxylic acid terminated Alexa Fluor-555. Similar to the release assays, GPRP-FnIII$_{9-10}$-AF633 (SEQ ID NO:1) or GSPE-FnIII$_{9-10}$-AF633 (SEQ ID NO:11) was pre-incubated with fibrinogen at 1:10 molar ratio (conjugate:fibrinogen) for 1 h prior to initiating clot formation with thrombin and factor XIIIa within a microfluidic channel. Confocal images were taken following polymerization (prior to perfusion) and then every five minutes following the initiation of buffer perfusion at a rate of 10 μL/min. According to the confocal micrographs, the GPRP-FnIII$_{9-10}$-AF633 (SEQ ID NO:1) conjugates were incorporated into the fibrin matrix and were retained with in the clots under significant perfusion and slowly released over a span of 30 min at a buffer flow rate of 10 μL/min. Meanwhile GSPE-FnIII$_{9-10}$-AF633 (SEQ ID NO:11) displayed minimal to no fluorescent signal associated with fibrin fibers at any time-point. Colocalization analysis for each set of confocal micrographs further demonstrated that 94.2% of fibrin matrix was initially colocalized with GPRP-FnIII$_{9-10}$ (SEQ ID NO:1) (Table 1), whereas in the negative control only 0.6% fibrin colocalized with GSPE-FnIII$_{9-10}$ (SEQ ID NO:11) (Table 2). These results indicate that the GPRP-FnIII$_{9-10}$ (SEQ ID NO:1) fusion protein, but not GSPE-FnIII$_{9-10}$ (SEQ ID NO:11) was incorporated into the fibrin network. Moreover, 12.8% of the fibrin matrix still retained GPRP-FnIII$_{9-10}$ (SEQ ID NO:1) after undergoing a rigorous perfusion of buffer demonstrating a robust interaction between the fusion protein and fibrin.

TABLE 1

Incorporation and retention of GPRP- FnIII$_{9-10}$

| Time (min) | Mean Intensity | | Relative Area of Colocalization | Colocalization Coefficient | | Correlation Coeffcient (R) |
| --- | --- | --- | --- | --- | --- | --- |
| | Fibrin | GPRP-Fn | | Fibrin | GPRP-Fn | |
| 0 | 100 ± 33 | 100 ± 33 | 94.2% | 0.981 | 0.965 | 0.47 |
| 10 | 105 ± 22 | 55 ± 14 | 28.5% | 0.325 | 0.956 | 0.19 |
| 20 | 105 ± 22 | 52 ± 13 | 19.1% | 0.219 | 0.948 | 0.14 |
| 30 | 99 ± 19 | 51 ± 12 | 12.8% | 0.159 | 0.926 | 0.11 |

TABLE 2

Limited incorporation of GSPE- FnIII$_{9-10}$ in fibrin clots

| Time (min) | Mean Intensity | | Relative Area of Colocalization | Colocalization Coefficient | | Correlation Coeffcient (R) |
| --- | --- | --- | --- | --- | --- | --- |
| | Fibrin | GSPE-Fn | | Fibrin | GSPE-Fn | |
| 0 | 100 ± 39 | 46 ± 6 | 0.6% | 0.01 | 0.739 | 0.04 |
| 10 | 85 ± 23 | 45 ± 5 | 0% | 0.001 | 0.521 | −0.06 |
| 20 | 98 ± 44 | 44 ± 5 | 0.1% | 0.003 | .0413 | 0.02 |
| 30 | 90 ± 38 | 38 ± 6 | 0.1% | 0.003 | 0.377 | −0.02 |

Example 7

Kinetic Binding Models

Materials and Methods

Fibrin Knob 'A' Peptides

Peptide sequences included GPRVVAAC (SEQ ID NO:8), GPRVVERC (SEQ ID NO:7), GPRPAAC (SEQ ID NO:4), GPRPPERC (SEQ ID NO:6), GPRPFPAC (SEQ ID NO:5), and GPSPAAC (SEQ ID NO:9) (GenScript, Inc, Piscataway, N.J.; Table 3). The peptide sequences were designed with a carboxyl-terminal cysteine residue to permit sulfhydryl-targeted reactions for future conjugation chemistries.

TABLE 3

Experimental knob 'A' peptides and corresponding properties

| Peptide Sequence | Property | Net Charge | SEQ ID NO |
|---|---|---|---|
| GPRVVERC | Mimics native sequence through 7th residue | +1 | 7 |
| GPRVVAAC | Mimics native sequence minus additional charged residues | +1 | 8 |
| GPRPAAC | Stabilized backbone | +1 | 4 |
| GPRPFPAC | Stabilized backbone | +1 | 5 |
| GPRPPERC | Stabilized backbone additional charged residues | +1 | 6 |
| GPSPAAC | Negative control Known dysfibrinogen mutant | 0 | 9 |

Preparation of Fibrinogen Fragment D

Human fibrinogen (Enzyme Research Laboratories, South Bend, Ind.) at 2 mg/mL was digested with 0.1 U/mL human plasmin (ERL) in HEPES+$CaCl_2$ buffer (150 mM NaCl, 5 mM $CaCl_2$, 25 mM HEPES; pH 7.4) overnight at room temperature. Fragment D was isolated as previously described, with slight modifications (Kostelansky M S, et al. Biochemistry. 2002; 41(40):12124-12132). Briefly, the plasmin-digested fibrinogen and GPRPAA (SEQ ID NO:10) beads were incubated for 30 min, with occasional agitation. The unbound proteins and protein fragments were removed with excessive washing with HEPES+$CaCl_2$ buffer. Fragment D was eluted with 1M sodium bromide and 50 mM sodium acetate (pH 5.3). Eluted samples were pooled together and exchanged back into HEPES+$CaCl_2$ buffer using a centrifugal filter (MWCO 10,000). Fragment D was verified by SDS-PAGE and stored at −80° C. until use.

Binding Kinetics with Surface Plasmon Resonance (SPR)

The Biacore 2000 (Biacore Lifesciences, GE Healthcare, Pittsburgh, Pa.) was used investigate kinetic binding constants ($k_a$ and $k_d$) of knob 'A' peptide variants for fibrinogen fragment D. Briefly, fragment D was covalently immobilized to gold-coated SPR sensor chips via self-assembled monolayer (SAM) surface chemistry in order to generate a non-fouling surface with a controlled density of reactive carboxylic acid groups. Mixed SAMs were generated on gold-coated chips as described previously (Petrie T A, et al. Biomaterials. 2006; 27(31):5459-5470) by incubating with a 1 mM mixture of tri(ethylene glycol)-terminated alkanethiols (HS-$(CH_2)_{11}$—$(OCH_2CH_2)_3$—OH; $EG_3$; ProChimia, Poland) and carboxylic acid-terminated alkanethiols (HS-$(CH_2)_{11}$—$(OCH_2CH_2)_6$—$OCH_2COOH$; $EG_6$-COOH) for 4 hrs. Upon loading the sensor chip into the Biacore 2000, the $EG_6$-COOH in all four flow cells was activated by flowing 200 mM 1-ethyl-3-(3-dimethylaminopropyl) carbodiimide (EDC; Sigma Aldrich, St. Louis, Mo.) and 50 mM N-hydroxysuccinimide (NHS; Sigma Aldrich) (5 µL/min for 10 min). Immediately following activation, fragment D was immobilized in three flow cells (5 µL/min for 10 min) to achieve 1800-2000 resonance units (RU; 1RU~1 pg/$mm^2$). Unreacted NHS groups were quenched in all four flow cells (three sample cells and one reference cell) with 20 mM ethanolamine (104/min for 10 min). Upon stabilization of the baseline signal, kinetic binding experiments were run in duplicate with the peptide variants as the flow analytes. Five varying concentrations for each peptide (0.94 µM to 150 µM) were flowed at 25 µL/min for 4 min immediately followed by a 10 min dissociation phase. Between each run, the surface was regenerated with 1M sodium bromide and 50 mM sodium acetate (pH 6.0). SPR experiments were performed three times with varying peptide injection order to rule out binding trends associated with injection sequence. Peptide solutions were incubated with tris(2-carboxyethyl)phosphine (TCEP) immobilized on agarose beads (Thermo Fisher Scientific, Inc; Rockland, Ill.) to ensure reduction of any disulfide bonds between C-terminal cysteines. Mass spectrometry analysis (Fast Atom Bombardment) of peptide solutions demonstrated that the peptides did not dimerize over the course of the SPR experiment.

Results

Figure 8A:
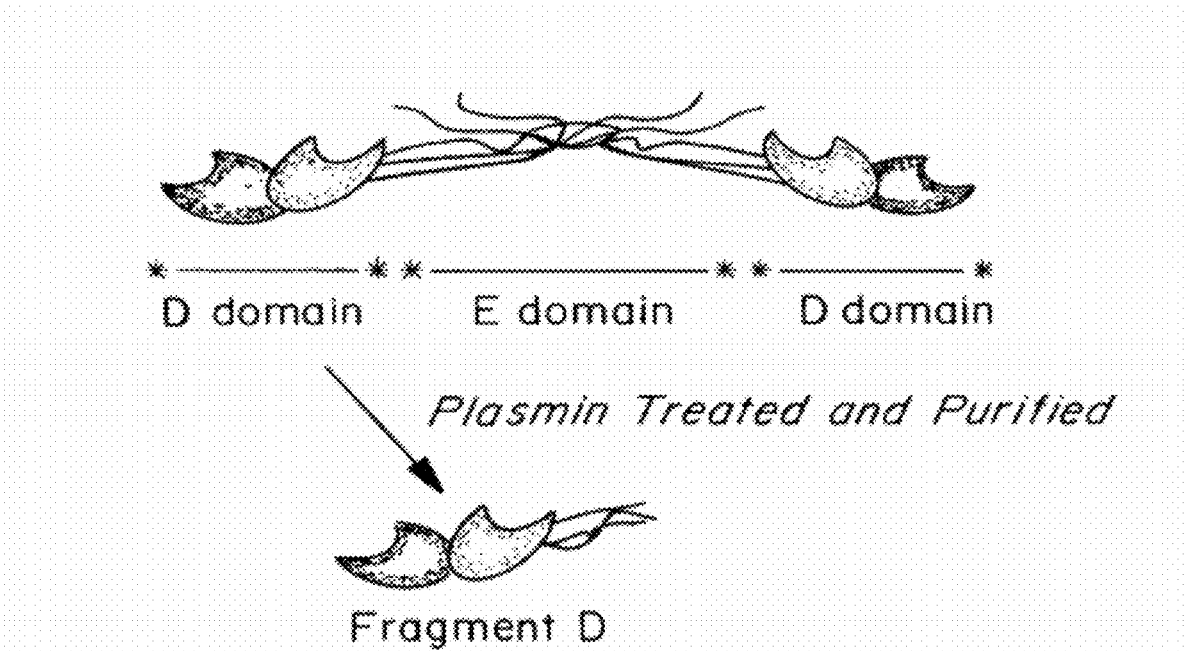
FIG. 8A is a schematic representation of fibrinogen and the two major regions, E and D. Plasmin treated fibrinogen and purification of the fragments generates fragment D.
Figure 8B:
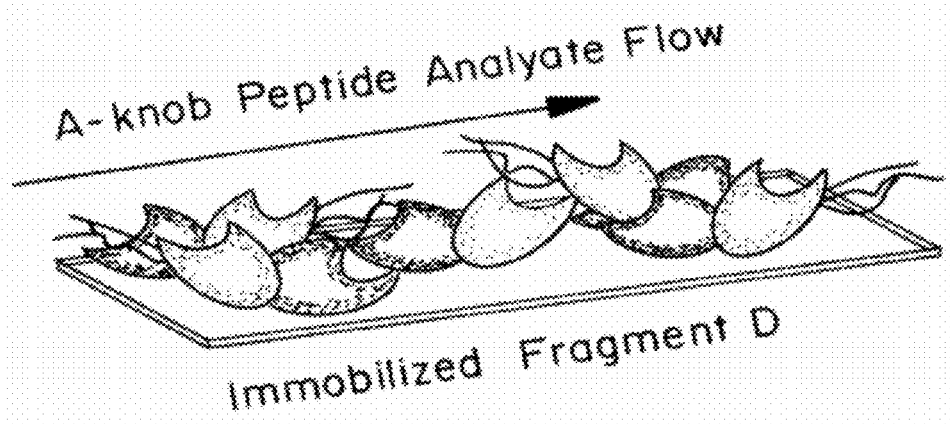
FIG. 8B is a schematic representation of the SPR experimental set-up with fragment D immobilized to an SPR chip acting as the ligand and the knob 'A' peptides flow across the surface as the analyte.
Figure 8C:
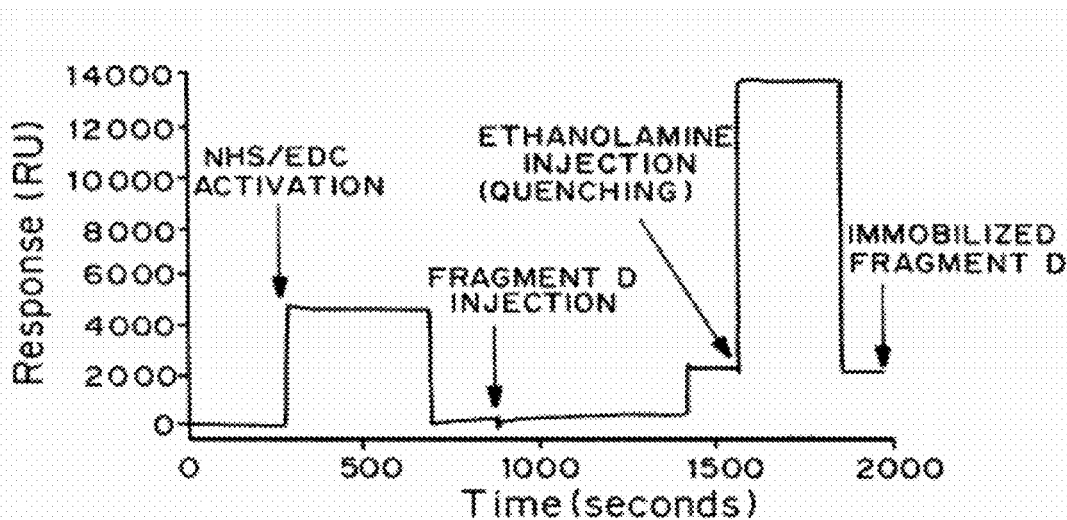
FIG. 8C is a representative SPR line-graph showing protein-protein affinity (RU) of fusion proteins for immobilized fibrinogen fragment D as a function of time (s) where the carboxyl-terminated SAMs were activated by EDC/NHS enabling amine-targeted immobilization of fragment D. Ethanolamine quenched any unreacted carboxyl groups and rid the surface of non-specifically bound fragment D.

To investigate the dynamic binding profile between the fibrinogen/fibrin holes and knob peptide variants, SPR was employed. Binding interactions were evaluated by flowing the knob peptides over an immobilized surface of fragment D (FIG. 8). By immobilizing fragment D as opposed to full-length fibrinogen, the kinetic binding model was simplified to a heterogeneous 2-site ligand model (i.e. one hole 'a' and hole 'b' per ligand) as opposed to a 4-site model (i.e. two of each hole 'a' and hole 'b' per ligand). The data was modeled using both a Langmuir 1:1 model and a heterogeneous ligand model to compare previously established binding affinities to a more dynamic two-site model. However, the complexity of the heterogeneous model fitted parameters for sites 1 and 2 (i.e. maximal binding response, $k_a$, and $k_d$) limits direct designation or assignment of holes 'a' or 'b' to site 1 or 2. An additional mass transport limited model was tested as well, but did not fit the experimental data for any of the peptides. All peptide SPR data was fit except for the negative control peptide, GPSPAAC (SEQ ID NO:9), where minimal binding response was observed.

Figure 9A:
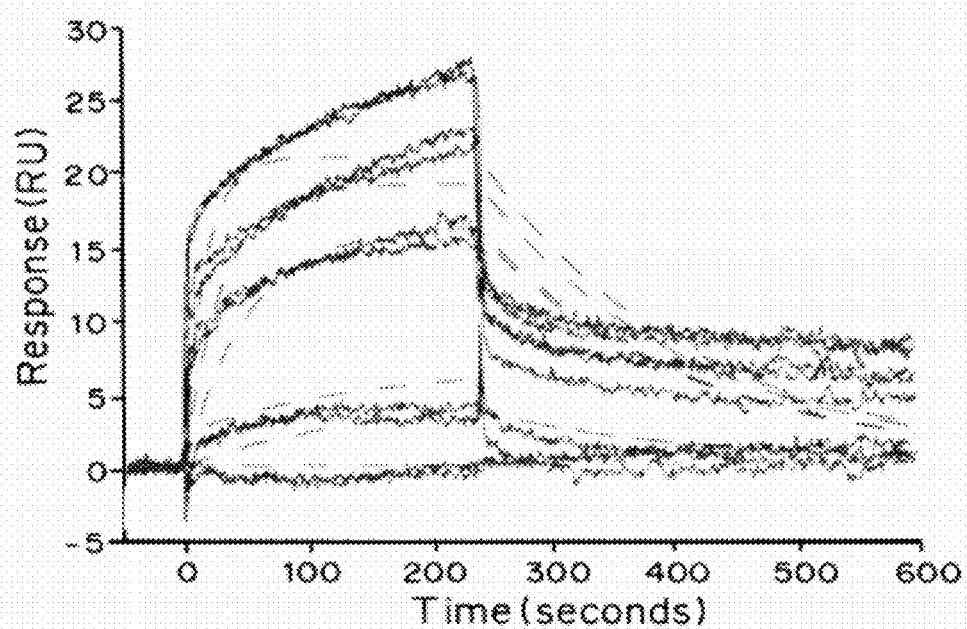
FIGS. 9A and 9B are SPR line-graph showing protein-protein affinity (RU) of GPRPFPAC (SEQ ID NO:5) for immobilized fibrinogen fragment D as a function of time (s) fitted with Langmuir 1:1 model (FIG. 9A) or heterogeneous ligand model (FIG. 9B).
Figure 9B:
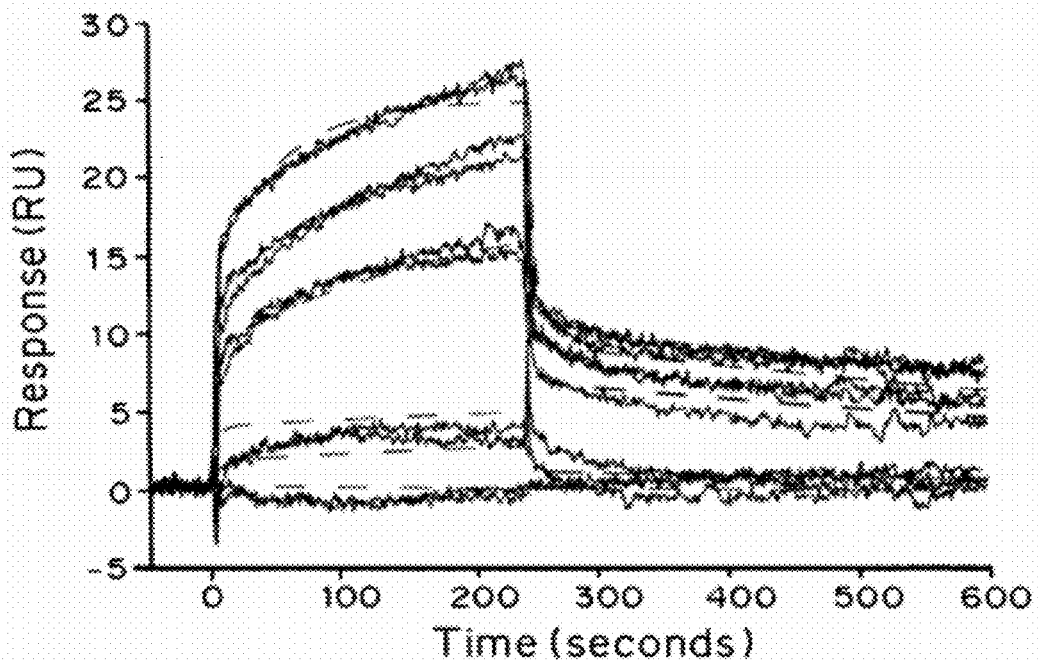
Figure 9C:
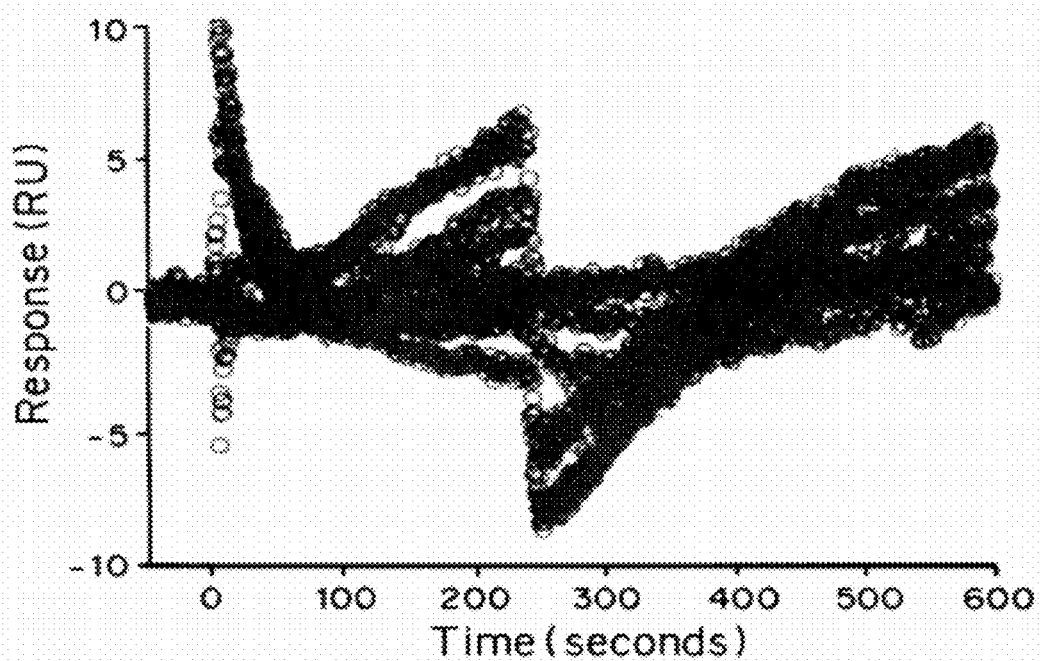
FIGS. 9C and 9D are residual plots corresponding to the Langmuir 1:1 model (FIG. 9C) or heterogeneous ligand model (FIG. 9D). Solid lines=experimental SPR response curves, dashed lines=fitted model curves.
Figure 9D:
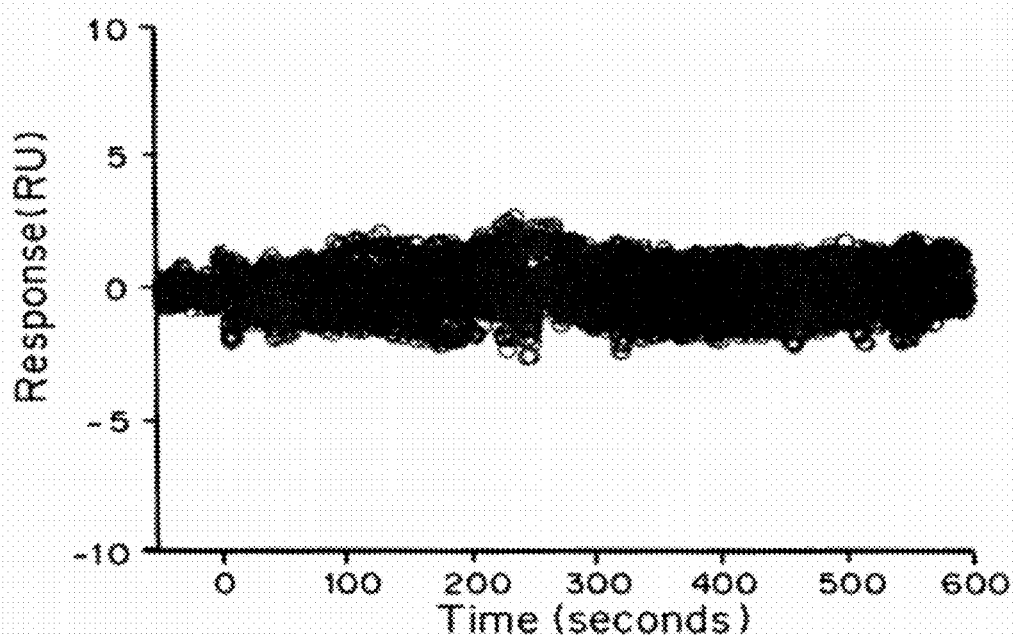

In comparing model simulation results, the heterogeneous ligand model fit the experimental binding data far better than the Langmuir 1:1 model. Response, simulation curves, and residual plots are presented in FIGS. 9, 11 and 12. Looking specifically at the RSS, the range for the 1:1 Langmuir model (1.497 to 2.197; Table 4) was higher than the heterogeneous ligand model (0.9437 to 1.474; Table 5), suggesting that the fitted heterogeneous ligand model deviated less from the experimental data. Additionally, graphically plotting the residuals over time revealed that the residuals for 1:1 Langmuir model followed a systematic trend (FIG. 9C), indicative of fitting an inappropriate model to the experimental data (Cornish-Bowden A. Methods. 2001; 24(2):181-190). In contrast, the residuals for the heterogeneous model were lower and more randomly distributed (FIG. 9D), indicating that this model adequately describes the binding response curves (Morton T A, et al. Methods Enzymol. 1998; 295:268-294;

Cornish-Bowden A. Methods. 2001; 24(2):181-190). Based on these analyses and observations, further comparisons of binding parameters were performed with the results from the heterogeneous ligand model.

TABLE 4

Langmuir 1:1 model - Fitted parameters.

| Parameter | GPRPAAC | GPRPFPAC | GPRPPERC | GPRVVERC | GPRVVAAC |
|---|---|---|---|---|---|
| $B_{max}$ (RU) | 21.47 ± 0.19 | 17.74 ± 0.08 | 19.20 ± 0.21 | 16.27 ± 0.08 | 18.88 ± 0.18 |
| $k_a$ (M-1s-1) × $10^{-3}$ | 1.14 ± 0.03 | 12.5 ± 0.26 | 1.29 ± 0.03 | 0.28 ± 0.004 | 0.09 ± 0.001 |
| $k_d$ (s$^{-1}$) × $10^3$ | 11.71 ± 0.17 | 7.27 ± 0.08 | 9.92 ± 0.13 | 23.43 ± 0.23 | 10.73 ± 0.04 |
| RSS | 2.197 | 2.092 | 1.885 | 1.521 | 1.497 |
| SEQ ID NO: | 4 | 5 | 6 | 7 | 8 |

$B_{max}$ = maximal binding capacity of fragment D (resonance units; RU)
$k_a$ = association rate
$k_d$ = dissociation rate
RSS = residual sum of squares

TABLE 5

Heterogeneous ligand model - Fitted parameters

| Parameter SEQ ID NO: | GPRPAAC 4 | GPRPFPAC 5 | GPRPPERC 6 | GPRVVERC 7 | GPRVVAAC 8 |
|---|---|---|---|---|---|
| $B_{max}$ (RU) | 19.38 ± 0.23 | 17.59 ± 0.13 | 14.58 ± 0.23 | 25.61 ± 0.28 | 8.36 ± 0.24 |
| $k_{a1}$ (M$^{-1}$s$^{-1}$) × $10^{-3}$ | 2.84 ± 0.14 | 21.72 ± 0.73 | 3.22 ± 0.12 | 1.07 ± 0.03 | 0.62 ± 0.04 |
| $k_{d1}$ (s-1) × $10^3$ | 12.83 ± 0.49 | 81.10 ± 2.23 | 58.73 ± 1.86 | 57.67 ± 2.24 | 30.08 ± 1.51 |
| $K_{D1}$ (μM)** | 4.53 | 3.73 | 18.23 | 53.89 | 48.51 |
| $B^*_{max}$ (RU) | 5.91 ± 0.08 | 11.34 ± 0.08 | 5.92 ± 0.13 | 10.33 ± 0.23 | 13.52 ± 0.32 |
| $k_{a2}$ (M$^{-1}$s$^{-1}$) × $10^{-3}$ | 1.05 ± 0.09 | 1.81 ± 0.04 | 1.01 ± 0.03 | 0.26 ± 0.01 | 0.04 ± 0.001 |
| $k_{d2}$ (s$^{-1}$) × $10^3$ | 8.95 ± 1.05 | 1.96 ± 0.04 | 2.96 ± 0.09 | 4.07 ± 0.06 | 1.00 ± 0.07 |
| $K_{D2}$ (μM)** | 8.52 | 1.08 | 2.93 | 15.71 | 25.00 |
| RSS | 1.474 | 0.9887 | 0.9437 | 0.9817 | 1.266 |

$B_{max}$ = maximal binding capacity of fragment D (resonance units; RU)
$k_a$ = association rate
$k_d$ = dissociation rate, RSS = residual sum of squares
**denotes calculated $K_D$ from fitted $k_a$ and $k_d$ values where $K_D = k_d/k_a$ Example 8

Fitted Binding Affinity Parameters

Materials and Methods

SPR Analysis and Evaluation

SPR sensorgrams were analyzed with the aid of Scrubber 2 and ClampXP software (Center for Biomolecular Interactions Analysis, University of Utah) (Morton T A, et al. Methods Enzymol. 1998; 295:268-294; Morton T A, et al. Anal Biochem. 1995; 227(1):176-185; Myszka D G, et al. Trends Biochem Sci. 1998; 23(4):149-150). Prior to analysis, all sensorgrams were inspected for abnormalities (i.e. baseline drift, air spikes, or irregular deviations) and excluded. Reference cell responses were subtracted from corresponding active response curves. Double-referenced curves were acquired by further subtracting the reference cell blank buffer injections from each reference-subtracted response curve (Myszka D G. Mol. Recognit. 1999; 12(5):279-284). All double-referenced curves were normalized by the molecular weight of each peptide and multiplied by 1000 to account for minor variations in response due to molecular weight. The resulting curves were then analyzed and fitted to the kinetic models. Kinetic modeling and simulations were performed with ClampXP software using the Langmuir 1:1 model or the heterogeneous ligand model; globally fitted parameters were determined for each kinetic data set per peptide. Equilibrium binding constants were calculated from fitted kinetic constants. Goodness of fit for each model was determined by evaluating the residual plots and residual sum of squares (RSS) (Myszka D G. J Mol. Recognit. 1999; 12(5):279-284).

Results

Figure 10A:
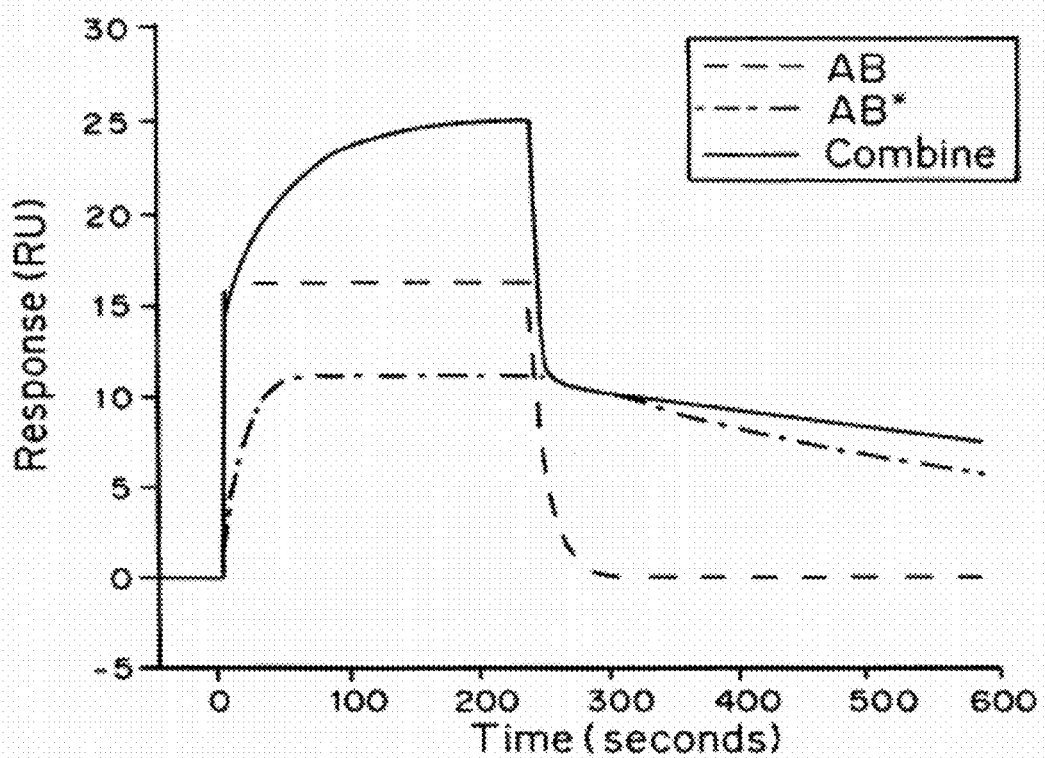
FIG. 10A is a simulated SPR line-graph generated by the heterogeneous ligand model for GPRPFPAC (SEQ ID NO:5). The combine response (solid line) is a sum of analyte-ligand complexes AB (dashed line) and AB* (dash-dot line).

The fitted parameters ($B_{max}$, $k_a$, and $k_d$) for each knob peptide variant for the heterogeneous ligand model are displayed in Table 5. Additionally, the sensorgram plots in FIG. 10A illustrate the contribution each fitted parameter set has on the overall combined 2-site model. For example, for GPRPF-PAC (SEQ ID NO:5), the fit for the AB complex (site 1) encompassed a fast association rate presumably accounting for the large initial response, while the slower association rate for the AB* complex (site 2) contributes to the slower response for the duration of the injection. Broadly comparing all the knob peptide variant parameters, the 4Pro peptides (i.e., GPRPAAC (SEQ ID NO:4), GPRPFPAC (SEQ ID NO:5), and GPRPPERC (SEQ ID NO:6)) had much faster association rates ($k_{a1}$=2.84 to 21.72×10$^3$ M$^{-1}$s$^{-1}$, $k_{a2}$=1.01 to 1.81×10$^3$ M$^{-1}$s$^{-1}$) than the 4Val peptides (i.e., GPRVVAAC (SEQ ID NO:8) and GPRVVERC (SEQ ID NO:7); $k_{a1}$=0.62 to 1.07×10$^3$M$^{-1}$s$^{-1}$, $k_{a2}$=0.04 to 0.26×10$^3$ M$^{-1}$s$^{-1}$).

In comparing the 4Pro variants, one of the most striking differences was the nearly ten-fold increase in $k_{a1}$ for GPRPFPAC (SEQ ID NO:5) (21.72×10$^3$ M$^{-1}$s$^{-1}$) compared to GPRPAAC (SEQ ID NO:4) (2.84×10$^3$ M$^{-1}$s$^{-1}$s$^{-1}$) and GPRPPERC (SEQ ID NO:6) (3.22×10$^3$ M$^{-1}$s$^{-1}$); however for $k_{d1}$, GPRPAAC (SEQ ID NO:4) (12.83×10$^{-3}$ s$^{-1}$) displayed a six-fold slower rate compared to GPRPFPAC (SEQ ID NO:5) (81.10×10$^{-3}$ s$^{-1}$). In contrast, for the second binding site the $k_{a2}$ rate for GPRPFPAC (SEQ ID NO:5) (1.81×10$^3$ M$^{-1}$s$^{-1}$) was only moderately faster than GPRPAAC (SEQ ID NO:4) (1.05×10$^3$ M$^{-1}$s$^{-1}$) and GPRPPERC (SEQ ID NO:6) (1.01× 10$^3$ M$^{-1}$s$^{-1}$), while the $k_{d2}$ for GPRPFPAC (SEQ ID NO:5) (1.96×10$^{-3}$ s$^{-1}$) was nearly eight-fold slower than GPRPAAC (SEQ ID NO:4) (8.95×10$^{-3}$ s$^{-1}$). These simulation results indicate that GPRPFPAC (SEQ ID NO:5) has a higher affinity to the first and second binding sites and additionally dissociates more slowly from the second binding site, thus translating to longer engagement in fibrinogen holes compared to the other variants tested.

The impact additional charged residues in the sixth and seventh position had on functional binding characteristics was also investigated by comparing GPRVVAAC (SEQ ID NO:8) and GPRVVERC (SEQ ID NO:7). For the association rates, GPRVVERC (SEQ ID NO:7) had a two-fold increase over GPRVVAAC (SEQ ID NO:8) in $k_{a1}$ (1.07×10$^3$ M$^{-1}$s$^{-1}$ vs. 0.62×10$^3$ M$^{-1}$s$^{-1}$, respectively) and a six-fold increase in $k_{a2}$, (0.26×10$^3$ M$^{-1}$s$^{-1}$ vs. 0.04×10$^3$ M$^{-1}$s$^{-1}$, respectively). However, the dissociation rates for GPRVVERC (SEQ ID NO:7) were two-fold faster than GPRVVAAC (SEQ ID NO:8) for $k_{d1}$ (57.67×10$^{-3}$ s$^{-1}$ vs 30.08×10$^{-3}$ s$^{-1}$, respectively) and four-fold faster for $k_{d2}$ (4.07×10$^{-3}$ s$^{-1}$ vs 1.00× 10$^{-3}$ s$^{-1}$, respectively). These results collectively imply that while the additional charged residues (i.e., 6Glu and 7Arg) may enhance the affinity of the knob peptide to the binding holes, it may also result in an increased rate of dissociation.

Example 9

Equilibrium Dissociation Constants

Results

Figure 10B:
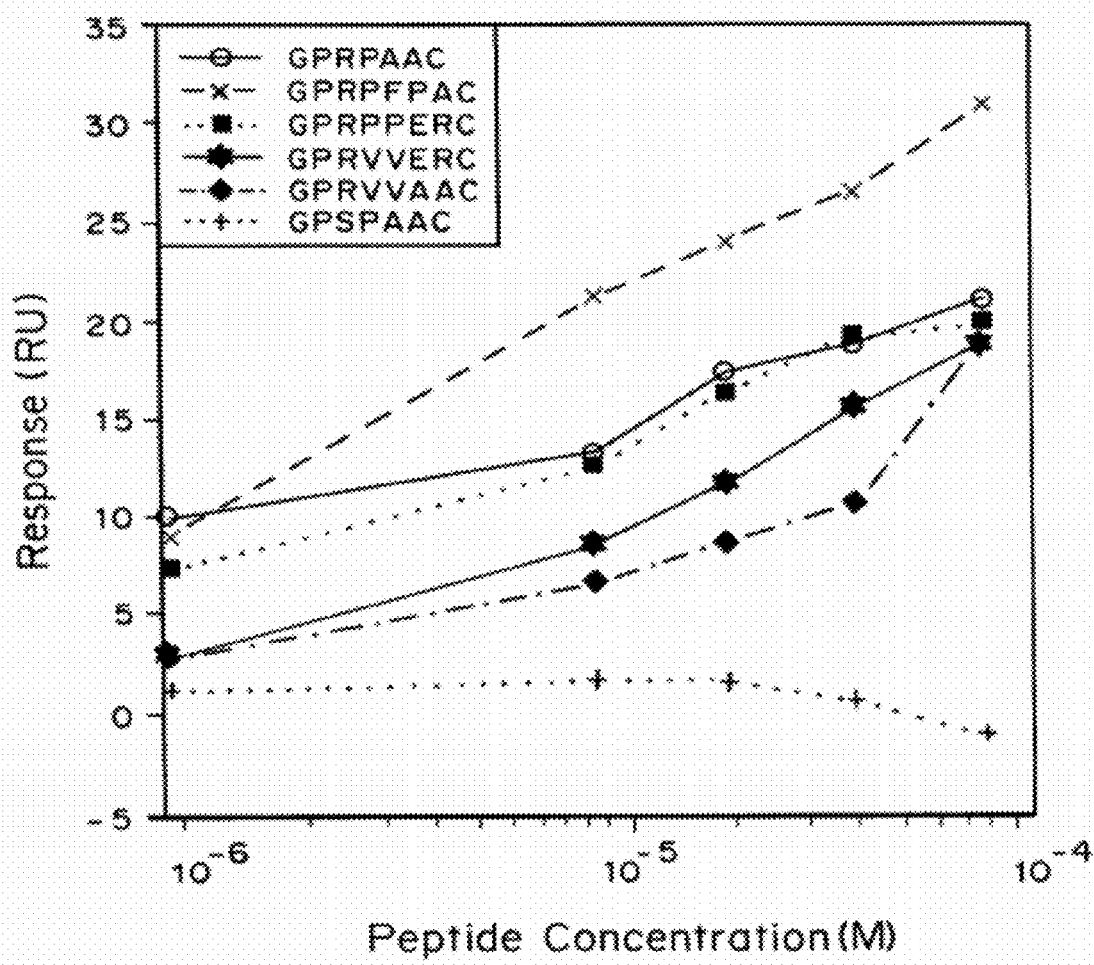
FIG. 10B is an SPR line-graph showing Maximal binding response (RU) of GPSPAAC (SEQ ID NO:9, "+"), GPRPAAC (SEQ ID NO:4, open circle), GPRPFPAC (SEQ ID NO:5, "x"), GPRPPERC (SEQ ID NO:6, closed square), GPRVVERC (SEQ ID NO:7, open square), and GPRVVAAC (SEQ ID NO:8, diamond) for immobilized fibrinogen fragment D as a function of peptide concentration (M).
Figure 11A:
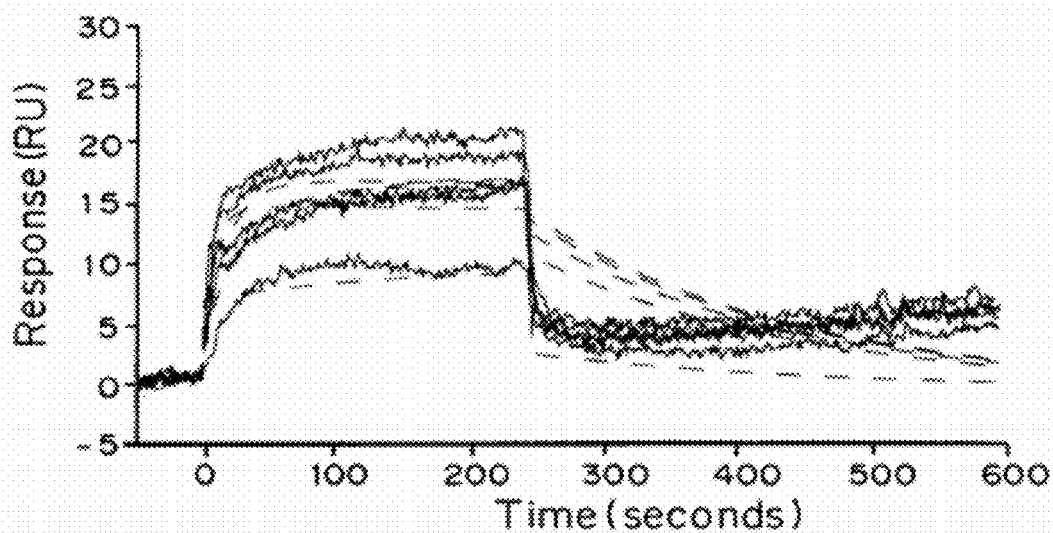
FIGS. 11A-11J are SPR line-graphs (11A, 11C, 11E, 11G, and 11I) and residual plots (11B, 11D, 11F, 11H, and 11J) showing protein-protein affinity (RU) of GPRPAAC (SEQ ID NO:4, FIGS. 11A and 11B), GPRPFPAC (SEQ ID NO:5, FIGS. 11C and 11D), GPRPPERC (SEQ ID NO:6, FIGS. 11E and 11F), GPRVVERC (SEQ ID NO:7, FIGS. 11G and 11H), and GPRVVAAC (SEQ ID NO:8, FIGS. 11I and 11J) for immobilized fibrinogen fragment D as a function of time (s) fitted with Langmuir 1:1 model. Solid lines=experimental SPR response curves, dashed lines=fitted model curves.
Figure 11B:
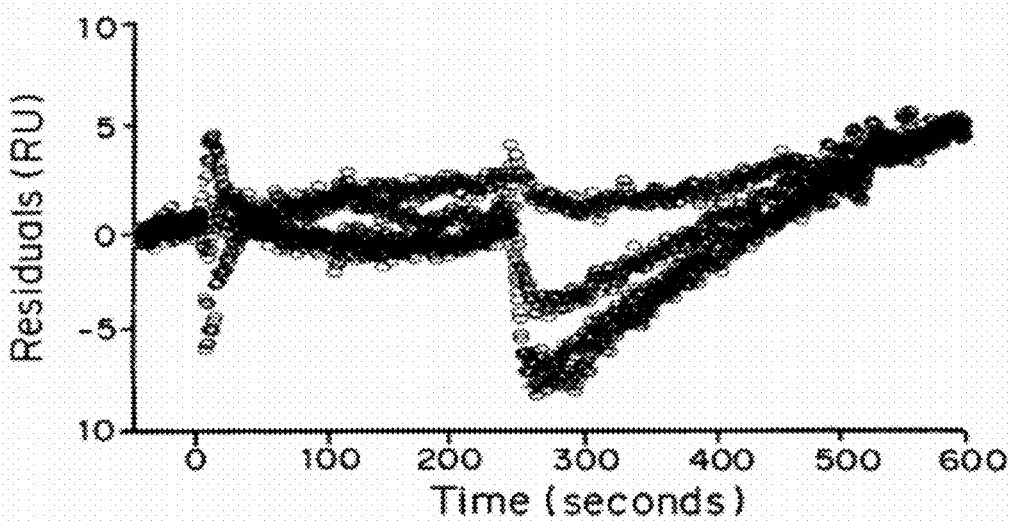
Figure 11C:
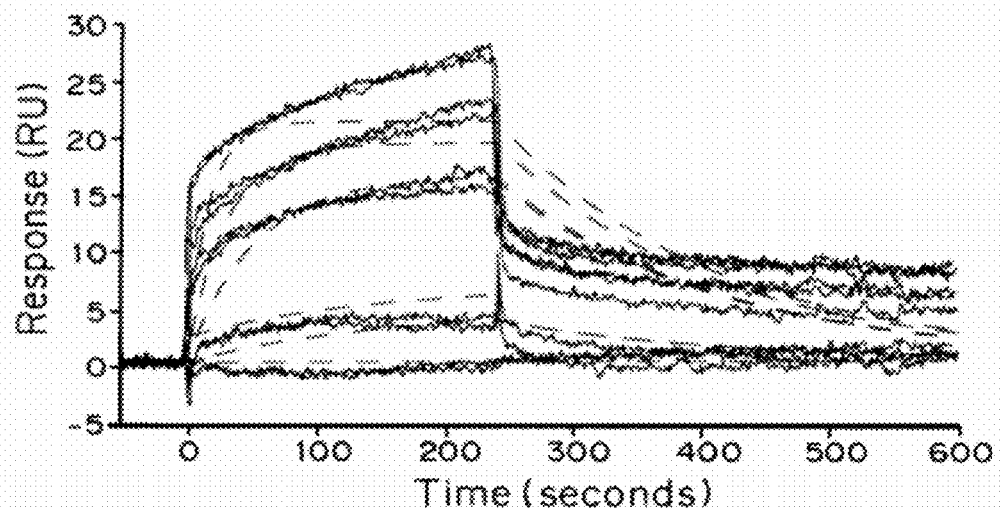
Figure 11D:
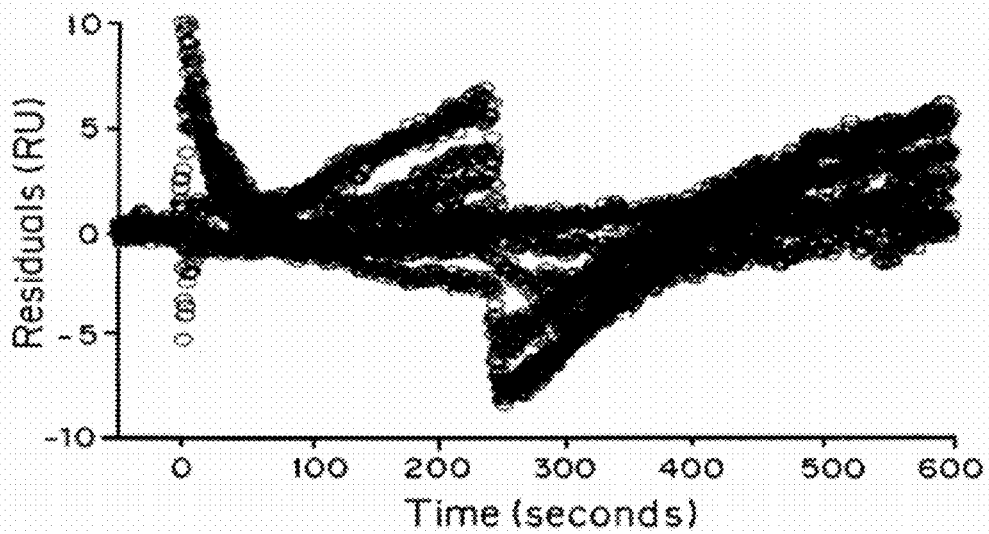
Figure 11E:
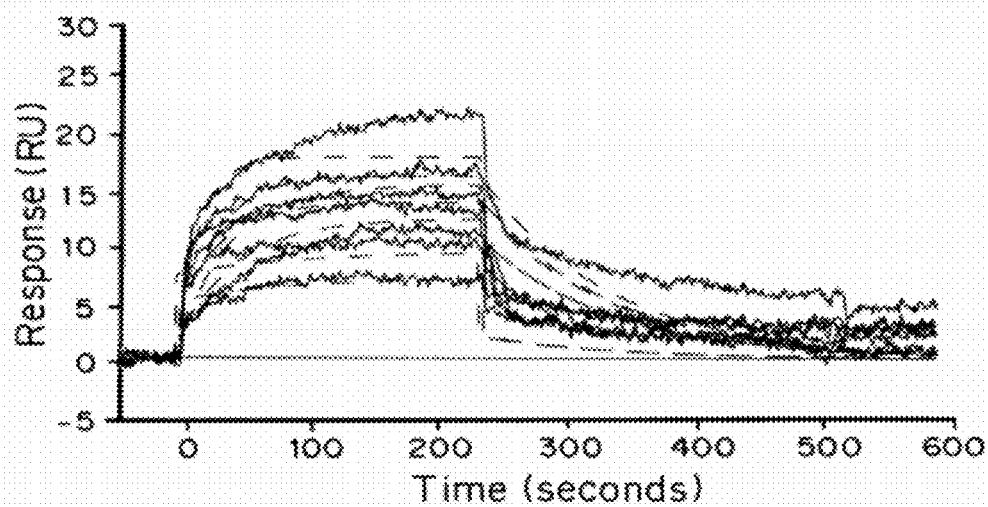
Figure 11F:
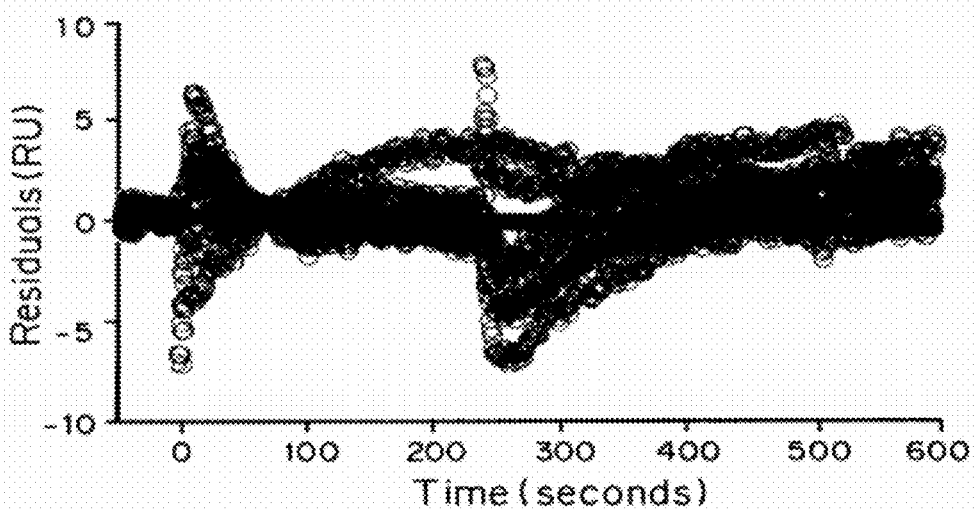
Figure 11G:
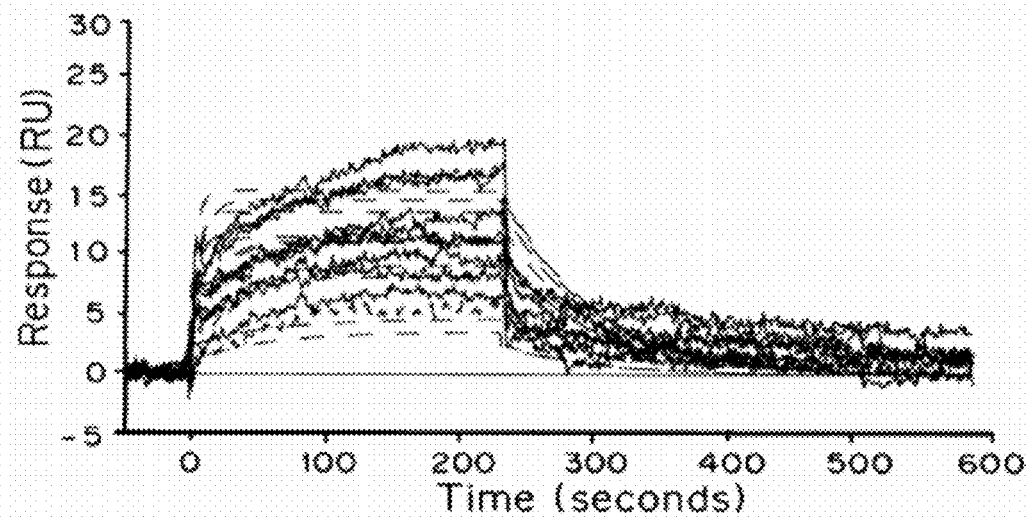
Figure 11H:
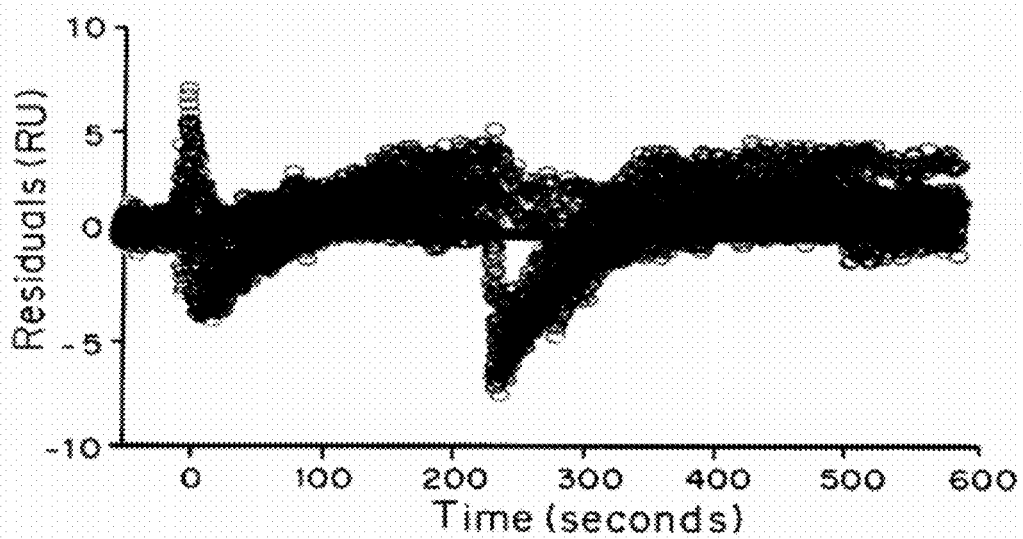
Figure 11I:
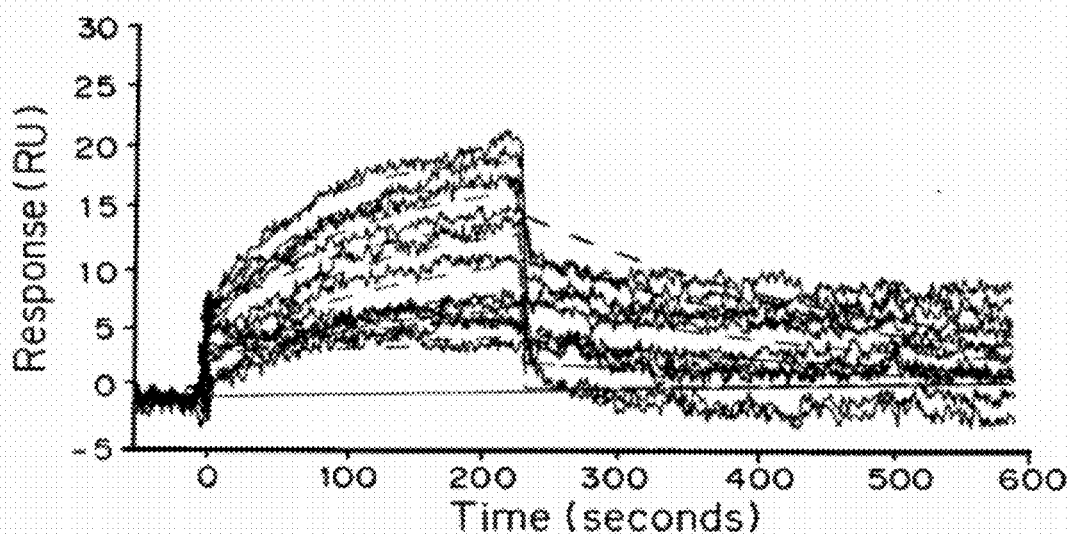
Figure 11J:
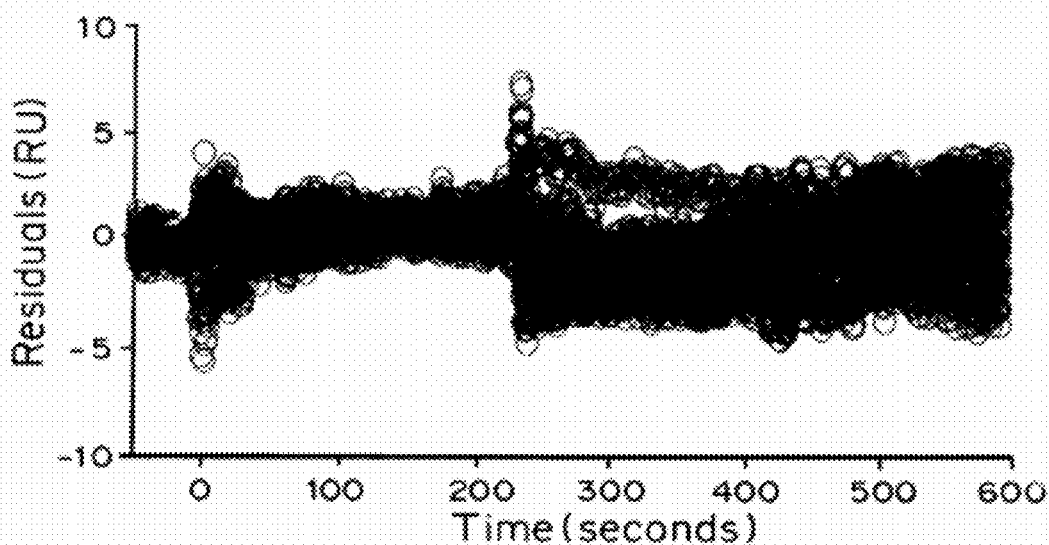
Figure 12A:
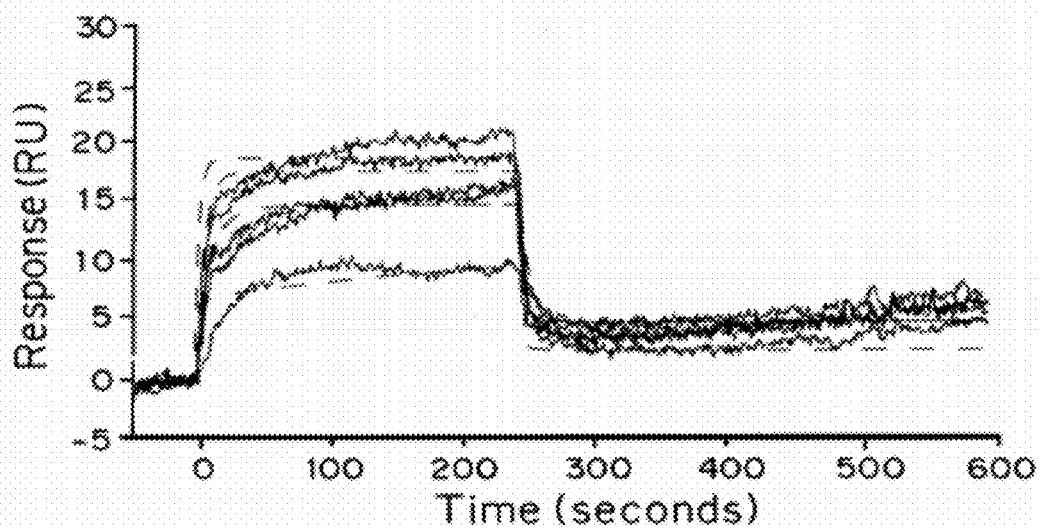
FIGS. 12A-12J are SPR line-graphs (12A, 12C, 12E, 12G, and 12I) and residual plots (12B, 12D, 12F, 12H, and 12J) showing protein-protein affinity (RU) of GPRPAAC (SEQ ID NO:4, FIGS. 12A and 12B), GPRPFPAC (SEQ ID NO:5, FIGS. 12C and 12D), GPRPPERC (SEQ ID NO:6, FIGS. 12E and 12F), GPRVVERC (SEQ ID NO:7, FIGS. 12G and 12H), and GPRVVAAC (SEQ ID NO:8, FIGS. 12I and 12J) for immobilized fibrinogen fragment D as a function of time (s) fitted with heterogenous ligand model. Solid lines=experimental SPR response curves, dashed lines=fitted model curves.
Figure 12B:
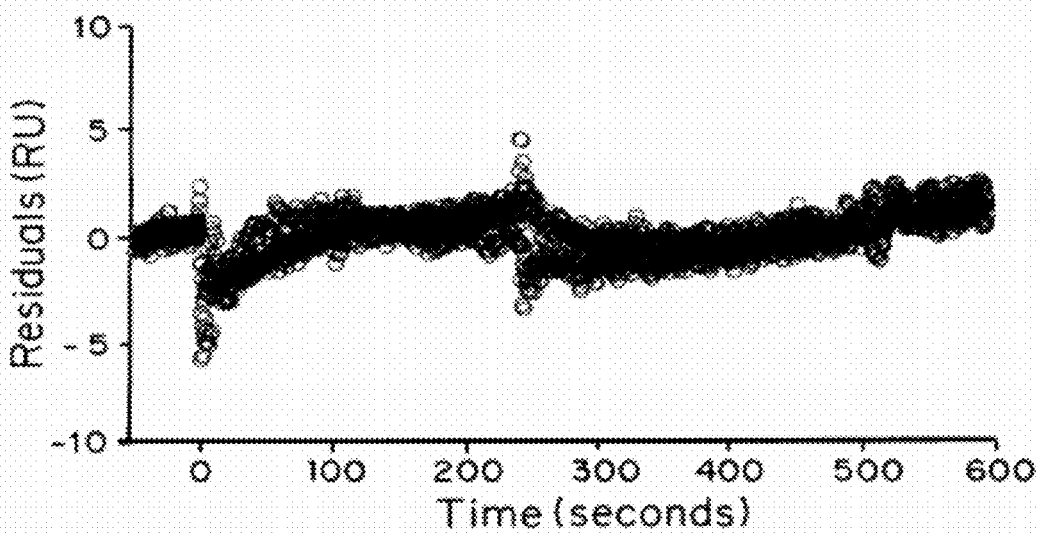
Figure 12C:
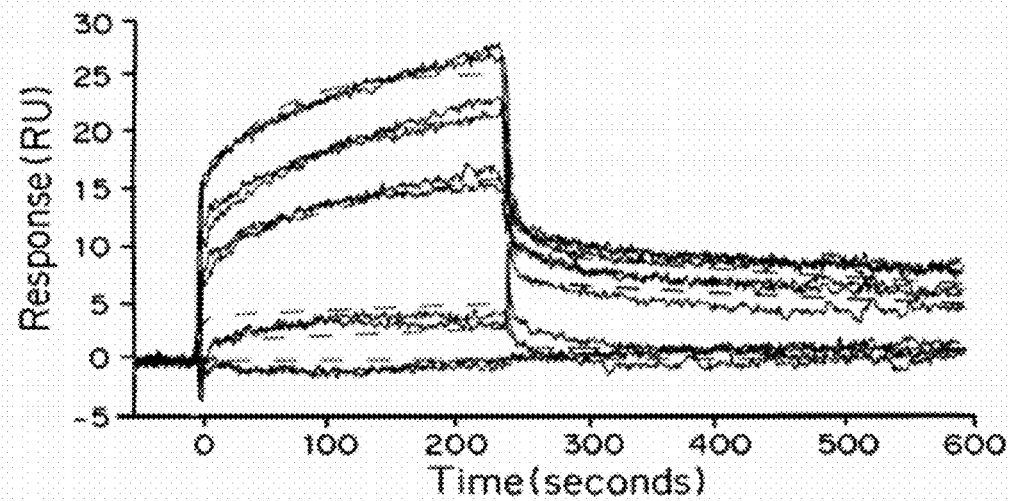
Figure 12D:
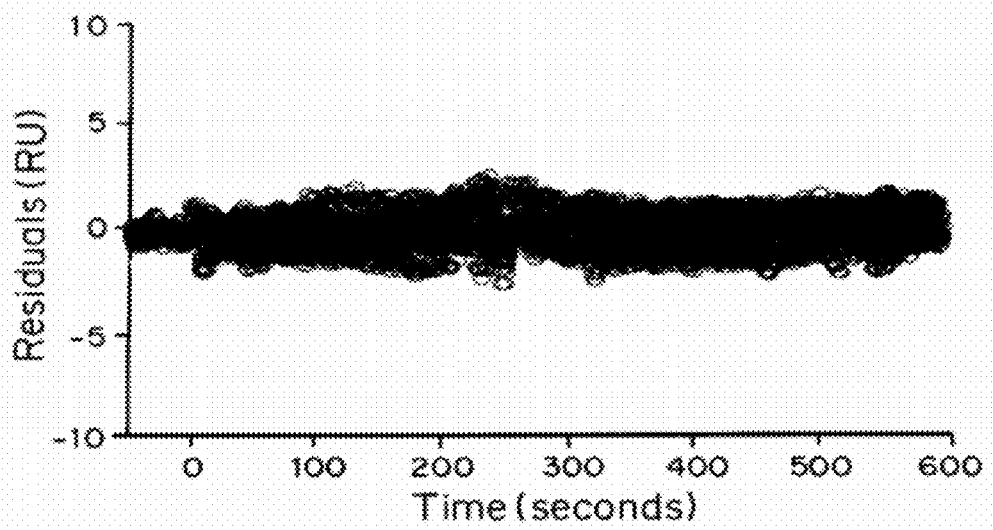
Figure 12E:
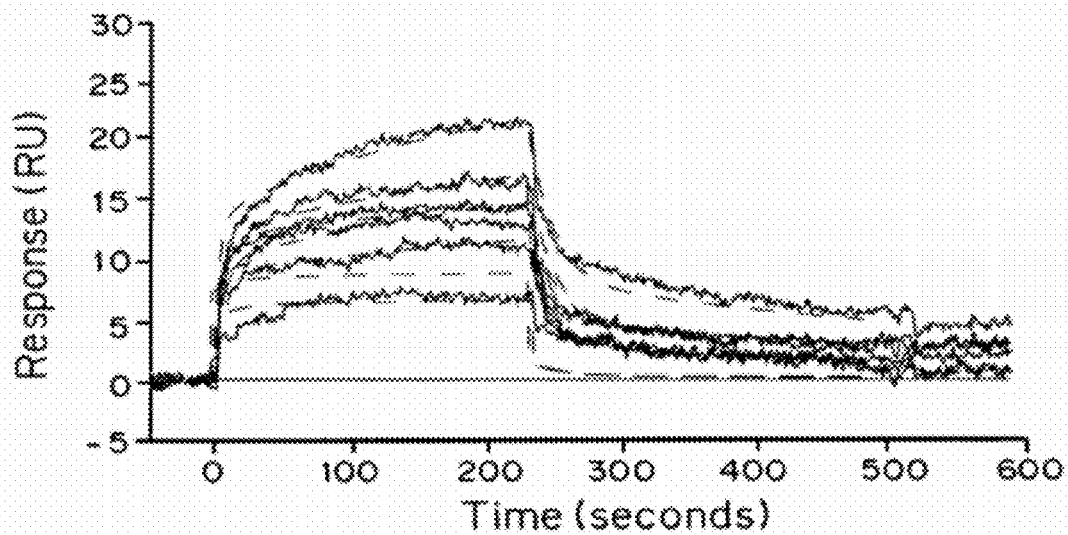
Figure 12F:
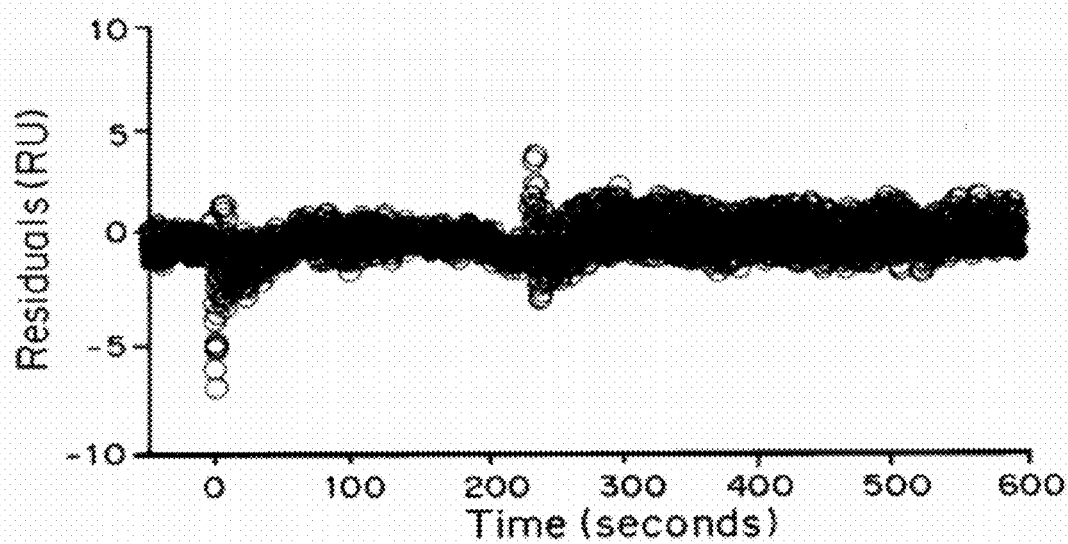
Figure 12G:
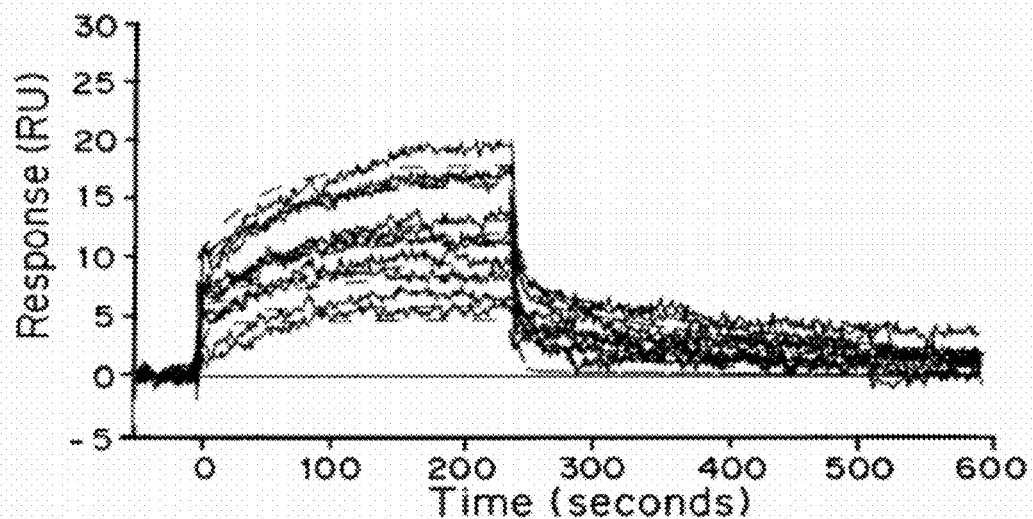
Figure 12H:
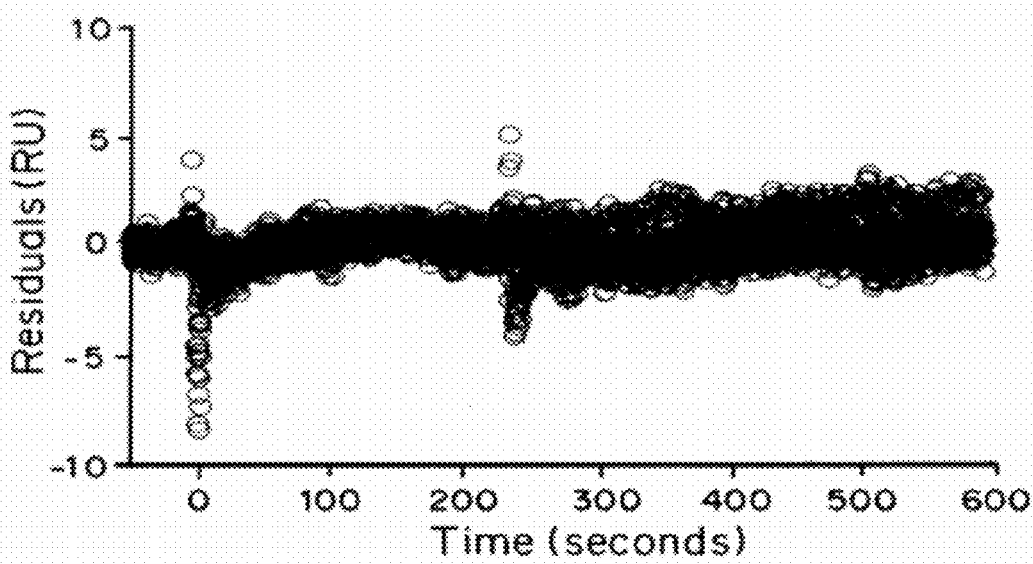
Figure 12I:
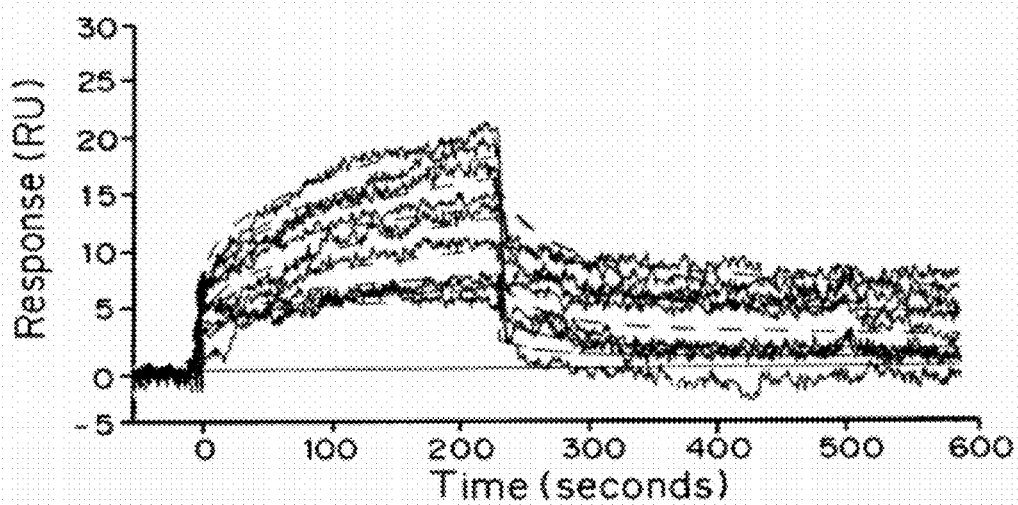
Figure 12J:
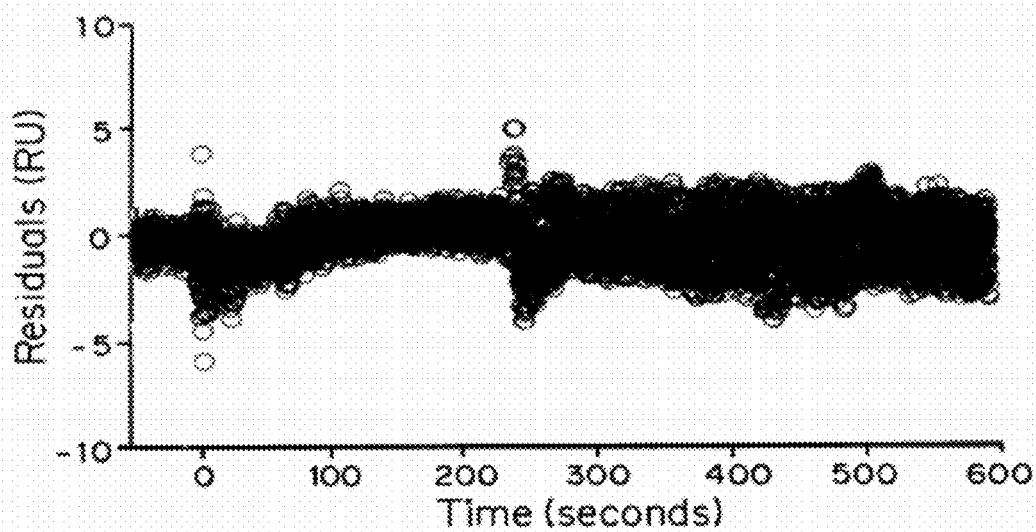
Figure 13A:
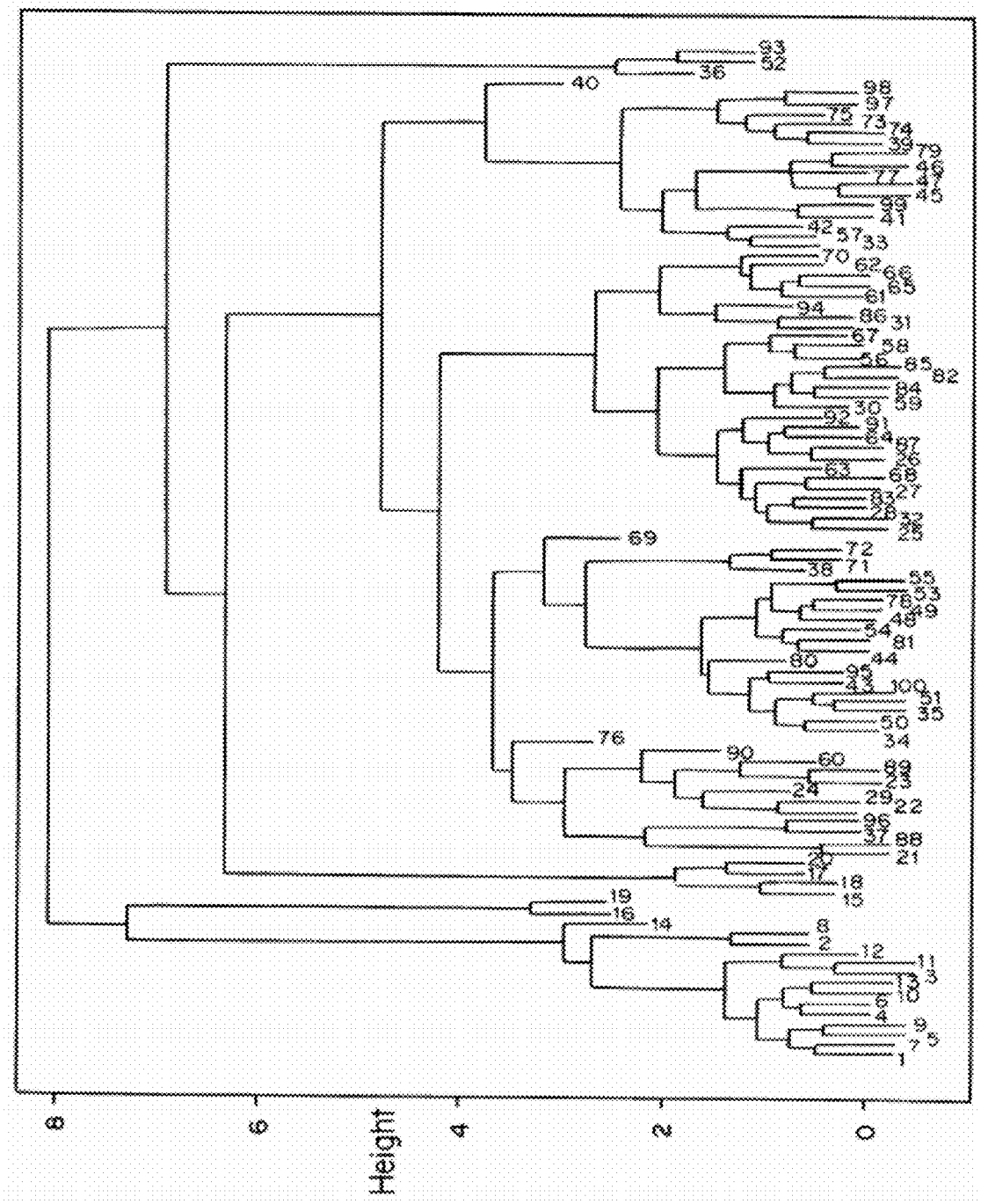
FIGS. 13A-E are dendrograms from hierarchical cluster analysis from a dissimilarity matrix generated from the Root mean squared deviation (RMSD) between every frame in the trajectory for GPRPFPAC (SEQ ID NO:5, FIG. 13A), GPRVVAAC (FIG. 13B, SEQ ID NO:8), GPRPAAC (SEQ ID NO:4, FIG. 13C), GPRPPERC (SEQ ID NO:6, FIG. 13D), and GPRVVERC (SEQ ID NO:7, FIG. 13E).
Figure 13B:
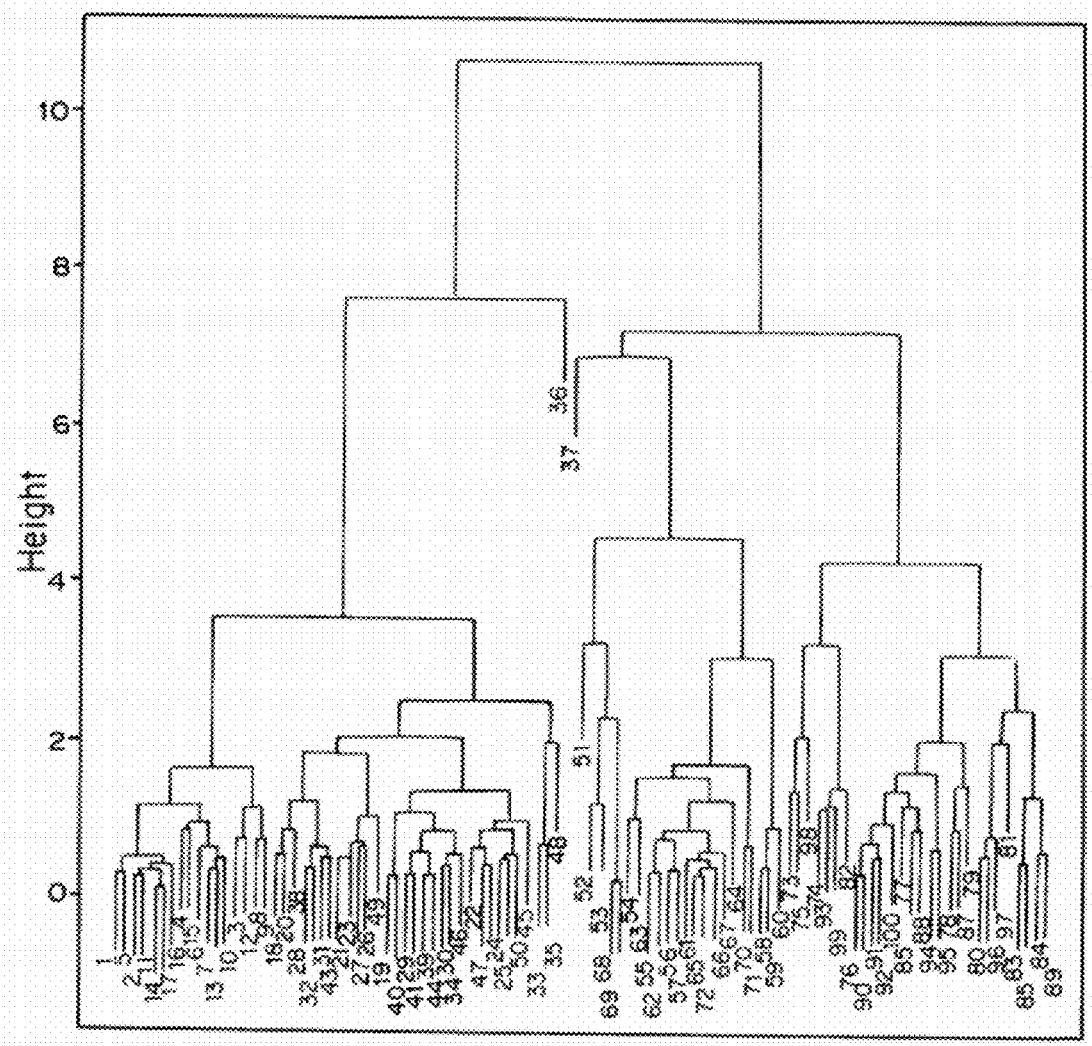
Figure 13C:
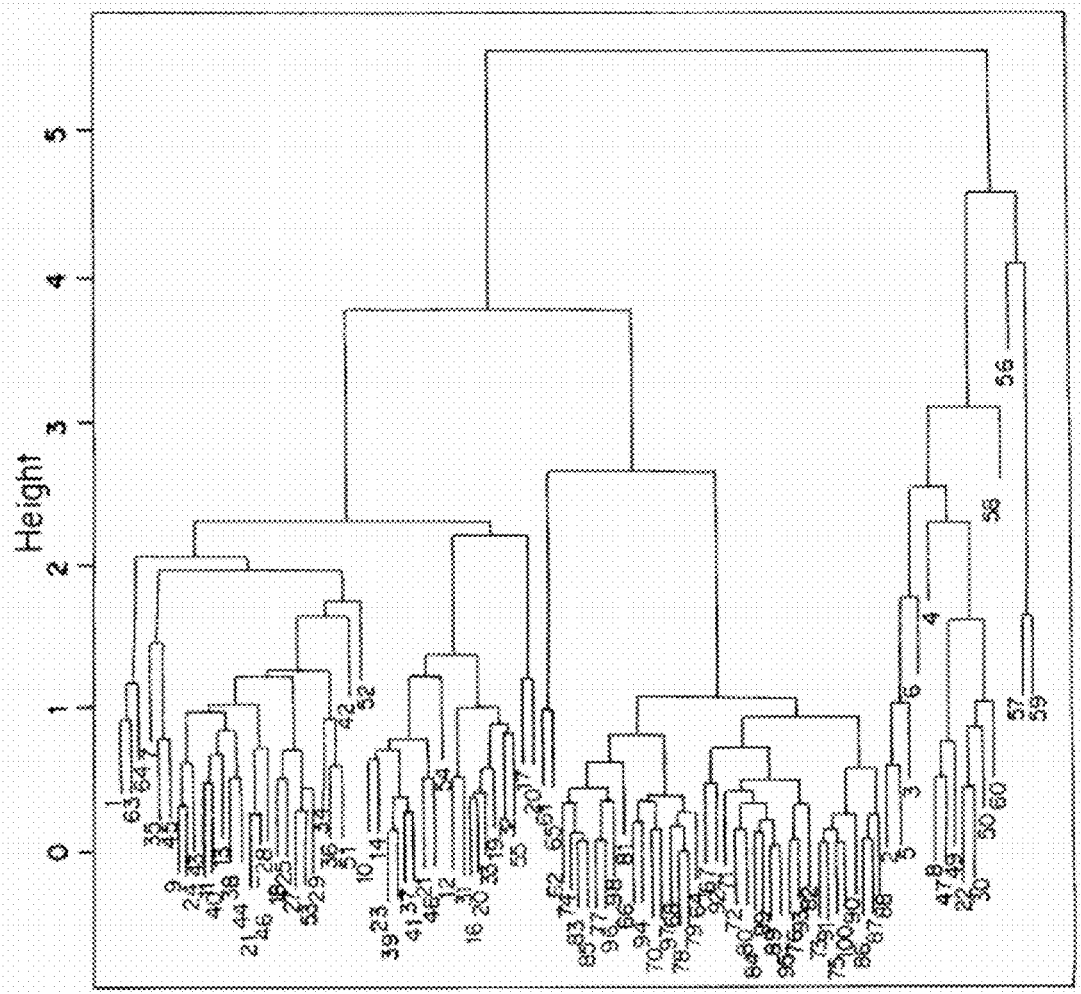
Figure 13D:
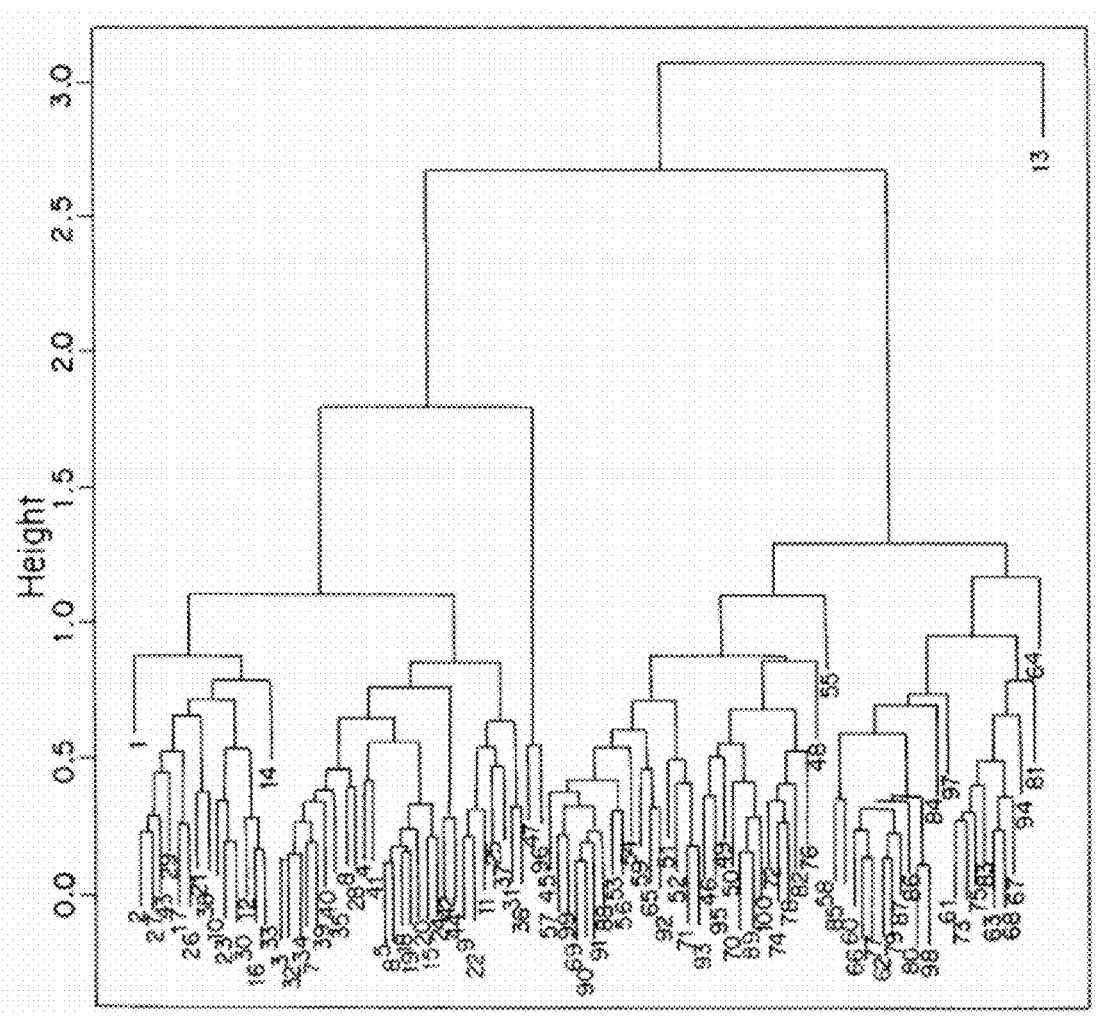
Figure 13E:
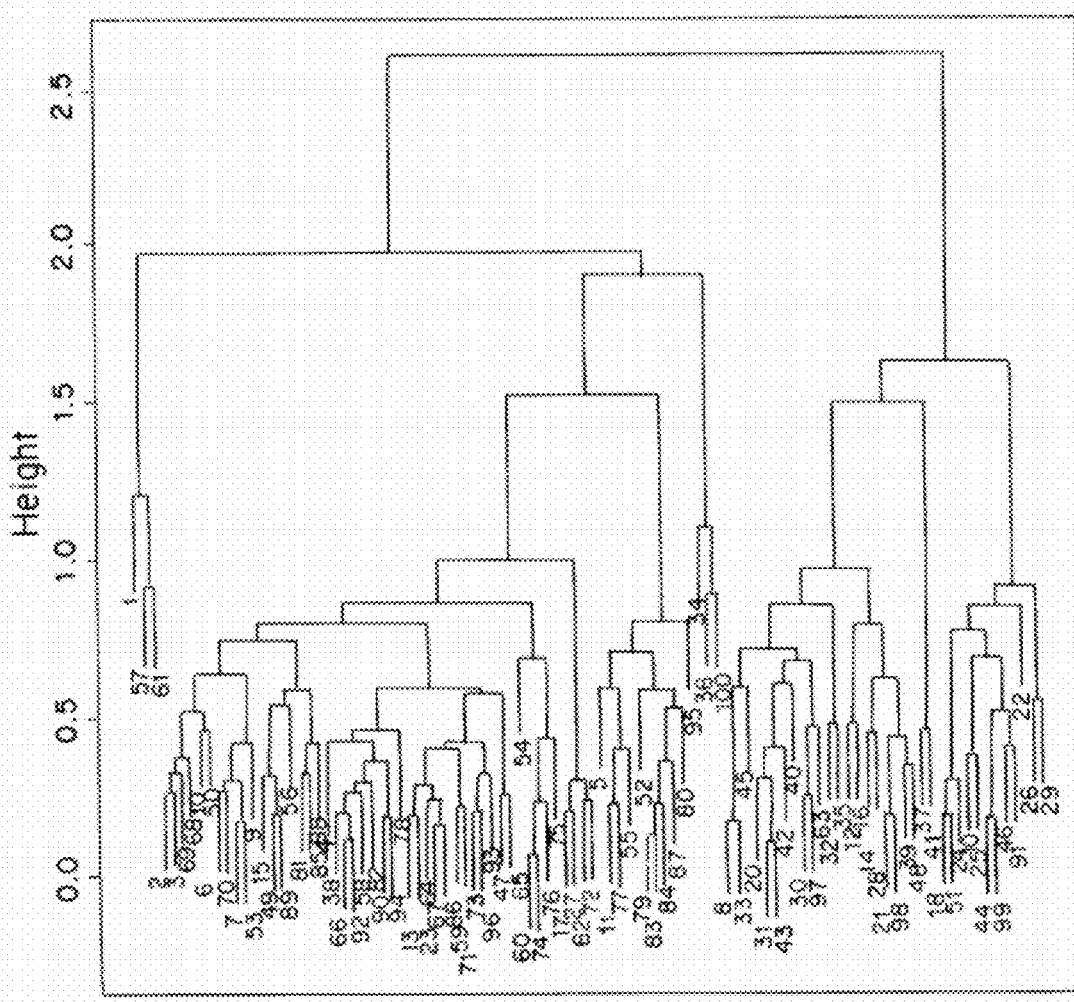

Using the fitted $k_a$s and $k_d$s from the kinetic models, the equilibrium dissociation constants were calculated ($K_D$s; Table 5). These results are also represented graphically by plotting the SPR binding maximum for each variant versus injection concentration (FIG. 10B). The lowest $K_D$s were observed in the peptide variants with a 4Pro (GPRPFPAC (SEQ ID NO:5)<GPRPAAC (SEQ ID NO:4)<GPRPPERC (SEQ ID NO:6)<GPRVVERC (SEQ ID NO:7)<GPRVVAAC (SEQ ID NO:8)). In comparing the specific $K_D$s for the each site between the 4Pro variants, $K_{D1}$ for GPRPFPAC (SEQ ID NO:5) (3.73 µM) and GPRPAAC (SEQ ID NO:4) (4.53 µM) was significantly lower than GPRPPERC (SEQ ID NO:6) (18.23 µM). However, for the second site, the $K_{D2}$ values for GPRPFPAC (SEQ ID NO:5) (1.08 µM) and GPRPPERC (SEQ ID NO:6) (2.93 µM) were significantly lower than GPRPAAC (SEQ ID NO:4) (8.52 µM). This result further indicates that GPRPFPAC (SEQ ID NO:5) interacts and engages the hole domains more readily than the other variants tested, even the gold standard GPRP (SEQ ID NO:1) mimic (GPRPAAC, SEQ ID NO:4). In comparing GPRVVAAC (SEQ ID NO:8) to GPRVVERC (SEQ ID NO:7), the addition of charged residues, 6Glu and 7Arg, decreased $K_{D2}$ from 25.00 µM to 15.71 µM, while $K_{D1}$ was relatively similar.

Example 10

Molecular Dynamics Simulation Analysis

Materials and Methods

Molecular Dynamics (MD) Simulations

Classical MD simulations were performed with five knob 'A' peptides, GPRVVAAC (SEQ ID NO:8), GPRVVERC (SEQ ID NO:7), GPRPAAC (SEQ ID NO:4), GPRPPERC (SEQ ID NO:6), and GPRPFPAC (SEQ ID NO:5). Since the crystal structure of each of these peptides within the fibrin hole has not been determined experimentally, the initial peptide structures were rendered in Swiss-PDB Viewer (Swiss Institute of Bioinformatics, Guex N, et al. Electrophoresis. 1997; 18(15):2714-2723) with the backbone torsion angles of the first three residues constrained to an 'active' peptide conformation obtained from previously published fragment D crystal structures (PDB code: 2HPC and 2FFD, Betts L, et al. Journal of Thrombosis and Haemostasis. 2006; 4(5):1139-1141). Prior to MD simulations, the structure of each peptide was minimized with 10 iterations of steepest descent (500 steps) energy minimization in vacuo. Each peptide was placed in the center of a water box (Visual Molecular Dynamics software, Humphrey W, et al. J Mal Graph. 1996; 14(1): 33-38, 27-38) supplemented with Na$^+$ and Cl$^-$ ions to achieve electric neutrality, mimicking experimental conditions (~340 mOsmol/L). The models were initially minimized for 1000 steps with the backbone atoms fixed, followed by 1000 steps of minimization with harmonic restraints on the alpha carbon atoms. After energy minimization, each system was heated to 310K over a period of 20 ps with harmonic restraints on the alpha carbons. Next, with the restraints still active, each system was equilibrated at constant temperature (310K) and pressure (1 atm) for 100 ps. The restraints were then removed, and the equilibration was continued for 200 ps. The production runs were carried out for 10 ns under constant temperature and pressure conditions, i.e. the NPT ensemble. Temperature was maintained at 310K, pressure at 1 atm. Short-range non-bonded interactions were cut off at a distance of 12 Å with a switching function between 10 and 12 Å. The particle mesh Ewald method was used to compute electrostatics (Darden T, et al. Journal of Chemical Physics. 1993; 98(12): 10089-10092). All bonds involving hydrogen atoms were constrained using the SHAKE algorithm (Ryckaert J P, et al. Journal of Computational Physics. 1977; 23(3):327-341), which allowed for an integration time step of 2fs. All simulations were performed with NAMD Version 2.6 (Theoretical and Computational Biophysics Group at University of Illinois at Urbana-Champaign, Phillips J C, et al. Journal of Computational Chemistry. 2005; 26(16):1781-1802) using the CHARMM22 force field parameter set (MacKerell A D, et al. Journal of Physical Chemistry B. 1998; 102(18):3586-3616).

Clustering Analysis

A hierarchical cluster analysis was performed on the trajectory data from each peptide MD simulation. A trajectory for clustering was obtained by taking every 100th frame (100 ps interval) from a 10 ns production run. Next, we calculated the root mean squared deviation (RMSD) between every frame in the trajectory to generate a dissimilarity matrix. RMSD was calculated based on the backbone atoms after optimal superposition. The agnes function in the cluster package supplied with the R statistical software package was used to construct a hierarchy of clusterings from the dissimilarity matrix. The clusters were visualized in VMD using the Cluster plugin. Based on the resulting dendrograms generated from the cluster analysis (FIG. 13), representative trajectory conformations from the two most populated cluster groupings at the third level were used to compare both conformational and electrostatic properties between each peptide.

Structure/Conformation and Electrostatic Properties Comparisons

For structural/conformational comparison, representative conformations from the top two populated clusters were superimposed onto either GPRP ((SEQ ID NO:1) or GPRV (SEQ ID NO:2) peptides in an 'active' conformation within hole 'a' as obtained from previous published fragment D crystal structures (PDB code: 2HPC and 2FFD, respectively); GPRPxxx (SEQ ID NO:26) peptides were compared to 'active' GPRP (SEQ ID NO:1) and GPRVxxx (SEQ ID NO:27) peptides were compared to 'active' GPRV (SEQ ID NO:2). After least-squares superpositioning the first three residues of each conformation along the backbone, the RMSD of the first three residues was calculated with the 'active' GPRP (SEQ ID NO:1) or GPRV (SEQ ID NO:2) as the reference; both the backbone and total atom RMSDs were calculated. For electrostatic comparisons, electrostatic potential surface maps for representative conformations from the top populated cluster group for each peptide were generated with Adaptive Poisson-Boltzmann Solver (APBS) using the CHARMM22 force field parameter set (Baker N A, et al. P Natl Acad Sci USA. 2001; 98(18):10037-10041).

Results

MD simulations were performed to compare conformational structures of the peptides immersed in an aqueous environment prior to engagement with fibrin holes. Due to the large amount of data (i.e. conformations) in a 10 ns MD trajectory, a hierarchical clustering method was used to select a smaller set of conformations representative of the entire MD trajectory (FIG. 13). From this cluster analysis, representative conformations from the two most populated clusters for each peptide were used to compare structural features between experimental peptides. The representative conformations for each peptide were then superimposed on either 'active' GPRP (SEQ ID NO:1) or GPRV (SEQ ID NO:2) peptides obtained from fragment D crystal structures (PDB code: 2HPC and 2FFD, respectively). The superposition of simulation conformations with 'active' conformation was evaluated by calculating the RMSD for atoms (backbone and all atoms) from the first three residues of the simulation conformations in reference to the known active conformations. The lower the RMSD, the better the alignment to the reference point. Ranking the peptides from lowest to highest weighted average RMSD along the backbone was GPRPFPAC (SEQ ID NO:5) (0.607 Å)<GPRVVERC (SEQ ID NO:7) (0.670 Å)<GPRPPERC (SEQ ID NO:6) (0.761 Å)<GPRPAAC (SEQ ID NO:4) (0.801 Å)<GPRVVAAC (SEQ ID NO:8) (1.241 Å) (Table 6).

TABLE 6

Root mean squared deviation (RMSD)

| Peptide | Population (% of total) | Backbone RMSD (Å)* | Total RMSD (Å)* |
|---|---|---|---|
| GPRPAAC | 38% | 0.799 | 4.564 |
| (SEQ ID NO: 4) | 27% | 0.803 | 4.709 |
| GPRPFPAC | 60% | 0.594 | 4.615 |
| (SEQ ID NO: 5) | 17% | .0655 | 4.802 |
| GPRPPERC | 43% | 0.862 | 4.896 |
| (SEQ ID NO: 6) | 31% | 0.623 | 4.894 |
| GPRVVERC | 59% | 0.629 | 5.042 |
| (SEQ ID NO: 7) | 23% | 0.834 | 5.251 |
| GPRVVAAC | 48% | 1.546 | 5.437 |
| (SEQ ID NO: 8) | 28% | 0.717 | 4.757 |

It appears that the Pro-Phe-Pro residues in GPRPFPAC (SEQ ID NO:5) help stabilize the backbone of the first three residues to a conformation similar to 'active' GPRP (SEQ ID NO:1). Similarly, while GPRVVERC (SEQ ID NO:7) and GPRPPERC (SEQ ID NO:6) were chosen to investigate the alterations in electrostatic charge, a salt bridge developed between the 3Arg and 6Glu side chains potentially stabilizing the backbone. The RMSD of all the atoms (i.e. backbone and side chain atoms) in the first three residues were also calculated; here, the weighted average RMSD ranking from lowest to highest was GPRPFPAC (SEQ ID NO:5) (4.656 Å)<GPRPAAC (SEQ ID NO:4) (4.657 Å)<GPRPPERC (SEQ ID NO:6) (4.895 Å)<GPRVVERC (SEQ ID NO:7) (5.101 Å)<GPRVVAAC (SEQ ID NO:8) (5.186 Å). This RMSD ranking inversely correlated with the experimental binding affinity data (i.e. lower RMSD, higher binding affinity). Considering this correlation, the orientation of the side chain groups was evaluated in comparison to the 'active' conformation, particularly the orientation of 3Arg, which is required for binding of fibrin holes. Conventional terminology for torsional side chain angle defines $\chi_1$ as the angle between $N_i$-$C_{\alpha i}$-$C_{\beta i}$-$C_{\gamma i}$, (Chandrasekaran R, et al. Int J Protein Res. 1970; 2(4):223-233); the three common rotamer classifications are gauche− (0 to 120°), trans (120 to 240°), and gauche+ (−120 to 0°) (Ponder J W, et al. Mol. Biol. 1987; 193(4):775-791). In the 'active' conformation for both GPRP (SEQ ID NO:1) and GPRV (SEQ ID NO:2), the 3Arg $\chi_1$ angle is in a gauche+ conformation. However, in assessing the $X_1$ angle of the 3Arg side chain for GPRPAAC (SEQ ID NO:4) and GPRVVAAC (SEQ ID NO:8), it was noted that the angle was predominantly in a trans conformation during the simulation (i.e. pointing toward the carboxyl-terminus of the sequence). In contrast, the 3Arg group in GPRPFPAC (SEQ ID NO:5) was mobile, but predominantly in the gauche+ conformation and rarely the trans conformation. The bulky side chain on 5Phe stericly may hinder electrostatic interactions between 3Arg and the C-terminus as observed in GPRVVAAC (SEQ ID NO:8) and GPRPAAC (SEQ ID NO:4). Additionally, the salt bridge formation between 3Arg and 6Glu in GPRVVERC (SEQ ID NO:7) and GPRPPERC (SEQ ID NO:6) appeared to stabilize the 3Arg side chain in the gauche+ conformation. Collectively, these observations suggest that the 3Arg rotameric classifications depended on properties of the downstream residues.

As previously mentioned, knob:hole interactions are driven by electrostatic interactions. Therefore, electrostatic potential surface maps were generated to display the charge distributions for each peptide variant. The 'active' conformation of GPRV (SEQ ID NO:2) has a noticeably positively charged N-terminus generated by 1Gly and 3Arg; GPRP (SEQ ID NO:1) has similar structure/map properties. For the peptide variants, it was noted that the electrostatic mapping was directly related to the 3Arg side chain rotamer classification, where the gauche+ 3Arg conformations maintained the concentrated positive charge around 1Gly and 3Arg (i.e., GPRPFPAC, SEQ ID NO:5). However, with 3Arg in the trans conformation (i.e., GPRPAAC (SEQ ID NO:6) and GPRVVAAC (SEQ ID NO:8)), the positive charge was more broadly distributed from the N-terminus across to the C-terminus. The addition of -ERC in the sixth through eighth residues resulted in two alterations. First, while the salt bridge between 3Arg and 6Glu stabilized 3Arg in the gauche+ conformation providing a concentrated positive charge at the N-terminus, the presence of 6Glu contributed a slightly negative charge near 3A. Secondly, the additional Arg residue in the seventh position redistributed the positive charge more broadly across the peptide chain. Collectively, these molecular dynamics simulations and subsequent analyses provided snapshots at the molecular level into potential intra-chain interactions that occur in aqueous environments and may contribute to the initial binding interactions with fibrin holes.

Example 11

Maleimide-Activated Peg Conjugated to Knob Peptides Via a C-Terminal Cysteine

Results

Figure 14:
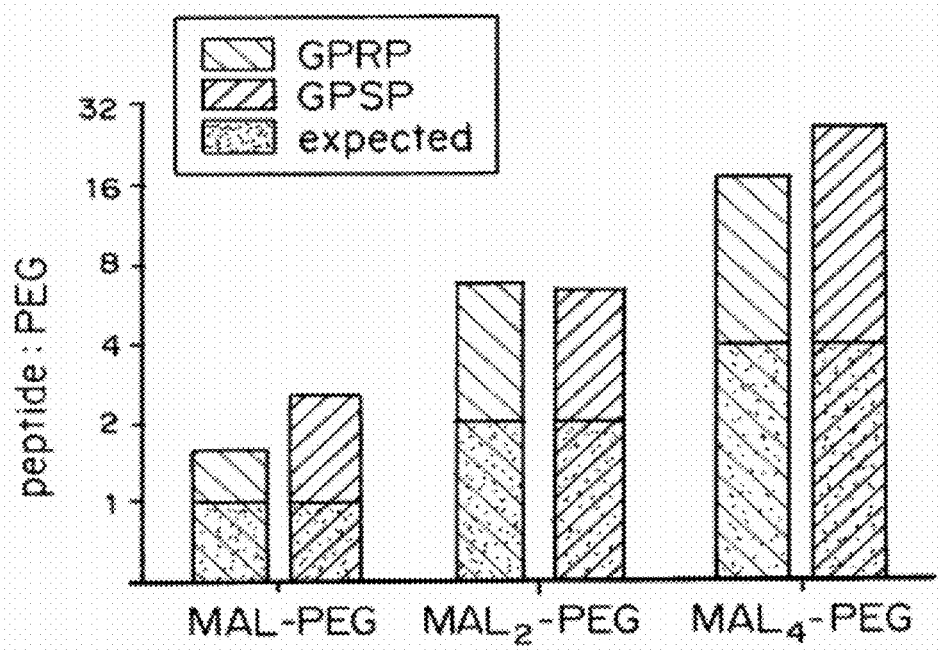
FIG. 14 is a bar graph showing peptide:PEG molar ratio for GPRP (SEQ ID NO:1, left bars) and GPSP (SEQ ID NO:19, right bars) conjugated with three varieties of PEG (MAL-PEG (first set of bars), $MAL_2$-PEG (second set of bars), and $MAL_4$-PEG (third set of bars)). The "expected" ratio is shown superimposed on the actual ratios obtained.

GPRPAAC (SEQ ID NO:4) was used as the model knob peptide sequence to establish feasibility for this set of experiments. Maleimide-activated PEG and a molar excess of synthesized knob peptide, GPRPAAC (SEQ ID NO:4) or GPSPAAC (SEQ ID NO:9, negative control), were reacted in a phosphate-buffered conjugation buffer at room temperature. To maximize the conjugation of PEG to peptide while minimizing the loss of peptide, several different reactant (sulfhydryl-to-maleimide) molar ratios were tested. The reaction mix was subsequently dialyzed into water to remove salt and unreacted peptide. A representative set of conjugation reactions was conducted using the three varieties of PEG (1-arm, 2-arm, 4-arm) that would be used in the development of SA3. PEGylated peptide products were then characterized for PEG concentration using a colorimetric assay based on the partitioning of ferrothiocyanate in a biphasic system (Barker T H, et al. Anal Biochem 2001 March; 290(2):382-385; Nag A, et al. Anal Biochem 1996 Jun. 1; 237(2):224-231). The CBQCA assay (Invitrogen, Carlsbad, Calif.) was used to determine peptide concentration and the molar ratio of peptide to PEG, reflecting the efficiency of the conjugation reaction (FIG. 14).

Example 12

Figure 15A:
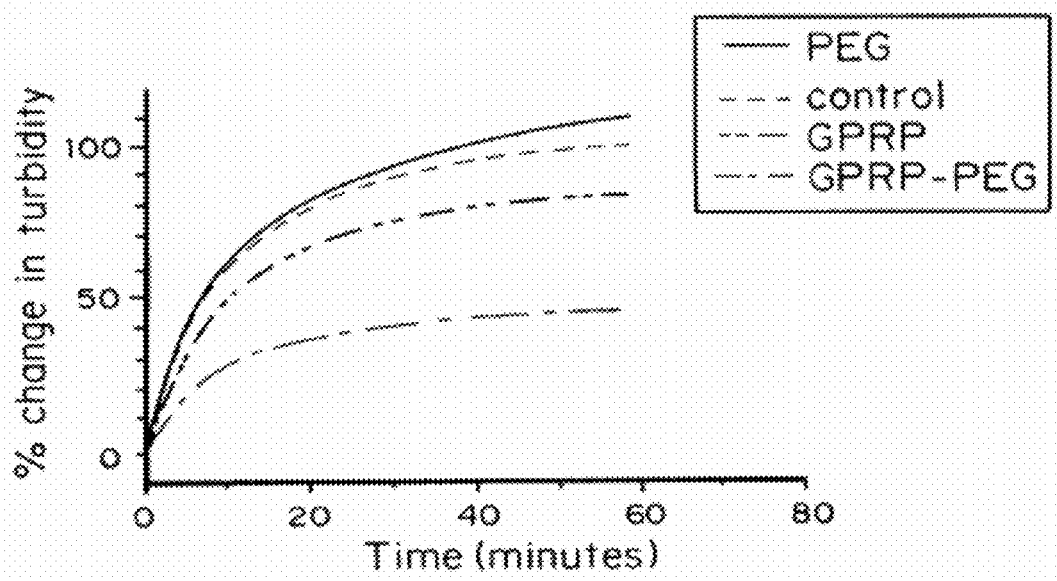
FIG. 15A is a line graph showing percent change in fibrin turbidity as a function of time (minutes) for thrombin-induced fibrin polymerization in the presence of a 10:1 molar ratio of GPRP-PEG (SEQ ID NO:1) conjugate to fibrinogen, GPRP (SEQ ID NO:1) peptide, PEG, or buffer only.
Figure 15B:
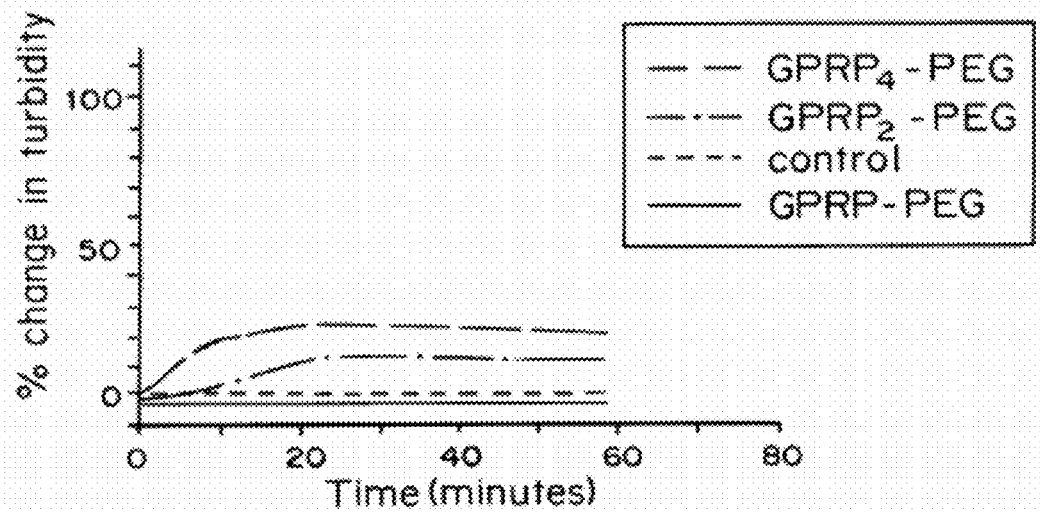
FIGS. 15B and 15C are line graphs showing percent change in fibrin turbidity as a function of time (minutes) in the presence of a 10:1 molar ratio to fibrinogen of knob-PEG conjugates $GPRP_1$-PEG (SEQ ID NO:1), $GPRP_2$-PEG (SEQ ID NO:1) and $GPRP_4$-PEG (SEQ ID NO:1) (FIG. 15B) followed by thrombin-induced polymerization (FIG. 15C).
Figure 15C:
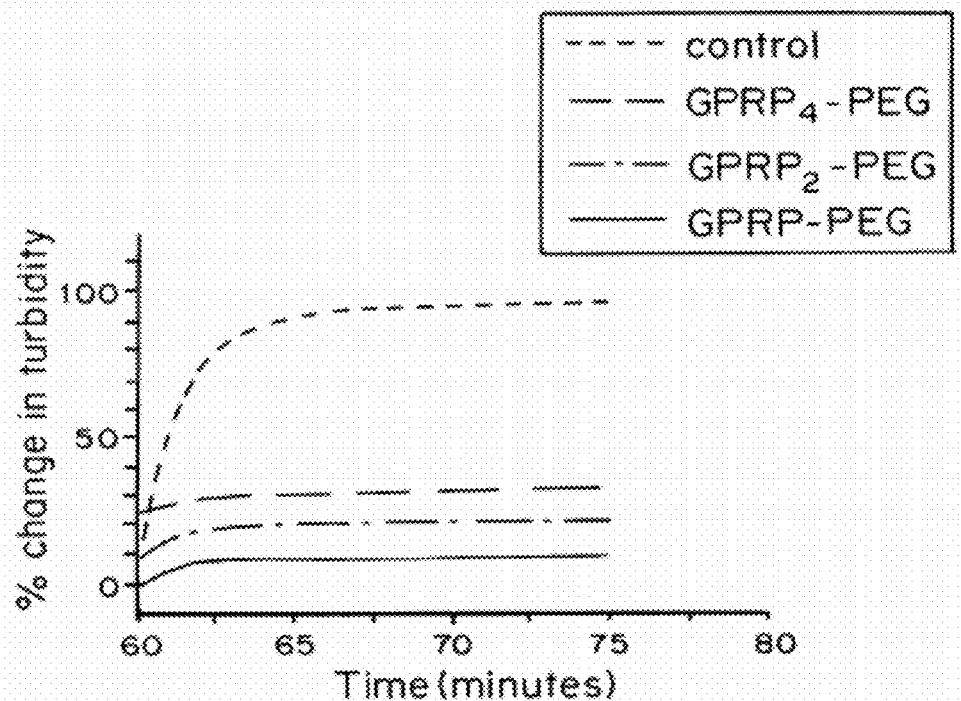

Knob-PEG Conjugates are Capable of Modifying Fibrin Polymerization in a Dose Dependent Manner Results Fibrin polymerization and plasmin degradation assays were used to evaluate the efficacy of the PEG-peptide conjugates generated above. Fibrin polymerization was induced by the addition of a thrombin solution containing the monofunctional PEG-GPRP conjugates (SEQ ID NO:1) product or the unmodified knob and polymerization monitored over an hour by measuring the absorbance at 350 nm (clot turbidity, FIG. 14 (a)). The PEG-GPRP (SEQ ID NO:1) conjugates were more effective in altering the progression of fibrin polymerization compared to the unconjugated peptide at the same concentration (below the active concentration of free knob, i.e. 400 µM) while the unconjugated PEG had no effect (FIG. 15). In a follow-on experiment, fibrinogen was preincubated with knob-PEG conjugates (PEG, $PEG_2$, and $PEG_4$) for 1 hour and turbidity monitored (FIG. 15B). Immediately following the preincubation thrombin was added to the solution and polymerization monitored. The results indicate that the multifunctional knob-PEG conjugates support some type of polymerization, presumably due to knob-pocket interactions, however, upon addition of thrombin the further polymerization (turbidity) was not observed. $PEG_1$-knob inhibited polymerization to 10%.

Example 13

Altered Fibrin Structure with Sub-Inhibiting Concentrations of PEGylated Fibrin Knob Peptides Results Polymerization rate (turbidity curves), percent clottable protein, fiber structure (SEM), and viscoelastic properties of fibrin polymerized in the presence or absence of PEGylated-GPRPFPAC (5 kDa linear PEG chain, SED ID NO:53) at a 1:1 molar ratio were evaluated.

Turbidity and Percent Clottability

Figure 16A:
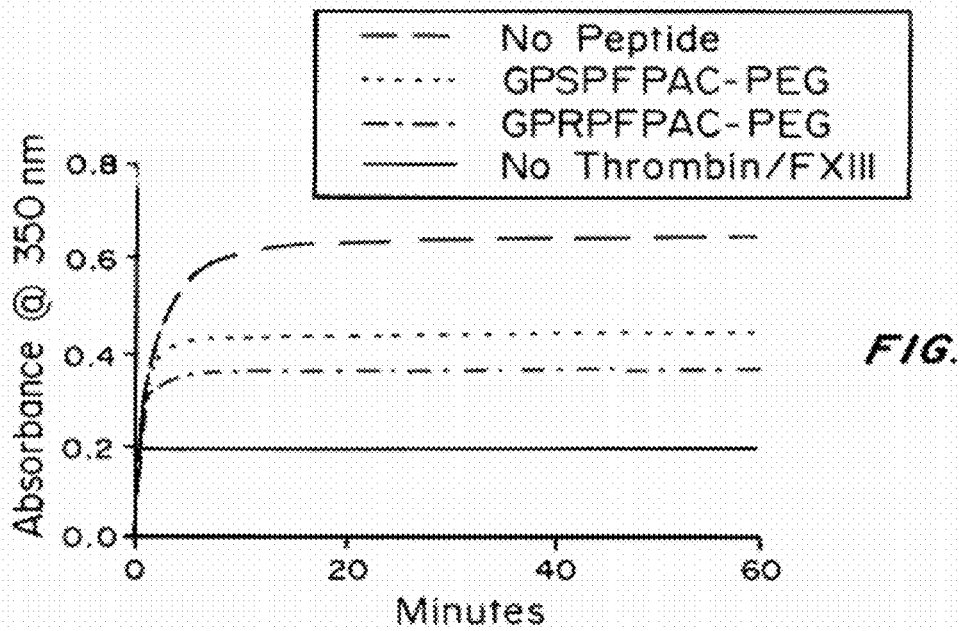
FIG. 16A is a line graph showing turbidity at 350 nm as a function of time (minutes) after control (bottom line) or thrombin-induced polymerization with no peptide (top line), GPSPFPAC-PEG (SEQ ID NO:18, second line from top) or GPRPFPAC-PEG (SEQ ID NO:5, third line from the top).
Figure 16B:
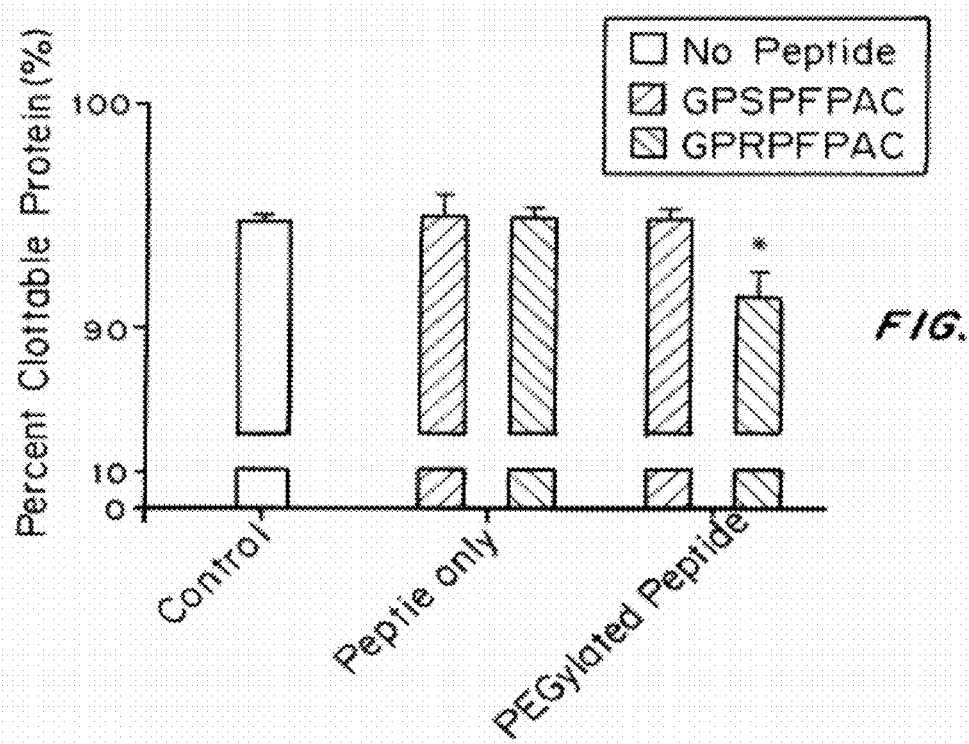
FIG. 16B is a bar graph showing percent clottability after thrombin-induced polymerization with no peptide (first bar), GPSPFPAC-PEG (SEQ ID NO:18, second and fourth bar) or GPRPFPAC-PEG (SEQ ID NO:5, third and fifth bar). *=p<0.01 relative to all groups.

The turbidity curves upon initiating thrombin-activated polymerization and the amount of soluble protein remaining in the clot liquor after polymerization (percent clottable protein) were evaluated. All assays were performed with 1 mg/ml fibrinogen, 1 U/ml thrombin, 1 U/mL factor XIIIa, and 5 mM $CaCl_2$; all PEG conjugates were tested at a 1:1 molar ratio. A lower maximum absorbance turbidity value was observed, indicating thinner fibrin fibers and/or reduced clottable protein (FIG. 16A). However, the percentage of clottable protein did not change for the control GPSPFPAC-PEG (SEQ ID NO:18) and only decreased from ~95% to 92% in the presence of GPRPFPAC-PEG (SEQ ID NO:5) (FIG. 16B). These results indicated that this minor but significant change altered the fibrin fiber microstructure.

Fibrin Structure

Fibrin clots were polymerized in the presence or absence of PEGylated knob peptides at a 1:1 molar ratio. The clots were then fixed, dehydrated with a series of acetone-water solutions and critical point drying (acetone-$CO_2$ exchange). Dehydrated samples were then mounted on aluminum stubs and sputter coated with gold-palladium. Microstructure of the samples were then examined via scanning electron microscopy (Zeiss Ultra SEM) at 15,000× magnification. A more porous structure with thinner fibers were observed with GPRPFPAC-PEG (SEQ ID NO:5) compared to control peptide conjugate (GPSPFPAC-PEG, SEQ ID NO:18) and no peptide control.

Example 14

Results

Peptide variants were based on the thrombin cleaved N-terminus of fibrin Aα chains (A-knob; GPRVVERHQS, SEQ ID NO:40). It is shown that the $1^{st}$, $2^{nd}$, and $3^{rd}$ residues are critical for binding to fibrinogen pockets and at high enough concentrations the peptides compete for pockets and inhibit polymerization. It is also shown that the knob peptide, GPRPFPAC (SEQ ID NO:5), binds with higher affinity to fibrin(ogen) pockets than the gold standard knob peptide, GPRP (SEQ ID NO:1). Additionally, using molecular modeling, key structural and electrostatic properties of GPRPFPAC (SEQ ID NO:5) that enhanced the binding affinity to fibrinogen pockets were identified. Specifically, the 5Phe group appeared to help maintain the 3Arg side chain in the active conformation to maintain a dense positive charge at the N-terminal. In contrast, the low binding peptide GPRVVAAC (SEQ ID NO:8) had a broader positive charge distribution at the N-terminal.

Figure 17:
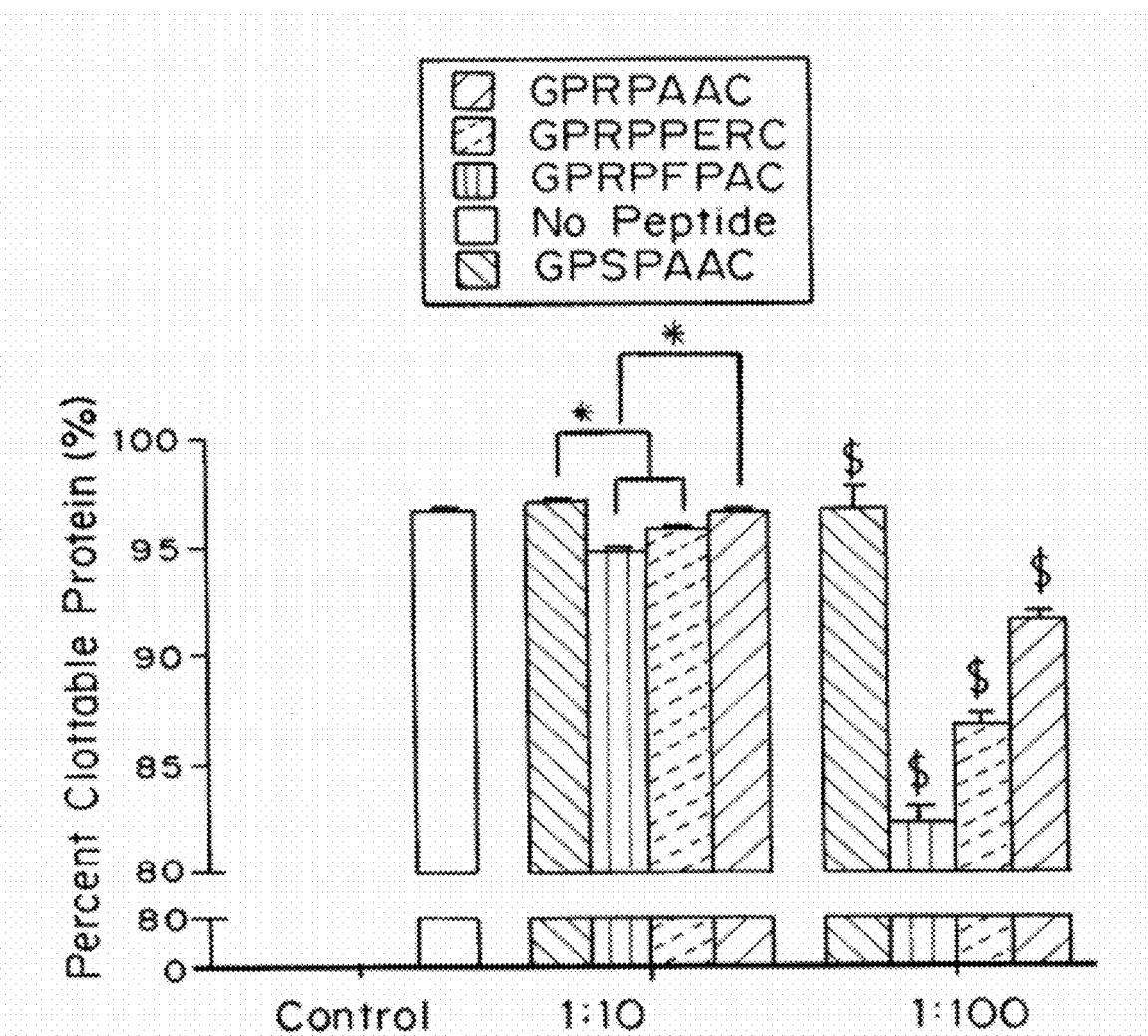
FIG. 17 is a bar graph showing percent clottable protein measured via protein assay after 1 hr of thrombin-induced polymerization in presence or absence of no peptide (first bar), or the fibrin knob peptides GPSPAAC ($2^{nd}$ and $6^{th}$ bars, SEQ ID NO:9), GPRPFPAC ($3^{rd}$ and $7^{th}$ bars, SEQ ID NO:5), GPRPPERC ($4^{th}$ and $8^{th}$ bars, SEQ ID NO:6), or GPRPAAC ($4^{th}$ and $8^{th}$ bars, SEQ ID NO:4). *p<0.05, $ p<0.01 compared to all groups.

The higher affinity knob peptide, GPRPFPAC (SEQ ID NO:5) may therefore inhibit fibrin polymerization more efficiently than the lower affinity knob peptides GPRPAAC (SEQ ID NO:4) and GPRPPERC (SEQ ID NO:6). Therefore, percent clottable protein was measured via protein assay after 1 hr of thrombin-induced polymerization in presence or absence of fibrin knob peptides. Results from these percent clottable protein assays indicated that at the same concentration, GPRPFPAC (SEQ ID NO:5) inhibits fibrin assembly (i.e. clot formation) to a greater extent than GPRPAAC (SEQ ID NO:4) and GPRPPERC (SEQ ID NO:6) (FIG. 17).

Unless defined otherwise, all technical and scientific terms used herein have the same meanings as commonly understood by one of skill in the art to which the disclosed invention belongs. Those skilled in the art will recognize, or be able to ascertain using no more than routine experimentation, many equivalents to the specific embodiments of the invention described herein. Such equivalents are intended to be encompassed by the following claims.

I claim:

1. A recombinant fusion protein, comprising a fibrin knob peptide selected from the group consisting of SEQ ID NOs: 5-8 at the N-terminus of the fusion protein, wherein the fusion protein binds fibrin.

2. The recombinant fusion protein of claim 1, further comprising a bioactive polypeptide that promotes wound healing or fibrinolysis.

3. The recombinant fusion protein of claim 2, wherein the bioactive polypeptide is a growth factor, cytokine, adhesion domain, anti-adhesion domain, immunomodulatory domain, protein-binding domain, nucleic acid-binding domain, polysaccharide-binding domain, virus-binding domain, cytotoxic domain, enzymatically active domain, protease inhibitor, serum protein, or fragment thereof, that binds its receptor.

4. The recombinant fusion protein of claim 3, wherein the bioactive polypeptide is tissue plasminogen activator (tPA), or a fragment thereof that promotes fibrinolysis.

5. The recombinant fusion protein of claim 1, further comprising an inert protein that sterically hinders fibrin polymerization when the fusion protein binds fibrin.

6. The recombinant fusion protein of claim 5, wherein the inert protein is human serum albumin.

7. The recombinant fusion protein of claim 1, conjugated to a polyethylene glycol.

* * * * *

```
                         SEQUENCE LISTING

<160> NUMBER OF SEQ ID NOS: 40

<210> SEQ ID NO 1
<211> LENGTH: 4
<212> TYPE: PRT
<213> ORGANISM: Homo sapiens

<400> SEQUENCE: 1

Gly Pro Arg Pro
1

<210> SEQ ID NO 2
<211> LENGTH: 4
<212> TYPE: PRT
<213> ORGANISM: Homo sapiens

<400> SEQUENCE: 2

Gly Pro Arg Val
1

<210> SEQ ID NO 3
<211> LENGTH: 4
<212> TYPE: PRT
<213> ORGANISM: Homo sapiens

<400> SEQUENCE: 3

Gly His Arg Pro
1

<210> SEQ ID NO 4
<211> LENGTH: 7
<212> TYPE: PRT
<213> ORGANISM: Homo sapiens

<400> SEQUENCE: 4

Gly Pro Arg Pro Ala Ala Cys
1               5

<210> SEQ ID NO 5
<211> LENGTH: 8
<212> TYPE: PRT
<213> ORGANISM: Homo sapiens

<400> SEQUENCE: 5

Gly Pro Arg Pro Phe Pro Ala Cys
1               5
```

```
<210> SEQ ID NO 6
<211> LENGTH: 8
<212> TYPE: PRT
<213> ORGANISM: Homo sapiens

<400> SEQUENCE: 6

Gly Pro Arg Pro Pro Glu Arg Cys
1               5

<210> SEQ ID NO 7
<211> LENGTH: 8
<212> TYPE: PRT
<213> ORGANISM: Homo sapiens

<400> SEQUENCE: 7

Gly Pro Arg Val Val Glu Arg Cys
1               5

<210> SEQ ID NO 8
<211> LENGTH: 8
<212> TYPE: PRT
<213> ORGANISM: Homo sapiens

<400> SEQUENCE: 8

Gly Pro Arg Val Val Ala Ala Cys
1               5

<210> SEQ ID NO 9
<211> LENGTH: 7
<212> TYPE: PRT
<213> ORGANISM: Homo sapiens

<400> SEQUENCE: 9

Gly Pro Ser Pro Ala Ala Cys
1               5

<210> SEQ ID NO 10
<211> LENGTH: 6
<212> TYPE: PRT
<213> ORGANISM: Homo sapiens

<400> SEQUENCE: 10

Gly Pro Arg Pro Ala Ala
1               5

<210> SEQ ID NO 11
<211> LENGTH: 4
<212> TYPE: PRT
<213> ORGANISM: Homo sapiens

<400> SEQUENCE: 11

Gly Ser Pro Glu
1

<210> SEQ ID NO 12
<211> LENGTH: 30
<212> TYPE: DNA
<213> ORGANISM: Homo sapiens

<400> SEQUENCE: 12
actggtcgac tgggtcttga ttccccaact                                    30

<210> SEQ ID NO 13
<211> LENGTH: 40
<212> TYPE: DNA
```

<213> ORGANISM: Homo sapiens

<400> SEQUENCE: 13
actggtcgac tcagcaacca cctgttcggt aattaatgga                                40

<210> SEQ ID NO 14
<211> LENGTH: 8
<212> TYPE: PRT
<213> ORGANISM: Homo sapiens

<400> SEQUENCE: 14

Leu Val Pro Arg Gly Ser Pro Glu
1               5

<210> SEQ ID NO 15
<211> LENGTH: 8
<212> TYPE: PRT
<213> ORGANISM: Homo sapiens

<400> SEQUENCE: 15

Leu Val Pro Arg Gly Pro Arg Val
1               5

<210> SEQ ID NO 16
<211> LENGTH: 8
<212> TYPE: PRT
<213> ORGANISM: Homo sapiens

<400> SEQUENCE: 16

Leu Val Pro Arg Gly Pro Arg Pro
1               5

<210> SEQ ID NO 17
<211> LENGTH: 8
<212> TYPE: PRT
<213> ORGANISM: Homo sapiens

<400> SEQUENCE: 17

Leu Val Pro Arg Gly His Arg Pro
1               5

<210> SEQ ID NO 18
<211> LENGTH: 8
<212> TYPE: PRT
<213> ORGANISM: Homo sapiens

<400> SEQUENCE: 18

Gly Pro Ser Pro Phe Pro Ala Cys
1               5

<210> SEQ ID NO 19
<211> LENGTH: 4
<212> TYPE: PRT
<213> ORGANISM: Homo sapiens

<400> SEQUENCE: 19

Gly Pro Ser Pro
1

<210> SEQ ID NO 20
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)

```
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid

<400> SEQUENCE: 20

Gly Xaa Arg Xaa
1

<210> SEQ ID NO 21
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid

<400> SEQUENCE: 21

Gly Xaa Arg Xaa
1

<210> SEQ ID NO 22
<211> LENGTH: 5
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is any amino acid

<400> SEQUENCE: 22

Gly Pro Arg Pro Xaa
1               5

<210> SEQ ID NO 23
<211> LENGTH: 5
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is any amino acid

<400> SEQUENCE: 23

Gly Pro Arg Val Xaa
1               5

<210> SEQ ID NO 24
<211> LENGTH: 6
<212> TYPE: PRT
<213> ORGANISM: Homo sapiens
<220> FEATURE:
<221> NAME/KEY: MISC_FEATURE
<222> LOCATION: (5)..(6)
<223> OTHER INFORMATION: Xaa is any amino acid

<400> SEQUENCE: 24

Gly Pro Arg Pro Xaa Xaa
1               5

<210> SEQ ID NO 25
<211> LENGTH: 6
<212> TYPE: PRT
<213> ORGANISM: Homo sapiens
```

```
<220> FEATURE:
<221> NAME/KEY: MISC_FEATURE
<222> LOCATION: (5)..(6)
<223> OTHER INFORMATION: Xaa is any amino acid

<400> SEQUENCE: 25

Gly Pro Arg Val Xaa Xaa
1               5

<210> SEQ ID NO 26
<211> LENGTH: 7
<212> TYPE: PRT
<213> ORGANISM: Homo sapiens
<220> FEATURE:
<221> NAME/KEY: MISC_FEATURE
<222> LOCATION: (5)..(7)
<223> OTHER INFORMATION: Xaa is any amino acid

<400> SEQUENCE: 26

Gly Pro Arg Pro Xaa Xaa Xaa
1               5

<210> SEQ ID NO 27
<211> LENGTH: 7
<212> TYPE: PRT
<213> ORGANISM: Homo sapiens
<220> FEATURE:
<221> NAME/KEY: MISC_FEATURE
<222> LOCATION: (5)..(7)
<223> OTHER INFORMATION: Xaa is any amino acid

<400> SEQUENCE: 27

Gly Pro Arg Val Xaa Xaa Xaa
1               5

<210> SEQ ID NO 28
<211> LENGTH: 8
<212> TYPE: PRT
<213> ORGANISM: Homo sapiens
<220> FEATURE:
<221> NAME/KEY: MISC_FEATURE
<222> LOCATION: (5)..(8)
<223> OTHER INFORMATION: Xaa is any amino acid

<400> SEQUENCE: 28

Gly Pro Arg Pro Xaa Xaa Xaa Xaa
1               5

<210> SEQ ID NO 29
<211> LENGTH: 8
<212> TYPE: PRT
<213> ORGANISM: Homo sapiens
<220> FEATURE:
<221> NAME/KEY: MISC_FEATURE
<222> LOCATION: (5)..(8)
<223> OTHER INFORMATION: Xaa is any amino acid

<400> SEQUENCE: 29

Gly Pro Arg Val Xaa Xaa Xaa Xaa
1               5

<210> SEQ ID NO 30
<211> LENGTH: 6
<212> TYPE: PRT
<213> ORGANISM: Homo sapiens
<220> FEATURE:
<221> NAME/KEY: MISC_FEATURE
<222> LOCATION: (4)..(7)
<223> OTHER INFORMATION: Xaa is any amino acid
```

-continued

```
<400> SEQUENCE: 30

Gly Pro Arg Xaa Xaa Xaa
1               5

<210> SEQ ID NO 31
<211> LENGTH: 7
<212> TYPE: PRT
<213> ORGANISM: Homo sapiens
<220> FEATURE:
<221> NAME/KEY: MISC_FEATURE
<222> LOCATION: (6)..(7)
<223> OTHER INFORMATION: Xaa is any amino acid

<400> SEQUENCE: 31

Gly Pro Arg Pro Phe Xaa Xaa
1               5

<210> SEQ ID NO 32
<211> LENGTH: 7
<212> TYPE: PRT
<213> ORGANISM: Homo sapiens
<220> FEATURE:
<221> NAME/KEY: misc
<222> LOCATION: (6)..(7)
<223> OTHER INFORMATION: Xaa is any amino acid

<400> SEQUENCE: 32

Gly Pro Arg Val Phe Xaa Xaa
1               5

<210> SEQ ID NO 33
<211> LENGTH: 12
<212> TYPE: DNA
<213> ORGANISM: Homo sapiens

<400> SEQUENCE: 33
ggatccccgg aa                                                         12

<210> SEQ ID NO 34
<211> LENGTH: 12
<212> TYPE: DNA
<213> ORGANISM: Homo sapiens

<400> SEQUENCE: 34
ggaccccggg ta                                                         12

<210> SEQ ID NO 35
<211> LENGTH: 12
<212> TYPE: DNA
<213> ORGANISM: Homo sapiens

<400> SEQUENCE: 35
ggaccccggc ca                                                         12

<210> SEQ ID NO 36
<211> LENGTH: 12
<212> TYPE: DNA
<213> ORGANISM: Homo sapiens

<400> SEQUENCE: 36
ggacaccggc ca                                                         12

<210> SEQ ID NO 37
<211> LENGTH: 5
<212> TYPE: PRT
<213> ORGANISM: Homo sapiens
```

```
-continued

<400> SEQUENCE: 37

Pro His Ser Arg Asn
1               5

<210> SEQ ID NO 38
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is any amino acid except Pro

<400> SEQUENCE: 38

Val Pro Gly Xaa Gly
1               5

<210> SEQ ID NO 39
<211> LENGTH: 5
<212> TYPE: PRT
<213> ORGANISM: Homo sapiens

<400> SEQUENCE: 39

Val Pro Gly Val Gly
1               5

<210> SEQ ID NO 40
<211> LENGTH: 10
<212> TYPE: PRT
<213> ORGANISM: Homo sapiens

<400> SEQUENCE: 40

Gly Pro Arg Val Val Glu Arg His Gln Ser
1               5                   10
```